US007897788B2

(12) United States Patent
Fecher et al.

(10) Patent No.: US 7,897,788 B2
(45) Date of Patent: Mar. 1, 2011

(54) INDOL-1-YL-ACETIC ACID DERIVATIVES

(75) Inventors: Anja Fecher, Basel (CH); Heinz Fretz, Riehen (CH); Kurt Hilpert, Hofstetten (CH); Markus Riederer, Liestal (CH)

(73) Assignee: Actelion Pharmaceutical Ltd., Allschwil (CH)

( * ) Notice: Subject to any disclaimer, the term of this patent is extended or adjusted under 35 U.S.C. 154(b) by 1196 days.

(21) Appl. No.: 10/598,781

(22) PCT Filed: Mar. 8, 2005

(86) PCT No.: PCT/EP2005/002418
§ 371 (c)(1),
(2), (4) Date: Sep. 11, 2006

(87) PCT Pub. No.: WO2005/094816
PCT Pub. Date: Oct. 13, 2005

(65) Prior Publication Data
US 2007/0208004 A1    Sep. 6, 2007

(30) Foreign Application Priority Data
Mar. 11, 2004   (WO) ................. PCT/EP2004/002492

(51) Int. Cl.
*A61K 31/404*   (2006.01)
*C07D 209/20*   (2006.01)
(52) U.S. Cl. ..................... 548/495; 548/496; 514/419
(58) Field of Classification Search .............. 548/495, 548/496
See application file for complete search history.

(56) References Cited

U.S. PATENT DOCUMENTS

| | | | | |
|---|---|---|---|---|
| 2001/0039286 | A1* | 11/2001 | Dinnell et al. | ................ 514/320 |
| 2003/0158153 | A1 | 8/2003 | Menta et al. | |
| 2005/0014942 | A1* | 1/2005 | Maruyama et al. | ........... 544/183 |

FOREIGN PATENT DOCUMENTS

| | | | |
|---|---|---|---|
| WO | WO 95/07294 | | 3/1995 |
| WO | WO-03/037862 A1 * | | 5/2003 |
| WO | WO 03/101981 A1 | | 12/2003 |
| WO | WO 2005/054232 A1 | | 6/2005 |

OTHER PUBLICATIONS

Chemical Abstracts Registry No. 347911-97-1, entry date into the Registry file on STN is Jul. 24, 2001.*
Souillac, et al., Characterization of Delivery Systems, Differential Scanning Calorimetry in Encyclopedia of Controlled Drug Delivery, 1999, John Wiley & Sons, pp. 212-227.*
Vippagunta et al. (Advanced Drug Delivery Reviews, 48 (2001), pp. 3-26.*
Doan et al., Journal of Clinical Pharmacology, 2005, 45, pp. 751-762.*
Barnes et al., European Respiratory Journal, 2005, 25, pp. 1084-1105.*
Philip L. Gould., International Journal of Pharmaceutics, vol. 33, pp. 201-217 (1986).
Warawa et al., J. Med. Chem., vol. 44, pp. 372-389 (2001).
Gastpar et al., J. Med. Chem., vol. 41, pp. 4965-4972 (1998).
Richard C. Larock et al., "Comprehensive Organic Transformations: A Guide to Functional Group Preparations", Wiley-VCH publishers, Second Edition (1999).
Berge et al., Journal of Pharmaceutical Sciences, vol. 66, pp. 1-19 (1977).
Sawyer et al., British Journal of Pharmacology, vol. 137, pp. 1163-1172 (2002).
Sugimoto et al., The Journal of Pharmacology and Experimental Therapeutics, vol. 305, No. 1, pp. 347-352 (2003).
Hans Bundgaard, "Design of Prodrugs", Elsevier, pp. 7-9, 21-24 (1985).
Moriya et al., Chem. Pharm. Bull., vol. 28, No. 6, pp. 1711-1721 (1980).
R.B. Silverman, The Organic Chemistry of Drug Design and Drug Action, Academic Press, San Diego, CA, U.S.A., pp. 352-401, (1992).
Hata et al., Molecular Pharmacology, vol. 67, pp. 640-647 (2005).
"The Use of indole-3-acetic acids as CRTH2 receptor antagonists", Expert Opin. Ther. Patents, vol. 14, No. 1, pp. 125-128 (2004).

* cited by examiner

*Primary Examiner* — Laura L. Stockton
(74) *Attorney, Agent, or Firm* — Hunton & Williams LLP

(57) ABSTRACT

The invention relates to indol-1-yl-acetic acid derivatives and their use as active ingredients in the preparation of pharmaceutical compositions. The invention also concerns related aspects including processes for the preparation of the compounds, pharmaceutical compositions containing one or more of those compounds and methods of treatment comprising administration of said compounds.

13 Claims, No Drawings

INDOL-1-YL-ACETIC ACID DERIVATIVES

FIELD OF THE INVENTION

The present invention relates to indol-1-yl-acetic acid derivatives and their use as potent "chemoattractant receptor-homologous molecule expressed on Th2 cells" (hereinafter called CRTH2) antagonists in the treatment of prostaglandin mediated diseases, to pharmaceutical compositions containing these derivatives and to processes for their preparation. In particular, at least one of such derivatives of the general formula I may be used in pharmaceutical compositions for the treatment of both chronic and acute allergic/immune disorders comprising allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, basophil-related diseases, such as basophilic leukemia and basophilic leukocytosis in humans and other mammals.

The invention also relates to novel compounds of Formula II which may also be used in pharmaceutical compositions as outlined above.

BACKGROUND OF THE INVENTION

Prostaglandin D2 is a known agonist of the thromboxane A2 (TxA2) receptor, the PGD2 (DP) receptor and the recently identified G-protein-coupled "chemoattractant receptor-homologous molecule expressed on Th2 cells" (CRTH2).

The response to allergen exposure in a previously sensitized host results in a cascade effect involving numerous cell types and release of a number of cytokines, chemokines, and multiple mediators. Among these critical initiators are the cytokines interleukin (IL)-4, IL-13, and IL-5, which play critical roles in Th2 cell differentiation, immunoglobulin (Ig)E synthesis, mast cell growth and differentiation, upregulation of CD23 expression, and the differentiation, recruitment, and activation of eosinophils. The stimulated release of the array of mediators, causes end-organ damage, including constriction and hyperresponsiveness, vascular permeability, edema, mucous secretion, and further inflammation.

Because of the number of responses targeted, corticosteroids have proven to be the most effective therapy. Rather than antagonizing these specific responses in a directed way, another approach is to alter the immune response, that is, to change the nature of the immunological response to allergen. CRTH2 is preferentially expressed on Th2 cells and is a chemoattractant receptor for PGD2 that mediates PGD2-dependent migration of blood Th2 cells. Chemoattractants are responsible for the recruitment of both Th2 cells and other effector cells of allergic inflammation and may provide the conceptual basis for the development of new therapeutic strategies, especially in allergic conditions.

So far, few compounds having CRTH2 antagonistic activity have been reported in the patent literature. Bayer AG claims in GB Patent Specification No. 2 388 540 the use of Ramatroban ((3R)-3-(4-fluorobenzene-sulfonamido)-1,2,3,4-tetrahydrocarbazole-9-propionic acid) for the prophylaxis and treatment of allergic diseases, such as asthma, allergic rhinitis or allergic conjuvatitis (see also *Journal of Pharmacology and Experimental Therapeutics* (2003), 305(1), 347-352, wherein a certain oral bioavailability of Ramatroban and its ability to inhibit prostaglandin D2-induced eosinophil migration in vitro has been reported). Further, (2-tert-butoxycarbonyl-1,2,3,4-tetrahydro-pyrido[4,3-b]indol-5-yl)-acetic acid and (2-ethoxycarbonyl-1,2,3,4-tetrahydro-pyrido[4,3-b]indol-5-yl)-acetic acid are disclosed by Kyle F. et al in two patent specifications i.e. in U.S. Pat. No. 5,817,756 and WO 95/07294, respectively.

More recently, certain 1-carboxymethyl-indole derivatives of the formula

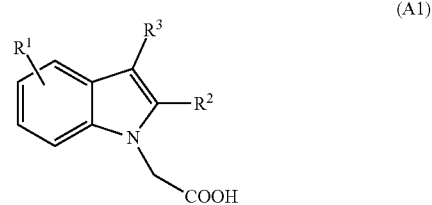

(A1)

wherein $R^1$ can notably be hydrogen, halogen or $C_{1-6}$ alkyl, $R^2$ can notably be hydrogen and $R^3$ is optionally substituted aryl or heteroaryl, have been disclosed. These compounds are presented as being active on the CRTH2 receptor and therefore potentially useful for the treatment of various respiratory diseases.

DESCRIPTION OF THE INVENTION

The present invention firstly relates to the compounds of general formula I

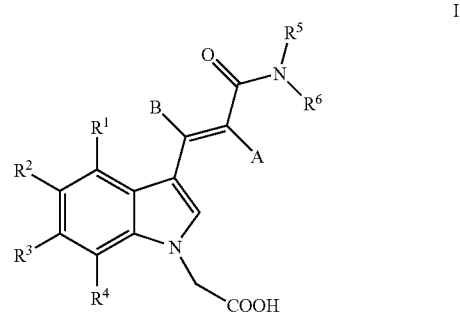

I wherein
A represents hydrogen; alkyl; halogen or cyano;
B represents hydrogen; alkyl or halogen;
$R^1$, $R^2$, $R^3$ and $R^4$ independently represent hydrogen; alkyl; halogen; nitro; cyano or formyl (and preferably independently represent hydrogen, alkyl, halogen or nitro);
$R^5$ and $R^6$ independently represent hydrogen; alkyl; cycloalkyl; cycloalkyl-alkyl; heteroaryl; heteroaryl-alkyl; alkenyl; carboxyalkyl; cyanoalkyl; diphenylalkyl; arylarylalkoxy-aryl, aryl-alkyl, aryl-alkyl-aryl, arylcarbonyl-aryl or aryloxy-aryl, or $R^5$ and $R^6$, together with the nitrogen atom to which they are attached, form a heterocyclic ring system;
for use as medicaments.

Any reference to a compound of general formula I for use as a medicament is to be understood as referring also to optically pure enantiomers, mixtures of enantiomers, racemates, optically pure diastereoisomers, mixtures of diastereoisomers, diastereoisomeric racemates, mixture of diastereoisomeric racemates, meso forms, geometric isomers, as well as solvates and morphological forms and pharmaceutically acceptable salts thereof. The same will apply mutatis mutandis to the compounds of formula I, $I_{C1}$, $I_{C2}$, $I_P$, $II_P$, $III_P$ or $IV_P$ (in which case the reference to the compounds is in addition to be understood as referring also to salts other than pharmaceutically acceptable salts), to the same as medicaments, to the pharmaceutical compositions containing them and to their uses according to the invention.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient. The same will apply mutatis mutandis to the compounds of formula I, $I_{C1}$, $I_{C2}$, $I_P$, $II_P$, $III_P$ or $IV_P$, to the same as medicaments, to the pharmaceutical compositions containing them and to their uses according to the invention.

The compounds of the general formula I are CRTH2 receptor antagonists and may be used for the prevention and treatment of chronic and acute allergic immune disorders comprising allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases comprising Churg-Strauss syndrome and sinusitis, basophil-related diseases, comprising basophilic leukemia and basophilic leukocytosis in humans and other mammals.

Preferred compounds of general formula I for use as medicaments are those wherein at least one of the following characteristics is present:

A is cyano;
B is hydrogen or methyl;
$R^1$, $R^2$, $R^3$ and $R^4$ are all hydrogen atoms or one of $R^1$, $R^2$, $R^3$ and $R^4$ is halogen (preferably fluorine) while the others are all hydrogen;
at least one of $R^5$ and $R^6$ is chosen from the group consisting of heteroaryl, heteroaryl-alkyl, diphenylalkyl, aryl, aryl-alkoxy-aryl, aryl-alkyl, aryl-alkyl-aryl, arylcarbonyl-aryl and aryloxy-aryl; or $R^5$ and $R^6$, together with the nitrogen atom to which they are attached, form a heterocyclic ring system.

Even more preferred compounds of general formula I for use as medicaments are those wherein at least one of the following characteristics is present:

A is cyano;
B is hydrogen;
$R^1$, $R^2$, $R^3$ and $R^4$ are all hydrogen atoms or one of $R^1$, $R^2$, $R^3$ and $R^4$ is halogen (preferably fluorine) while the others are all hydrogen;
$R^5$ is selected from the group consisting of heteroaryl-alkyl, diphenylalkyl, aryl, aryl-alkoxy-aryl, aryl-alkyl, aryl-alkyl-aryl, arylcarbonyl-aryl and aryloxy-aryl (aryl, aryl-alkoxy-aryl, aryl-alkyl, aryl-alkyl-aryl, arylcarbonyl-aryl end aryloxy-aryl being preferably such that their aryl groups are unsubstituted or substituted 1 or 2 times with substituents independently selected from the group consisting of halogen, alkoxy, haloalkoxy and alkylcarbonyl) and $R^6$ is selected from the group consisting of alkyl, alkenyl, cycloalkyl, aryl, arylalkyl and cyanoalkyl (aryl and aryl-alkyl being preferably such that their aryl groups are unsubstituted or substituted 1 or 2 times with substituents independently selected from the group consisting of halogen, alkoxy, haloalkoxy and alkylcarbonyl); or $R^5$ and $R^6$, together with the nitrogen atom to which they are attached, form a dihydrophenanthiridine, dihydroacridine, dihydrodibenzoazocine, dihydrodibenzoazepine, dihydroindole, dihydroquinoline, dibenzoazepine, phenothiazine, oxa-azadibenzocycloheptene, dihydroisoquinoline ring, which may be unsubstituted or substituted with one substituent selected from halogen, methyl, methoxy and trifluoromethyl (and preferably a 5,6-dihydro-phenanthridine, 9,10-dihydro-acridine, 5,6-dihydro-dibenzo[b,f]azocine, 10,11-dihydro-dibenzo[b,f]azepine, 11,12-dihydro-6H-dibenzo[b,f]azocine, 2,3-dihydro-indole, 3,4-dihydro-2H-quinoline, 6,11-dihydro-dibenzo[b,e]azepine, dibenzo[b,f]azepine, 2-chlorophenothiazine, 11H-10-oxa-5-aza-dibenzo[a,d]cycloheptene, 3,4-dihydro-1H-isoquinoline, 7-trifluoromethyl-3,4-dihydro-2H-quinoline, dibenzo[b,f]azepine, 6,11-dihydro-dibenzo[b,e]azepine ring)

According to one particularly preferred embodiment, the compounds of general formula I for use as medicaments will be such that A is cyano, B is hydrogen and $R^1$, $R^2$, $R^3$ and $R^4$ are all hydrogen atoms.

According to another particularly preferred embodiment, the compounds of general formula I for use as medicaments will be such that A is cyano, B is hydrogen and one of $R^1$, $R^2$, $R^3$ and $R^4$ is halogen (preferably fluorine) while the others are all hydrogen. According to an even more particularly preferred embodiment, the compounds of general formula I for use as medicaments will be such that A is cyano, B is hydrogen and one of $R^2$ and $R^3$ is halogen (preferably fluorine) while the other, $R^1$ and $R^4$ are hydrogen atoms; a representative example thereof will be the case wherein $R^2$ is halogen (preferably fluorine) while the other, $R^1$, $R^3$ and $R^4$ are hydrogen atoms.

Still another preferred embodiment regarding the compounds of general formula I for use as medicaments is that wherein the groups $R^5$ and $R^6$ do not form a heterocyclic ring system together with the nitrogen atom to which they are attached. In such case, each of the following combinations will constitute a more particularly preferred embodiment:

$R^5$ being aryl and $R^6$ being selected from the group consisting of alkyl, cycloalkyl, alkenyl, cyanoalkyl, diphenylalkyl, heteroaryl-alkyl, aryl-alkyl and aryl (and preferably $R^5$ being phenyl and $R^6$ being selected from the group consisting of alkyl, cycloalkyl, alkenyl, cyanoalkyl, diphenylalkyl, heteroaryl-alkyl, phenylalkyl and phenyl); or $R^5$ being aryl-alkyl and $R^6$ being selected from the group consisting of alkyl, aryl and aryl-alkyl (and preferably $R^5$ being phenylalkyl and $R^6$ being selected from the group consisting of alkyl, phenyl and phenyl-alkyl).

An alternative preferred embodiment regarding the compounds of general formula I for use as medicaments is that wherein the groups $R^5$ and $R^6$ form a heterocyclic ring system together with the nitrogen atom to which they are attached. In such case, each of the following $NR^5R^6$ groups will constitute a more particularly preferred embodiment:

$NR^5R^6$ being an unsubstituted dihydroquinoline ring (for example —$NR^5R^6$ representing 3,4-dihydro-2H-quinolin-1-yl);

$NR^5R^6$ being an unsubstituted dihydroisoquinoline ring (for example —$NR^5R^6$ representing 3,4-dihydro-1H-isoquinolin-2-yl);

$NR^5R^6$ being an unsubstituted dibenzoazepine ring (for example —$NR^5R^6$ representing dibenzo[b,f]azepin-5-yl);

NR⁵R⁶ being an unsubstituted dihydrodibenzoazepine ring (for example —NR⁵R⁶ representing 6,11-dihydrodibenzo[b,e]azepin-5-yl or a 10,11-dihydrodibenzo[b,f]azepin-5-yl);

NR⁵R⁶ being an unsubstituted phenothiazine ring or a phenothiazine ring substituted once with halogen (for example —NR⁵R⁶ representing 2-chloro-phenothiazin-10-yl);

NR⁵R⁶ being an unsubstituted oxa-aza-dibenzocycloheptene ring (for example —NR⁵R⁶ representing 11H-10-oxa-5-aza-dibenzo[a,d]cyclohepten-5-yl).

Another aspect of the present invention is the use of compounds of the general Formula I as medicaments, in particular to treat the aforementioned diseases. In this respect the use of the following compounds is particularly preferred:

[3-((E)-2-cyano-2-phenylcarbamoyl-vinyl)-indol-1-yl]-acetic acid;
[3-((E)-2-cyano-2-m-tolylcarbamoyl-vinyl)-indol-1-yl]-acetic acid;
{3-[(E)-2-cyano-2-(4-methoxy-phenylcarbamoyl)-vinyl]-indol-1-yl}-acetic acid;
{3-[(E)-2-(3-bromo-phenylcarbamoyl)-2-cyano-vinyl]-indol-1-yl}-acetic acid;
{3-[(E)-2-cyano-2-(cyclohexylmethyl-carbamoyl)-vinyl]-indol-1-yl}-acetic acid;
[3-((E)-2-cyano-2-phenethylcarbamoyl-vinyl)-indol-1-yl]-acetic acid;
[3-((E)-2-cyano-2-isopropylcarbamoyl-vinyl)-indol-1-yl]-acetic acid;
[3-((E)-2-cyano-2-propylcarbamoyl-vinyl)-indol-1-yl]-acetic acid;
[3-((E)-2-cyano-2-cyclohexylcarbamoyl-vinyl)-indol-1-yl]-acetic acid;
{3-[(E)-2-cyano-2-(3-methyl-butylcarbamoyl)-vinyl]-indol-1-yl}-acetic acid;
[3-((E)-2-benzylcarbamoyl-2-cyano-vinyl)-indol-1-yl]-acetic acid;
{3-[(E)-2-(benzyl-phenyl-carbamoyl)-2-cyano-vinyl]-indol-1-yl}-acetic acid;
{3-[(E)-2-cyano-2-(4-cyano-phenylcarbamoyl)-vinyl]-indol-1-yl}-acetic acid;
[3-((E)-2-cyano-2-o-tolylcarbamoyl-vinyl)-indol-1-yl]-acetic acid;
{3-[(E)-2-cyano-2-(4-ethyl-phenylcarbamoyl)-vinyl]-indol-1-yl}-acetic acid;
{3-[(E)-2-cyano-2-(4-fluoro-phenylcarbamoyl)-vinyl]-indol-1-yl}-acetic acid;
{3-[(E)-2-cyano-2-(4-phenoxy-phenylcarbamoyl)-vinyl]-indol-1-yl}-acetic acid;
{3-[(E)-2-cyano-2-(naphthalen-2-ylcarbamoyl)-vinyl]-indol-1-yl}-acetic acid;
{3-[(E)-2-cyano-2-(2-isopropyl-phenylcarbamoyl)-vinyl]-indol-1-yl}-acetic acid;
[3-((E)-2-cyano-2-p-tolylcarbamoyl-vinyl)-indol-1-yl]-acetic acid;
{3-[(E)-2-cyano-2-(4-isopropyl-phenylcarbamoyl)-vinyl]-indol-1-yl}-acetic acid;
{3-[(E)-2-cyano-2-(3-methoxy-phenylcarbamoyl)-vinyl]-indol-1-yl}-acetic acid;
{3-[(E)-2-cyano-2-(3-fluoro-phenylcarbamoyl)-vinyl]-indol-1-yl}-acetic acid;
{3-[(E)-2-cyano-2-(9H-fluoren-2-ylcarbamoyl)-vinyl]-indol-1-yl}-acetic acid;
{3-[(E)-2-cyano-2-(4-propyl-phenylcarbamoyl)-vinyl]-indol-1-yl}-acetic acid;
{3-[(E)-2-(biphenyl-4-ylcarbamoyl)-2-cyano-vinyl]-indol-1-yl}-acetic acid;
{3-[(E)-2-cyano-2-(3,2'-dimethyl-biphenyl-4-ylcarbamoyl)-vinyl]-indol-1-yl}-acetic acid;
{3-[(E)-2-(4-tert-butyl-phenylcarbamoyl)-2-cyano-vinyl]-indol-1-yl}-acetic acid;
{3-[(E)-2-(2-benzyl-phenylcarbamoyl)-2-cyano-vinyl]-indol-1-yl}-acetic acid;
{3-[(E)-2-(4-butyl-phenylcarbamoyl)-2-cyano-vinyl]-indol-1-yl}-acetic acid;
{3-[(E)-2-(2-acetyl-phenylcarbamoyl)-2-cyano-vinyl]-indol-1-yl}-acetic acid;
{3-[(E)-2-cyano-2-(indan-5-ylcarbamoyl)-vinyl]-indol-1-yl}-acetic acid;
{3-[(E)-2-cyano-2-(4-sec-butyl-phenylcarbamoyl)-vinyl]-indol-1-yl}-acetic acid;
{3-[(E)-2-cyano-2-(4-ethoxy-phenylcarbamoyl)-vinyl]-indol-1-yl}-acetic acid;
{3-[(E)-2-cyano-2-(3-ethoxy-phenylcarbamoyl)-vinyl]-indol-1-yl}-acetic acid;
{3-[(E)-2-cyano-2-(2-propyl-phenylcarbamoyl)-vinyl]-indol-1-yl}-acetic acid;
{3-[(E)-2-cyano-2-(3-phenoxy-phenylcarbamoyl)-vinyl]-indol-1-yl}-acetic acid;
{3-[(E)-2-cyano-2-(3-ethyl-phenylcarbamoyl)-vinyl]-indol-1-yl}-acetic acid;
{3-[(E)-2-cyano-2-(2-ethoxy-phenylcarbamoyl)-vinyl]-indol-1-yl}-acetic acid;
{3-[(E)-2-(3-benzyloxy-phenylcarbamoyl)-2-cyano-vinyl]-indol-1-yl}-acetic acid;
{3-[(E)-2-(4-bromo-phenylcarbamoyl)-2-cyano-vinyl]-indol-1-yl}-acetic acid;
{3-[(E)-2-cyano-2-(4-iodo-phenylcarbamoyl)-vinyl]-indol-1-yl}-acetic acid;
{3-[(E)-2-cyano-2-(3-iodo-phenylcarbamoyl)-vinyl]-indol-1-yl}-acetic acid;
(3-{(E)-2-cyano-2-[(4-fluoro-phenyl)-methyl-carbamoyl]-vinyl}-indol-1-yl)-acetic acid;
(3-{(E)-2-cyano-2-[(4-methoxy-phenyl)-methyl-carbamoyl]-vinyl}-indol-1-yl)-acetic acid;
{3-[(E)-2-cyano-2-(methyl-phenyl-carbamoyl)-vinyl]-indol-1-yl}-acetic acid;
{3-[(E)-2-cyano-3-(3,4-dihydro-2H-quinolin-1-yl)-3-oxo-propenyl]-indol-1-yl}-acetic acid;
{3-[(E)-2-cyano-2-(methyl-p-tolyl-carbamoyl)-vinyl]-indol-1-yl}-acetic acid;
(3-{(E)-2-cyano-2-[2-(2,4-dichloro-phenoxy)-phenylcarbamoyl]-vinyl}-indol-1-yl)-acetic acid;
{3-[(E)-2-cyano-2-(2,5-dimethyl-phenylcarbamoyl)-vinyl]-indol-1-yl}-acetic acid;
{3-[(E)-2-cyano-2-(9-ethyl-9H-carbazol-3-ylcarbamoyl)-vinyl]-indol-1-yl}-acetic acid;
{3-[(E)-2-(3,5-bis-trifluoromethyl-phenylcarbamoyl)-2-cyano-vinyl]-indol-1-yl}-acetic acid;
{3-[(E)-2-cyano-2-(5-methoxy-2-methyl-phenylcarbamoyl)-vinyl]-indol-1-yl}-acetic acid;
{3-[(E)-2-(3-benzoyl-phenylcarbamoyl)-2-cyano-vinyl]-indol-1-yl}-acetic acid;
{3-[(E)-2-(4-benzyloxy-phenylcarbamoyl)-2-cyano-vinyl]-indol-1-yl}-acetic acid;
{3-[(E)-2-cyano-2-(3-nitro-phenylcarbamoyl)-vinyl]-indol-1-yl}-acetic acid;
{3-[(E)-2-cyano-2-(9-oxo-9H-fluoren-2-ylcarbamoyl)-vinyl]-indol-1-yl}-acetic acid;
{3-[(E)-2-cyano-2-(4-methoxy-biphenyl-3-ylcarbamoyl)-vinyl]-indol-1-yl}-acetic acid;
{3-[(E)-2-cyano-2-(2-methoxy-dibenzofuran-3-ylcarbamoyl)-vinyl]-indol-1-yl}-acetic acid;

{3-[(E)-2-cyano-2-(9-oxo-9H-fluoren-4-ylcarbamoyl)-vinyl]-indol-1-yl}-acetic acid;
{3-[(E)-2-cyano-2-(9-oxo-9H-fluoren-1-ylcarbamoyl)-vinyl]-indol-1-yl}-acetic acid;
{3-[(E)-2-(2-benzoyl-phenylcarbamoyl)-2-cyano-vinyl]-indol-1-yl}-acetic acid;
{3-[(E)-2-(3-chloro-4-methoxy-phenylcarbamoyl)-2-cyano-vinyl]-indol-1-yl}-acetic acid;
{3-[(E)-2-(5-chloro-2-methoxy-phenylcarbamoyl)-2-cyano-vinyl]-indol-1-yl}-acetic acid;
3-[(E)-3-(1-carboxymethyl-1H-indol-3-yl)-2-cyano-acryloylamino]-4-methyl-benzoic acid methyl ester;
{3-[(E)-2-(4-chloro-2-methyl-phenylcarbamoyl)-2-cyano-vinyl]-indol-1-yl}-acetic acid;
2-[(E)-3-(1-carboxymethyl-1H-indol-3-yl)-2-cyano-acryloylamino]-benzoic acid methyl ester;
{3-[(E)-2-cyano-2-(4-trifluoromethoxy-phenylcarbamoyl)-vinyl]-indol-1-yl}-acetic acid;
{3-[(E)-2-cyano-2-(3,5-dimethyl-phenylcarbamoyl)-vinyl]-indol-1-yl}-acetic acid;
{3-[(E)-2-(3-bromo-4-methyl-phenylcarbamoyl)-2-cyano-vinyl]-indol-1-yl}-acetic acid;
{3-[(E)-2-(4-bromo-3-methyl-phenylcarbamoyl)-2-cyano-vinyl]-indol-1-yl}-acetic acid;
4-[(E)-3-(1-carboxymethyl-1H-indol-3-yl)-2-cyano-acryloylamino]-benzoic acid ethyl ester;
3-[(E)-3-(1-carboxymethyl-1H-indol-3-yl)-2-cyano-acryloylamino]-benzoic acid methyl ester;
{3-[(E)-2-cyano-2-(4-trifluoromethyl-phenylcarbamoyl)-vinyl]-indol-1-yl}-acetic acid;
{3-[(E)-2-cyano-2-(3,5-dimethoxy-phenylcarbamoyl)-vinyl]-indol-1-yl}-acetic acid;
{3-[(E)-2-(4-bromo-3-chloro-phenylcarbamoyl)-2-cyano-vinyl]-indol-1-yl}-acetic acid;
{3-[(E)-2-(4-bromo-2-methyl-phenylcarbamoyl)-2-cyano-vinyl]-indol-1-yl}-acetic acid;
{3-[(E)-2-(4-acetyl-phenylcarbamoyl)-2-cyano-vinyl]-indol-1-yl}-acetic acid;
{3-[(E)-2-(2-bromo-4-methyl-phenylcarbamoyl)-2-cyano-vinyl]-indol-1-yl}-acetic acid;
{3-[(E)-2-(benzo[1,3]dioxol-5-ylcarbamoyl)-2-cyano-vinyl]-indol-1-yl}-acetic acid;
{3-[(E)-2-cyano-2-(2,3-dihydro-benzo[1,4]dioxin-6-ylcarbamoyl)-vinyl]-indol-1-yl}-acetic acid;
{3-[(E)-2-cyano-2-(2-methoxy-phenylcarbamoyl)-vinyl]-indol-1-yl}-acetic acid;
{3-[(E)-2-cyano-2-(2-phenoxy-phenylcarbamoyl)-vinyl]-indol-1-yl}-acetic acid;
{3-[(E)-2-cyano-2-(phenethyl-phenyl-carbamoyl)-vinyl]-indol-1-yl}-acetic acid;
{3-[(E)-2-cyano-3-(11,12-dihydro-6H-dibenzo[b,f]azocin-5-yl)-3-oxo-propenyl]-indol-1-yl}-acetic acid;
[3-((E)-2-cyano-2-diphenylcarbamoyl-vinyl)-indol-1-yl]-acetic acid;
sodium[3-((E)-2-cyano-3-dibenzo[b,f]azepin-5-yl-3-oxo-propenyl)-indol-1-yl]-acetate;
(3-{(E)-2-[(4-chloro-phenyl)-methyl-carbamoyl]-2-cyano-vinyl}-indol-1-yl)-acetic acid;
{3-[(E)-2-cyano-3-(6,11-dihydro-dibenzo[b,e]azepin-5-yl)-3-oxo-propenyl]-indol-1-yl}-acetic acid;
[3-((E)-2-cyano-2-diphenethylcarbamoyl-vinyl)-indol-1-yl]-acetic acid;
{3-[(E)-2-cyano-3-(10,11-dihydro-dibenzo[b,f]azepin-5-yl)-3-oxo-propenyl]-indol-1-yl}-acetic acid;
(3-{(E)-2-cyano-2-[methyl-((R)-1-phenyl-ethyl)-carbamoyl]-vinyl}-indol-1-yl)-acetic acid;
{3-[(E)-2-(benzyl-methyl-carbamoyl)-2-cyano-vinyl]-indol-1-yl}-acetic acid;
(3-{(E)-2-[(4-acetyl-phenyl)-methyl-carbamoyl]-2-cyano-vinyl}-indol-1-yl)-acetic acid;
(3-{(E)-2-[(4-acetyl-phenyl)-furan-2-ylmethyl-carbamoyl]-2-cyano-vinyl}-indol-1-yl)-acetic acid;
{3-[(E)-2-(benzyl-carboxymethyl-carbamoyl)-2-cyano-vinyl]-indol-1-yl}-acetic acid;
3-{benzyl-[(E)-3-(1-carboxymethyl-1H-indol-3-yl)-2-cyano-acryloyl]-amino}-propionic acid;
{3-[(E)-2-cyano-3-(2,3-dihydro-indol-1-yl)-3-oxo-propenyl]-indol-1-yl}-acetic acid;
{3-[(E)-2-(carboxymethyl-phenyl-carbamoyl)-2-cyano-vinyl]-indol-1-yl}-acetic acid;
(3-{(E)-2-cyano-2-[(2-cyano-ethyl)-phenyl-carbamoyl]-vinyl}-indol-1-yl)-acetic acid;
(3-{(E)-2-[(3-chloro-phenyl)-methyl-carbamoyl]-2-cyano-vinyl}-indol-1-yl)-acetic acid;
{3-[(E)-2-(allyl-phenyl-carbamoyl)-2-cyano-vinyl]-indol-1-yl}-acetic acid;
{3-[(E)-2-cyano-2-(cyclohexyl-phenyl-carbamoyl)-vinyl]-indol-1-yl}-acetic acid;
{3-[(E)-2-cyano-2-(methyl-o-tolyl-carbamoyl)-vinyl]-indol-1-yl}-acetic acid;
{3-[(E)-2-cyano-2-(ethyl-phenyl-carbamoyl)-vinyl]-indol-1-yl}-acetic acid;
{3-[(E)-2-(butyl-phenyl-carbamoyl)-2-cyano-vinyl]-indol-1-yl}-acetic acid;
[5-bromo-3-((E)-2-cyano-2-phenylcarbamoyl-vinyl)-indol-1-yl]-acetic acid;
[3-((E)-2-cyano-2-phenylcarbamoyl-vinyl)-7-methyl-indol-1-yl]-acetic acid;
[3-((E)-2-cyano-2-phenylcarbamoyl-vinyl)-5-fluoro-indol-1-yl]-acetic acid;
[3-((E)-2-cyano-2-phenylcarbamoyl-vinyl)-6-fluoro-indol-1-yl]-acetic acid;
[3-((E)-2-cyano-2-phenylcarbamoyl-vinyl)-6-nitro-indol-1-yl]-acetic acid;
[3-((E)-2-cyano-2-phenylcarbamoyl-vinyl)-5-methyl-indol-1-yl]-acetic acid;
{3-[(E)-3-(2-chloro-phenothiazin-10-yl)-2-cyano-3-oxo-propenyl]-indol-1-yl}-acetic acid;
{3-[(E)-2-cyano-2-(phenyl-thiophen-3-ylmethyl-carbamoyl)-vinyl]-indol-1-yl}-acetic acid;
(3-{(E)-2-cyano-2-[(2,2-diphenyl-ethyl)-phenyl-carbamoyl]-vinyl}-indol-1-yl)-acetic acid;
(3-{(E)-2-cyano-2-[phenyl-(3-phenyl-propyl)-carbamoyl]-vinyl}-indol-1-yl)-acetic acid;
[3-((E)-2-cyano-2-{[2-(4-fluoro-phenyl)-ethyl]-phenyl-carbamoyl}-vinyl)-indol-1-yl]-acetic acid;
{3-[(E)-2-cyano-3-(11H-10-oxa-5-aza-dibenzo[a,d]cyclohepten-5-yl)-3-oxo-propenyl]-indol-1-yl}-acetic acid;
{3-[(E)-2-cyano-2-(isopropyl-phenyl-carbamoyl)-vinyl]-indol-1-yl}-acetic acid;
(3-{(E)-2-cyano-2-[(3,4-dichloro-phenyl)-methyl-carbamoyl]-vinyl}-indol-1-yl)-acetic acid;
(3-{(E)-2-cyano-2-[ethyl-(4-trifluoromethoxy-phenyl)-carbamoyl]-vinyl}-indol-1-yl)-acetic acid;
{3-[(E)-2-(benzhydryl-carbamoyl)-2-cyano-vinyl]-indol-1-yl}-acetic acid;
(3-{(E)-2-cyano-2-[methyl-(2-trifluoromethoxy-phenyl)-carbamoyl]-vinyl}-indol-1-yl)-acetic acid;
{3-[(E)-2-cyano-2-(2,4-difluoro-phenylcarbamoyl)-vinyl]-indol-1-yl}-acetic acid;
(3-{(E)-2-cyano-2-[methyl-(4-trifluoromethoxy-phenyl)-carbamoyl]-vinyl}-indol-1-yl)-acetic acid;

{3-[(E)-2-cyano-2-(ethyl-naphthalen-1-yl-carbamoyl)-vinyl]-indol-1-yl}-acetic acid;
(3-{(E)-2-cyano-2-[(2,4-difluoro-phenyl)-methyl-carbamoyl]-vinyl}-indol-1-yl)-acetic acid;
{3-[(E)-2-cyano-2-(2,4,6-trifluoro-phenylcarbamoyl)-vinyl]-indol-1-yl}-acetic acid;
{3-[(E)-2-cyano-2-(2,3,4-trifluoro-phenylcarbamoyl)-vinyl]-indol-1-yl}-acetic acid;
{3-[(E)-2-cyano-3-(3,4-dihydro-1H-isoquinolin-2-yl)-3-oxo-propenyl]-indol-1-yl}-acetic acid;
{3-[(E)-2-cyano-3-oxo-3-(7-trifluoromethyl-3,4-dihydro-2H-quinolin-1-yl)-propenyl]-indol-1-yl}-acetic acid;
(3-{(E)-2-cyano-2-[(3-fluoro-phenyl)-methyl-carbamoyl]-vinyl}-indol-1-yl)-acetic acid;
[3-((E)-2-cyano-3-dibenzo[b,f]azepin-5-yl-3-oxo-propenyl)-5-fluoro-indol-1-yl]-acetic acid;
{3-[(E)-2-cyano-3-(6,11-dihydro-dibenzo[b,e]azepin-5-yl)-3-oxo-propenyl]-5-fluoro-indol-1-yl}-acetic acid;
{3-[(E)-2-(benzyl-phenyl-carbamoyl)-2-cyano-vinyl]-5-fluoro-indol-1-yl}-acetic acid;
{3-[(E)-2-cyano-2-(cyclohexyl-phenyl-carbamoyl)-vinyl]-5-fluoro-indol-1-yl}-acetic acid;
{3-[(E)-2-(butyl-phenyl-carbamoyl)-2-cyano-vinyl]-5-fluoro-indol-1-yl}-acetic acid;
(3-{(E)-2-cyano-2-[(4-fluoro-phenyl)-methyl-carbamoyl]-vinyl}-5-fluoro-indol-1-yl)-acetic acid;
(3-{(E)-2-cyano-2-[(3-fluoro-phenyl)-methyl-carbamoyl]-vinyl}-5-fluoro-indol-1-yl)-acetic acid;
(3-{(E)-2-cyano-2-[(3,4-dichloro-phenyl)-methyl-carbamoyl]-vinyl}-5-fluoro-indol-1-yl)-acetic acid;
(3-{(E)-2-cyano-2-[methyl-(2-trifluoromethyl-phenyl)-carbamoyl]-vinyl}-5-fluoro-indol-1-yl)-acetic acid;
(3-{(E)-2-cyano-2-[(2,4-difluoro-phenyl)-methyl-carbamoyl]-vinyl}-5-fluoro-indol-1-yl)-acetic acid;
{3-[(E)-2-cyano-2-(phenyl-thiophen-3-ylmethyl-carbamoyl)-vinyl]-5-fluoro-indol-1-yl}-acetic acid;
{3-[(E)-2-cyano-3-oxo-3-(7-trifluoromethyl-3,4-dihydro-2H-quinolin-1-yl)-propenyl]-5-fluoro-indol-1-yl}-acetic acid;
(3-{(E)-2-cyano-2-[ethyl-(4-trifluoromethoxy-phenyl)-carbamoyl]-vinyl}-5-fluoro-indol-1-yl)-acetic acid;
{3-[(E)-2-cyano-3-(3,4-dihydro-1H-isoquinolin-2-yl)-3-oxo-propenyl]-5-fluoro-indol-1-yl}-acetic acid;
{3-[(E)-2-cyano-2-(phenethyl-phenyl-carbamoyl)-vinyl]-5-fluoro-indol-1-yl}-acetic acid;
[3-((E)-2-cyano-3-dibenzo[b,f]azepin-5-yl-3-oxo-propenyl)-6-methyl-indol-1-yl]-acetic acid;
{3-[(E)-2-cyano-3-(6,11-dihydro-dibenzo[b,e]azepin-5-yl)-3-oxo-propenyl]-6-methyl-indol-1-yl}-acetic acid;
{3-[(E)-2-cyano-3-(10,11-dihydro-dibenzo[b,f]azepin-5-yl)-3-oxo-propenyl]-6-methyl-indol-1-yl}-acetic acid;
{3-[(E)-2-(benzyl-phenyl-carbamoyl)-2-cyano-vinyl]-6-methyl-indol-1-yl}-acetic acid;
{3-[(E)-2-cyano-2-(cyclohexyl-phenyl-carbamoyl)-vinyl]-6-methyl-indol-1-yl}-acetic acid;
(3-{(E)-2-cyano-2-[(4-fluoro-phenyl)-methyl-carbamoyl]-vinyl}-6-methyl-indol-1-yl)-acetic acid;
{3-[(E)-2-(butyl-phenyl-carbamoyl)-2-cyano-vinyl]-6-methyl-indol-1-yl}-acetic acid;
{3-[(E)-2-cyano-2-(cyclohexyl-phenyl-carbamoyl)-vinyl]-7-methyl-indol-1-yl}-acetic acid;
(3-{(E)-2-cyano-2-[(4-fluoro-phenyl)-methyl-carbamoyl]-vinyl}-7-methyl-indol-1-yl)-acetic acid.

Furthermore, the use of the first 112 compounds of the above list as medicaments, in particular to treat the aforementioned diseases, is more particularly preferred.

The invention more generally relates to compounds of general formula I, and notably to the 156 compounds listed above (and in particular the first 112 compounds).

Compounds of the above general formula I are novel, with the exception of the following compounds which, however, are also potent CRTH2 receptor antagonists and in this respect are not described in the literature:
{3-[(E)-2-cyano-2-(4-fluoro-phenylcarbamoyl)-vinyl]-indol-1-yl}-acetic acid;
[3-((E)-2-cyano-2-m-tolylcarbamoyl-vinyl)-indol-1-yl]-acetic acid;
{3-[(E)-2-(3-bromo-phenylcarbamoyl)-2-cyano-vinyl]-indol-1-yl}-acetic acid;
[3-((E)-2-cyano-2-phenylcarbamoyl-vinyl)-indol-1-yl]-acetic acid;
[3-((E)-2-benzylcarbamoyl-2-cyano-vinyl)-indol-1-yl]-acetic acid;
[3-((E)-2-cyano-2-o-tolylcarbamoyl-vinyl)-indol-1-yl]-acetic acid;
[3-((E)-2-cyano-2-p-tolylcarbamoyl-vinyl)-indol-1-yl]-acetic acid;
{3-[(E)-2-(4-bromo-phenylcarbamoyl)-2-cyano-vinyl]-indol-1-yl}-acetic acid;
{3-[(E)-2-cyano-2-(4-ethyl-phenylcarbamoyl)-vinyl]-indol-1-yl}-acetic acid;
{3-[(E)-2-cyano-2-(4-methoxy-phenylcarbamoyl)-vinyl]-indol-1-yl}-acetic acid;
{3-[(E)-2-cyano-2-(4-ethoxy-phenylcarbamoyl)-vinyl]-indol-1-yl}-acetic acid;
[3-((E)-2-cyano-2-isopropylcarbamoyl-vinyl)-indol-1-yl]-acetic acid;
{3-[(E)-2-cyano-2-(3-ethoxy-phenylcarbamoyl)-vinyl]-indol-1-yl}-acetic acid;
{3-[(E)-2-cyano-3-[[2-(1H-indol-3-yl)ethyl]amino]-3-oxo-1-propenyl]-indol-1-yl}-acetic acid;
{3-[(E)-2-cyano-2-(4-chloro-phenylcarbamoyl)-vinyl]-indol-1-yl}-acetic acid;
{3-[(E)-2-cyano-3-(4-methyl-piperidin-1-yl)-3-oxo-propenyl]-indol-1-yl}-acetic acid;
{3-[(E)-2-(3-chloro-4-methyl-phenylcarbamoyl)-2-cyano-vinyl]-indol-1-yl}-acetic acid;
{3-[(E)-2-cyano-2-(3-phenyl-propylcarbamoyl)-vinyl]-indol-1-yl}-acetic acid;
{3-[(E)-2-cyano-2-(2,3-dichloro-phenylcarbamoyl)-vinyl]-indol-1-yl}-acetic acid;
{3-[(E)-2-(5-chloro-2-methyl-phenylcarbamoyl)-2-cyano-vinyl]-indol-1-yl}-acetic acid;
{3-[(E)-2-cyano-2-(4-methoxy-benzylcarbamoyl)-vinyl]-indol-1-yl}-acetic acid;
{3-[(E)-2-cyano-2-(2-fluoro-phenylcarbamoyl)-vinyl]-indol-1-yl}-acetic acid;
{3-[(E)-2-cyano-3-oxo-3-(4-phenyl-piperazin-1-yl)-propenyl]-indol-1-yl}-acetic acid.

A further object of the invention therefore relates to compounds of general formula I selected from the group consisting of:
{3-[(E)-2-cyano-2-(cyclohexylmethyl-carbamoyl)-vinyl]-indol-1-yl}-acetic acid;
[3-((E)-2-cyano-2-phenethylcarbamoyl-vinyl)-indol-1-yl]-acetic acid;
[3-((E)-2-cyano-2-isopropylcarbamoyl-vinyl)-indol-1-yl]-acetic acid;
[3-((E)-2-cyano-2-propylcarbamoyl-vinyl)-indol-1-yl]-acetic acid;
[3-((E)-2-cyano-2-cyclohexylcarbamoyl-vinyl)-indol-1-yl]-acetic acid {3-[(E)-2-cyano-2-(3-methyl-butylcarbamoyl)-vinyl]-indol-1-yl}-acetic acid;
{3-[(E)-2-(benzyl-phenyl-carbamoyl)-2-cyano-vinyl]-indol-1-yl}-acetic acid;
{3-[(E)-2-cyano-2-(4-cyano-phenylcarbamoyl)-vinyl]-indol-1-yl}-acetic acid;
{3-[(E)-2-cyano-2-(4-fluoro-phenylcarbamoyl)-vinyl]-indol-1-yl}-acetic acid;
{3-[(E)-2-cyano-2-(4-phenoxy-phenylcarbamoyl)-vinyl]-indol-1-yl}-acetic acid;
{3-[(E)-2-cyano-2-(naphthalen-2-ylcarbamoyl)-vinyl]-indol-1-yl}-acetic acid;
{3-[(E)-2-cyano-2-(2-isopropyl-phenylcarbamoyl)-vinyl]-indol-1-yl}-acetic acid;
{3-[(E)-2-cyano-2-(4-isopropyl-phenylcarbamoyl)-vinyl]-indol-1-yl}-acetic acid;
{3-[(E)-2-cyano-2-(3-methoxy-phenylcarbamoyl)-vinyl]-indol-1-yl}-acetic acid;
{3-[(E)-2-cyano-2-(3-fluoro-phenylcarbamoyl)-vinyl]-indol-1-yl}-acetic acid;
{3-[(E)-2-cyano-2-(9H-fluoren-2-ylcarbamoyl)-vinyl]-indol-1-yl}-acetic acid;
{3-[(E)-2-cyano-2-(4-propyl-phenylcarbamoyl)-vinyl]-indol-1-yl}-acetic acid;
{3-[(E)-2-(biphenyl-4-ylcarbamoyl)-2-cyano-vinyl]-indol-1-yl}-acetic acid;
{3-[(E)-2-cyano-2-(3,2'-dimethyl-biphenyl-4-ylcarbamoyl)-vinyl]-indol-1-yl}-acetic acid;
{3-[(E)-2-(4-tert-butyl-phenylcarbamoyl)-2-cyano-vinyl]-indol-1-yl}-acetic acid;
{3-[(E)-2-(2-benzyl-phenylcarbamoyl)-2-cyano-vinyl]-indol-1-yl}-acetic acid;
{3-[(E)-2-(4-butyl-phenylcarbamoyl)-2-cyano-vinyl]-indol-1-yl}-acetic acid;
{3-[(E)-2-(2-acetyl-phenylcarbamoyl)-2-cyano-vinyl]-indol-1-yl}-acetic acid;
{3-[(E)-2-cyano-2-(indan-5-ylcarbamoyl)-vinyl]-indol-1-yl}-acetic acid;
{3-[(E)-2-(4-sec-butyl-phenylcarbamoyl)-2-cyano-vinyl]-indol-1-yl}-acetic acid;
{3-[(E)-2-cyano-2-(2-propyl-phenylcarbamoyl)-vinyl]-indol-1-yl}-acetic acid;
{3-[(E)-2-cyano-2-(3-phenoxy-phenylcarbamoyl)-vinyl]-indol-1-yl}-acetic acid;
{3-[(E)-2-cyano-2-(3-ethyl-phenylcarbamoyl)-vinyl]-indol-1-yl}-acetic acid;
{3-[(E)-2-cyano-2-(2-ethoxy-phenylcarbamoyl)-vinyl]-indol-1-yl}-acetic acid;
{3-[(E)-2-(3-benzyloxy-phenylcarbamoyl)-2-cyano-vinyl]-indol-1-yl}-acetic acid;
{3-[(E)-2-cyano-2-(4-iodo-phenylcarbamoyl)-vinyl]-indol-1-yl}-acetic acid;
{3-[(E)-2-cyano-2-(3-iodo-phenylcarbamoyl)-vinyl]-indol-1-yl}-acetic acid;
(3-{(E)-2-cyano-2-[(4-fluoro-phenyl)-methyl-carbamoyl]-vinyl}-indol-1-yl)-acetic acid;
(3-{(E)-2-cyano-2-[(4-methoxy-phenyl)-methyl-carbamoyl]-vinyl}-indol-1-yl)-acetic acid;
{3-[(E)-2-cyano-2-(methyl-phenyl-carbamoyl)-vinyl]-indol-1-yl}-acetic acid;
{3-[(E)-2-cyano-3-(3,4-dihydro-2H-quinolin-1-yl)-3-oxo-propenyl]-indol-1-yl}-acetic acid;
{3-[(E)-2-cyano-2-(methyl-p-tolyl-carbamoyl)-vinyl]-indol-1-yl}-acetic acid;
(3-{(E)-2-cyano-2-[2-(2,4-dichloro-phenoxy)-phenylcarbamoyl]-vinyl}-indol-1-yl)-acetic acid;
{3-[(E)-2-cyano-2-(2,5-dimethyl-phenylcarbamoyl)-vinyl]-indol-1-yl}-acetic acid;
{3-[(E)-2-cyano-2-(9-ethyl-9H-carbazol-3-ylcarbamoyl)-vinyl]-indol-1-yl}-acetic acid;
{3-[(E)-2-(3,5-bis-trifluoromethyl-phenylcarbamoyl)-2-cyano-vinyl]-indol-1-yl}-acetic acid;
{3-[(E)-2-cyano-2-(5-methoxy-2-methyl-phenylcarbamoyl)-vinyl]-indol-1-yl}-acetic acid;
{3-[(E)-2-(3-benzoyl-phenylcarbamoyl)-2-cyano-vinyl]-indol-1-yl}-acetic acid;
{3-[(E)-2-(4-benzyloxy-phenylcarbamoyl)-2-cyano-vinyl]-indol-1-yl}-acetic acid;
{3-[(E)-2-cyano-2-(3-nitro-phenylcarbamoyl)-vinyl]-indol-1-yl}-acetic acid;
{3-[(E)-2-cyano-2-(9-oxo-9H-fluoren-2-ylcarbamoyl)-vinyl]-indol-1-yl}-acetic acid;
{3-[(E)-2-cyano-2-(4-methoxy-biphenyl-3-ylcarbamoyl)-vinyl]-indol-1-yl}-acetic acid;
{3-[(E)-2-cyano-2-(2-methoxy-dibenzofuran-3-ylcarbamoyl)-vinyl]-indol-1-yl}-acetic acid;
{3-[(E)-2-cyano-2-(9-oxo-9H-fluoren-4-ylcarbamoyl)-vinyl]-indol-1-yl}-acetic acid;
{3-[(E)-2-cyano-2-(9-oxo-9H-fluoren-1-ylcarbamoyl)-vinyl]-indol-1-yl}-acetic acid;
{3-[(E)-2-(2-benzoyl-phenylcarbamoyl)-2-cyano-vinyl]-indol-1-yl}-acetic acid;
{3-[(E)-2-(3-chloro-4-methoxy-phenylcarbamoyl)-2-cyano-vinyl]-indol-1-yl}-acetic acid;
{3-[(E)-2-(5-chloro-2-methoxy-phenylcarbamoyl)-2-cyano-vinyl]-indol-1-yl}-acetic acid;
3-[(E)-3-(1-carboxymethyl-1H-indol-3-yl)-2-cyano-acryloylamino]-4-methyl-benzoic acid methyl ester;
2-[(E)-3-(1-carboxymethyl-1H-indol-3-yl)-2-cyano-acryloylamino]-benzoic acid methyl ester;
{3-[(E)-2-cyano-2-(4-trifluoromethoxy-phenylcarbamoyl)-vinyl]-indol-1-yl}-acetic acid;
{3-[(E)-2-cyano-2-(3,5-dimethyl-phenylcarbamoyl)-vinyl]-indol-1-yl}-acetic acid;
{3-[(E)-2-(3-bromo-4-methyl-phenylcarbamoyl)-2-cyano-vinyl]-indol-1-yl}-acetic acid;
{3-[(E)-2-(4-bromo-3-methyl-phenylcarbamoyl)-2-cyano-vinyl]-indol-1-yl}-acetic acid;
4-[(E)-3-(1-carboxymethyl-1H-indol-3-yl)-2-cyano-acryloylamino]-benzoic acid ethyl ester;
3-[(E)-3-(1-carboxymethyl-1H-indol-3-yl)-2-cyano-acryloylamino]-benzoic acid methyl ester;
{3-[(E)-2-cyano-2-(4-trifluoromethyl-phenylcarbamoyl)-vinyl]-indol-1-yl}-acetic acid;
{3-[(E)-2-cyano-2-(3,5-dimethoxy-phenylcarbamoyl)-vinyl]-indol-1-yl}-acetic acid;
{3-[(E)-2-(4-bromo-3-chloro-phenylcarbamoyl)-2-cyano-vinyl]-indol-1-yl}-acetic acid;
{3-[(E)-2-(4-bromo-2-methyl-phenylcarbamoyl)-2-cyano-vinyl]-indol-1-yl}-acetic acid;
{3-[(E)-2-(4-acetyl-phenylcarbamoyl)-2-cyano-vinyl]-indol-1-yl}-acetic acid;
{3-[(E)-2-(2-bromo-4-methyl-phenylcarbamoyl)-2-cyano-vinyl]-indol-1-yl}-acetic acid;
{3-[(E)-2-(benzo[1,3]dioxol-5-ylcarbamoyl)-2-cyano-vinyl]-indol-1-yl}-acetic acid;
{3-[(E)-2-cyano-2-(phenethyl-phenyl-carbamoyl)-vinyl]-indol-1-yl}-acetic acid;
{3-[(E)-2-cyano-3-(11,12-dihydro-6H-dibenzo[b,f]azocin-5-yl)-3-oxo-propenyl]-indol-1-yl}-acetic acid;
[3-((E)-2-cyano-2-diphenylcarbamoyl-vinyl)-indol-1-yl]-acetic acid;

[3-((E)-2-cyano-3-dibenzo[b,f]azepin-5-yl-3-oxo-propenyl)-indol-1-yl]-acetic acid;
(3-{(E)-2-[(4-chloro-phenyl)-methyl-carbamoyl]-2-cyano-vinyl}-indol-1-yl)-acetic acid;
{3-[(E)-2-cyano-3-(6,11-dihydro-dibenzo[b,e]azepin-5-yl)-3-oxo-propenyl]-indol-1-yl}-acetic acid;
[3-((E)-2-cyano-2-diphenethylcarbamoyl-vinyl)-indol-1-yl]-acetic acid;
{3-[(E)-2-cyano-3-(10,11-dihydro-dibenzo[b,f]azepin-5-yl)-3-oxo-propenyl]-indol-1-yl}-acetic acid;
(3-{(E)-2-cyano-2-[methyl-((R)-1-phenyl-ethyl)-carbamoyl]-vinyl}-indol-1-yl)-acetic acid;
{3-[(E)-2-(benzyl-methyl-carbamoyl)-2-cyano-vinyl]-indol-1-yl}-acetic acid;
(3-{(E)-2-[(4-acetyl-phenyl)-methyl-carbamoyl]-2-cyano-vinyl}-indol-1-yl)-acetic acid;
(3-{(E)-2-[(4-acetyl-phenyl)-furan-2-ylmethyl-carbamoyl]-2-cyano-vinyl}-indol-1-yl)-acetic acid;
{3-[(E)-2-(benzyl-carboxymethyl-carbamoyl)-2-cyano-vinyl]-indol-1-yl}-acetic acid;
3-{benzyl-[(E)-3-(1-carboxymethyl-1H-indol-3-yl)-2-cyano-acryloyl]-amino}-propionic acid;
{3-[(E)-2-cyano-3-(2,3-dihydro-indol-1-yl)-3-oxo-propenyl]-indol-1-yl}-acetic acid;
{3-[(E)-2-(carboxymethyl-phenyl-carbamoyl)-2-cyano-vinyl]-indol-1-yl}-acetic acid;
(3-{(E)-2-[(2-cyano-ethyl)-phenyl-carbamoyl]-vinyl}-indol-1-yl)-acetic acid;
(3-{(E)-2-[(3-chloro-phenyl)-methyl-carbamoyl]-2-cyano-vinyl}-indol-1-yl)-acetic acid;
{3-[(E)-2-(allyl-phenyl-carbamoyl)-2-cyano-vinyl]-indol-1-yl}-acetic acid;
{3-[(E)-2-cyano-2-(cyclohexyl-phenyl-carbamoyl)-vinyl]-indol-1-yl}-acetic acid;
{3-[(E)-2-cyano-2-(methyl-o-tolyl-carbamoyl)-vinyl]-indol-1-yl}-acetic acid;
{3-[(E)-2-cyano-2-(ethyl-phenyl-carbamoyl)-vinyl]-indol-1-yl}-acetic acid;
{3-[(E)-2-cyano-2-(butyl-phenyl-carbamoyl)-vinyl]-indol-1-yl}-acetic acid;
[5-bromo-3-((E)-2-cyano-2-phenylcarbamoyl-vinyl)-indol-1-yl]-acetic acid;
[3-((E)-2-cyano-2-phenylcarbamoyl-vinyl)-5-fluoro-indol-1-yl]-acetic acid;
[3-((E)-2-cyano-2-phenylcarbamoyl-vinyl)-5-methyl-indol-1-yl]-acetic acid;
[3-((E)-2-cyano-2-phenylcarbamoyl-vinyl)-6-fluoro-indol-1-yl]-acetic acid;
[3-((E)-2-cyano-2-phenylcarbamoyl-vinyl)-6-nitro-indol-1-yl]-acetic acid;
[3-((E)-2-cyano-2-phenylcarbamoyl-vinyl)-7-methyl-indol-1-yl]-acetic acid;
{3-[(E)-3-(2-chloro-phenothiazin-10-yl)-2-cyano-3-oxo-propenyl]-indol-1-yl}-acetic acid;
{3-[(E)-2-cyano-2-(phenyl-thiophen-3-ylmethyl-carbamoyl)-vinyl]-indol-1-yl}-acetic acid;
(3-{(E)-2-cyano-2-[(2,2-diphenyl-ethyl)-phenyl-carbamoyl]-vinyl}-indol-1-yl)-acetic acid;
(3-{(E)-2-cyano-2-[phenyl-(3-phenyl-propyl)-carbamoyl]-vinyl}-indol-1-yl)-acetic acid;
[3-((E)-2-cyano-2-{[2-(4-fluoro-phenyl)-ethyl]-phenyl-carbamoyl}-vinyl)-indol-1-yl]-acetic acid;
{3-[(E)-2-cyano-3-(11H-10-oxa-5-aza-dibenzo[a,d]cyclohepten-5-yl)-3-oxo-propenyl]-indol-1-yl}-acetic acid;
{3-[(E)-2-cyano-2-(isopropyl-phenyl-carbamoyl)-vinyl]-indol-1-yl}-acetic acid;
(3-{(E)-2-cyano-2-[(3,4-dichloro-phenyl)-methyl-carbamoyl]-vinyl}-indol-1-yl)-acetic acid;
(3-{(E)-2-cyano-2-[ethyl-(4-trifluoromethoxy-phenyl)-carbamoyl]-vinyl}-indol-1-yl)-acetic acid;
{3-[(E)-2-(benzhydryl-carbamoyl)-2-cyano-vinyl]-indol-1-yl}-acetic acid;
(3-{(E)-2-cyano-2-[methyl-(2-trifluoromethoxy-phenyl)-carbamoyl]-vinyl}-indol-1-yl)-acetic acid;
{3-[(E)-2-cyano-2-(2,4-difluoro-phenylcarbamoyl)-vinyl]-indol-1-yl}-acetic acid;
(3-{(E)-2-cyano-2-[methyl-(4-trifluoromethoxy-phenyl)-carbamoyl]-vinyl}-indol-1-yl)-acetic acid;
{3-[(E)-2-cyano-2-(ethyl-naphthalen-1-yl-carbamoyl)-vinyl]-indol-1-yl}-acetic acid;
(3-{(E)-2-cyano-2-[(2,4-difluoro-phenyl)-methyl-carbamoyl]-vinyl}-indol-1-yl)-acetic acid;
{3-[(E)-2-cyano-2-(2,4,6-trifluoro-phenylcarbamoyl)-vinyl]-indol-1-yl}-acetic acid;
{3-[(E)-2-cyano-2-(2,3,4-trifluoro-phenylcarbamoyl)-vinyl]-indol-1-yl}-acetic acid;
{3-[(E)-2-cyano-3-(3,4-dihydro-1H-isoquinolin-2-yl)-3-oxo-propenyl]-indol-1-yl}-acetic acid;
{3-[(E)-2-cyano-3-oxo-3-(7-trifluoromethyl-3,4-dihydro-2H-quinolin-1-yl)-propenyl]-indol-1-yl}-acetic acid;
(3-{(E)-2-cyano-2-[(3-fluoro-phenyl)-methyl-carbamoyl]-vinyl}-indol-1-yl)-acetic acid;
[3-((E)-2-cyano-3-dibenzo[b,f]azepin-5-yl-3-oxo-propenyl)-5-fluoro-indol-1-yl]-acetic acid;
{3-[(E)-2-cyano-3-(6,11-dihydro-dibenzo[b,e]azepin-5-yl)-3-oxo-propenyl]-5-fluoro-indol-1-yl}-acetic acid;
{3-[(E)-2-(benzyl-phenyl-carbamoyl)-2-cyano-vinyl]-5-fluoro-indol-1-yl}-acetic acid;
{3-[(E)-2-cyano-2-(cyclohexyl-phenyl-carbamoyl)-vinyl]-5-fluoro-indol-1-yl}-acetic acid;
{3-[(E)-2-(butyl-phenyl-carbamoyl)-2-cyano-vinyl]-5-fluoro-indol-1-yl}-acetic acid;
(3-{(E)-2-cyano-2-[(4-fluoro-phenyl)-methyl-carbamoyl]-vinyl}-5-fluoro-indol-1-yl)-acetic acid;
(3-{(E)-2-cyano-2-[(3-fluoro-phenyl)-methyl-carbamoyl]-vinyl}-5-fluoro-indol-1-yl)-acetic acid;
(3-{(E)-2-cyano-2-[(3,4-dichloro-phenyl)-methyl-carbamoyl]-vinyl}-5-fluoro-indol-1-yl)-acetic acid;
(3-{(E)-2-cyano-2-[methyl-(2-trifluoromethyl-phenyl)-carbamoyl]-vinyl}-5-fluoro-indol-1-yl)-acetic acid;
(3-{(E)-2-cyano-2-[(2,4-difluoro-phenyl)-methyl-carbamoyl]-vinyl}-5-fluoro-indol-1-yl)-acetic acid;
{3-[(E)-2-cyano-2-(phenyl-thiophen-3-ylmethyl-carbamoyl)-vinyl]-5-fluoro-indol-1-yl}-acetic acid;
{3-[(E)-2-cyano-3-oxo-3-(7-trifluoromethyl-3,4-dihydro-2H-quinolin-1-yl)-propenyl]-5-fluoro-indol-1-yl}-acetic acid;
(3-{(E)-2-cyano-2-[ethyl-(4-trifluoromethoxy-phenyl)-carbamoyl]-vinyl}-5-fluoro-indol-1-yl)-acetic acid;
{3-[(E)-2-cyano-3-(3,4-dihydro-1H-isoquinolin-2-yl)-3-oxo-propenyl]-5-fluoro-indol-1-yl}-acetic acid;
{3-[(E)-2-cyano-2-(phenethyl-phenyl-carbamoyl)-vinyl]-5-fluoro-indol-1-yl}-acetic acid;
[3-((E)-2-cyano-3-dibenzo[b,f]azepin-5-yl-3-oxo-propenyl)-6-methyl-indol-1-yl]-acetic acid;
{3-[(E)-2-cyano-3-(6,11-dihydro-dibenzo[b,e]azepin-5-yl)-3-oxo-propenyl]-6-methyl-indol-1-yl}-acetic acid;
{3-[(E)-2-cyano-3-(10,11-dihydro-dibenzo[b,f]azepin-5-yl)-3-oxo-propenyl]-6-methyl-indol-1-yl}-acetic acid;
{3-[(E)-2-(benzyl-phenyl-carbamoyl)-2-cyano-vinyl]-6-methyl-indol-1-yl}-acetic acid;
{3-[(E)-2-cyano-2-(cyclohexyl-phenyl-carbamoyl)-vinyl]-6-methyl-indol-1-yl}-acetic acid;

(3-{(E)-2-cyano-2-[(4-fluoro-phenyl)-methyl-carbamoyl]-vinyl}-6-methyl-indol-1-yl)-acetic acid;
{3-[(E)-2-(butyl-phenyl-carbamoyl)-2-cyano-vinyl]-6-methyl-indol-1-yl}-acetic acid;
{3-[(E)-2-cyano-2-(cyclohexyl-phenyl-carbamoyl)-vinyl]-7-methyl-indol-1-yl}-acetic acid; and
(3-{(E)-2-cyano-2-[(4-fluoro-phenyl)-methyl-carbamoyl]-vinyl}-7-methyl-indol-1-yl)-acetic acid.

The present invention therefore also relates to compounds of general Formula $I_{C1}$

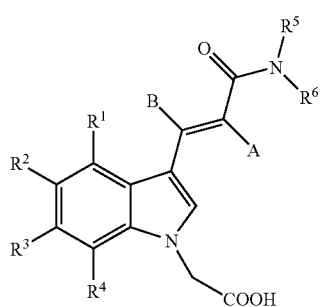

wherein
A represents hydrogen; alkyl; halogen or cyano;
B represents hydrogen; alkyl or halogen;
$R^1$, $R^2$, $R^3$ and $R^4$ independently represent hydrogen; alkyl; halogen; nitro; cyano or formyl (and preferably independently represent hydrogen, alkyl, halogen or nitro);
$R^5$ and $R^6$ independently represent hydrogen; alkyl; cycloalkyl; cycloalkyl-alkyl; heteroaryl; heteroaryl-alkyl; alkenyl; carboxyalkyl; cyanoalkyl; diphenylalkyl; aryl, arylalkoxy-aryl, aryl-alkyl, aryl-alkyl-aryl, arylcarbonyl-aryl or aryloxy-aryl, or $R^5$ and $R^6$, together with the nitrogen atom to which they are attached, form a heterocyclic ring system;
with the exception however of the following compounds:
{3-[(E)-2-cyano-2-(4-fluoro-phenylcarbamoyl)-vinyl]-indol-1-yl}-acetic acid;
[3-((E)-2-cyano-2-m-tolylcarbamoyl-vinyl)-indol-1-yl]-acetic acid;
{3-[(E)-2-(3-bromo-phenylcarbamoyl)-2-cyano-vinyl]-indol-1-yl}-acetic acid;
[3-((E)-2-cyano-2-phenylcarbamoyl-vinyl)-indol-1-yl]-acetic acid;
[3-((E)-2-benzylcarbamoyl-2-cyano-vinyl)-indol-1-yl]-acetic acid;
[3-((E)-2-cyano-2-o-tolylcarbamoyl-vinyl)-indol-1-yl]-acetic acid;
[3-((E)-2-cyano-2-p-tolylcarbamoyl-vinyl)-indol-1-yl]-acetic acid;
{3-[(E)-2-(4-bromo-phenylcarbamoyl)-2-cyano-vinyl]-indol-1-yl}-acetic acid;
{3-[(E)-2-cyano-2-(4-ethyl-phenylcarbamoyl)-vinyl]-indol-1-yl}-acetic acid;
{3-[(E)-2-cyano-2-(4-methoxy-phenylcarbamoyl)-vinyl]-indol-1-yl}-acetic acid;
{3-[(E)-2-cyano-2-(4-ethoxy-phenylcarbamoyl)-vinyl]-indol-1-yl}-acetic acid;
[3-((E)-2-cyano-2-isopropylcarbamoyl-vinyl)-indol-1-yl]-acetic acid;
{3-[(E)-2-cyano-2-(3-ethoxy-phenylcarbamoyl)-vinyl]-indol-1-yl}-acetic acid;
{3-[(E)-2-cyano-3-[[2-(1H-indol-3-yl)ethyl]amino]-3-oxo-1-propenyl]-indol-1-yl}-acetic acid;
{3-[(E)-2-cyano-2-(4-chloro-phenylcarbamoyl)-vinyl]-indol-1-yl}-acetic acid;
{3-[(E)-2-cyano-3-(4-methyl-piperidin-1-yl)-3-oxo-propenyl]-indol-1-yl}-acetic acid;
{3-[(E)-2-(3-chloro-4-methyl-phenylcarbamoyl)-2-cyano-vinyl]-indol-1-yl}-acetic acid;
{3-[(E)-2-cyano-2-(3-phenyl-propylcarbamoyl)-vinyl]-indol-1-yl}-acetic acid;
{3-[(E)-2-cyano-2-(2,3-dichloro-phenylcarbamoyl)-vinyl]-indol-1-yl}-acetic acid;
{3-[(E)-2-cyano-2-(5-chloro-2-methyl-phenylcarbamoyl)-vinyl]-indol-1-yl}-acetic acid;
{3-[(E)-2-cyano-2-(4-methoxy-benzylcarbamoyl)-vinyl]-indol-1-yl}-acetic acid;
{3-[(E)-2-cyano-2-(2-fluoro-phenylcarbamoyl)-vinyl]-indol-1-yl}-acetic acid; and
{3-[(E)-2-cyano-3-oxo-3-(4-phenyl-piperazin-1-yl)-propenyl]-indol-1-yl}-acetic acid.

The invention further relates to compounds of general Formula $I_{C2}$ wherein

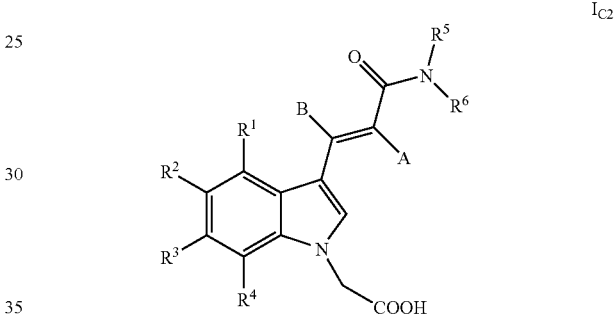

wherein
A represents hydrogen; alkyl; halogen or cyano;
B represents hydrogen; alkyl or halogen;
$R^1$, $R^2$, $R^3$ and $R^4$ independently represent hydrogen; alkyl; halogen; nitro; cyano or formyl (and preferably independently represent hydrogen, alkyl, halogen or nitro);
$R^5$ and $R^6$ independently represent hydrogen; alkyl; cycloalkyl; cycloalkyl-alkyl; heteroaryl; heteroaryl-alkyl; alkenyl; carboxyalkyl; cyanoalkyl; diphenylalkyl; aryl, arylalkoxy-aryl, aryl-alkyl, aryl-alkyl-aryl, arylcarbonyl-aryl or aryloxy-aryl,
or $R^5$ and $R^6$, together with the nitrogen atom to which they are attached, form a heterocyclic ring system;
it being understood however that at least one of the following conditions must be met:
one of $R^1$, $R^2$, $R^3$ and $R^4$ is different from a hydrogen atom; or
when $R^5$ and $R^6$ are such that they do not form a heterocyclic ring system together with the nitrogen atom to which they are attached, then both $R^5$ and $R^6$ are different from hydrogen and one of $R^5$ and $R^6$ is different from alkyl; or
when $R^5$ and $R^6$ are such that they form a heterocyclic ring system together with the nitrogen atom to which they are attached, then said heterocyclic ring system is neither an unsubstituted or substituted piperidine nor an unsubstituted or substituted piperazine.

The invention also relates to the compounds of general formula $I_{C1}$ for use as medicaments as well as to the compounds of general formula $I_{C2}$ as medicaments.

A further aspect of the invention relates to pharmaceutical compositions containing, as active principle, at least one compound of general formula I, and a pharmaceutically acceptable carrier. The invention also encompasses pharmaceutical compositions containing, as active principle, at least one compound of general formula $I_{C1}$, and a pharmaceutically acceptable carrier as well as pharmaceutical compositions containing, as active principle, at least one compound of general formula $I_{C2}$, and a pharmaceutically acceptable carrier.

The invention also relates to the use of a compound of general formula I for the preparation of a medicament intended for the prevention and treatment of chromic and acute allergic immune disorders comprising allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases comprising Churg-Strauss syndrome and sinusitis, basophil-related diseases, comprising basophilic leukemia and basophilic leukocytosis. The invention further relates to the use of a compound of general formula $I_{C1}$ or of a compound of general formula $I_{C2}$ for the preparation of a medicament intended for the prevention and treatment of the aforementioned diseases. The medicaments thus prepared can be intended for humans or for other mammals.

The invention also relates to methods of preventing and treating in humans diseases selected from chronic and acute allergic immune disorders comprising allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases comprising Churg-Strauss syndrome and sinusitis, basophil-related diseases, comprising basophilic leukemia and basophilic leukocytosis, said methods comprising the administration to humans in need thereof of an effective amount of a compound of general formula I. The invention further relates to methods of preventing and treating in humans the same diseases, said methods comprising the administration to humans in need thereof of an effective amount of a compound of general formula $I_{C1}$ or of a compound of general formula $I_{C2}$.

The preferences indicated for the compounds of general formula I are applicable mutatis mutandis the compounds of general formula $I_{C1}$ and to the compounds of general formula $I_{C2}$.

Besides, a particular variant of the invention relates, in its first aspect, to pharmaceutical compositions containing at least one compound of the general Formula $I_P$

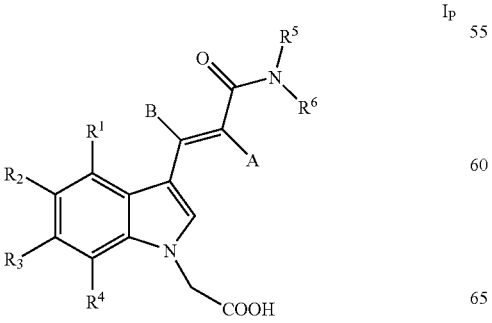

$I_P$ wherein

A represents hydrogen; alkyl; halogen or cyano;

B represents hydrogen; alkyl or halogen;

$R^1$, $R^2$, $R^3$ and $R^4$ independently represent hydrogen; alkyl; halogen; nitro; cyano or formyl;

$R^5$ and $R^6$ independently represent hydrogen; alkyl; alkenyl; cycloalkyl; heteroaryl; or a member selected from the group consisting of aryl, alkoxy-aryl, alkoxycarbonyl-aryl, alkylcarbonyl-aryl, aryl-alkoxy-aryl, aryl-alkyl, aryl-alkyl-aryl, arylcarbonyl-aryl and aryloxy-aryl, wherein the aryl group is unsubstituted or mono- or di-substituted substituted with substituent(s) independently selected from the group consisting of alkyl, alkoxy, halogen, cyano, alkoxycarbonyl, alkylcarbonyl, phenyl, benzyl, benzoyl, benzyloxy, benzyloxycarbonyl, trifluoromethyl and trifluoromethoxy;

or $R^5$ and $R^6$, together with the nitrogen atom to which they are attached, form a heterocyclic ring system;

and optically pure enantiomers, mixtures of enantiomers, racemates, optically pure diastereoisomers, mixtures of diastereoisomers, diastereoisomeric racemates, mixture of diastereoisomeric racemates, meso forms, geometric isomers, prodrugs of compounds in which a prodrug forming group is present, as well as solvates and morphological forms, pharmaceutically acceptable salts thereof and usual inert carrier materials or adjuvants; it being understood however that in general Formula $I_P$:

i) the term "alkyl" or "lower alkyl", used alone or in any combination, refers to a saturated aliphatic group including a straight or branched hydrocarbon chain containing 1-8 carbon atoms (and preferably 1-4 carbon atoms), which saturated aliphatic group can be optionally substituted with one or more substituents, each independently selected from alkenyl, alkoxy, alkoxycarbonyl, alkylcarbonyl, alkylcarbonyloxy, alkylendioxy, alkylsulfinyl, alkylsulfonyl, alkylthio, alkynyl, amino, aminocarbonyl, aryl, arylalkenyl, arylalkyloxy, aryloxy, aryloxycarbonyl, arylsulfinyl, arylsulfonyl, arylthio, carboxy, cyano, formyl, halogen, haloalkoxy, heterocyclyl, hydroxy, mercapto, nitro, and the like, appended to any carbon atom of the alkyl moiety;

ii) the term "alkenyl" or "lower alkenyl", used alone or in any combination, refers to a straight or branched hydrocarbon chain containing 2-8 carbon atoms with at least one carbon-carbon double bond ($R_aR_bC=CR_cR_d$ wherein $R_a-R_d$ refer to substituents, each individually and independently selected from hydrogen and alkyl, alkoxy, alkoxyalkyl and the like);

iii) the term "alkoxy", used alone or in any combination, refers to an alkyl group appended to the parent molecular moiety through an oxygen bridge;

iv) the term "aryl", used alone or in any combination, refers to an carbocyclic group having at least one aromatic ring, e.g. phenyl or biphenyl, or multiple condensed ring systems, in which at least one ring is aromatic (e.g. 1,2,3,4-tetrahydronaphthyl, naphthyl, anthryl, phenanthryl, fluorenyl, and the like), which aryl group may be optionally substituted with one or more functional groups individually and independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylendioxy, alkylsulfinyl, alkylsulfinylalkyl, alkylsulfonyl, alkylsulfonylalkyl, alkylthio, alkylthioalkyl, alkynyl, amino, aminoalkyl, aminocarbonyl, aminocarbonylalkyl, aryl, arylalkenyl, arylalkyloxy, arylalkyl, aryloxy, aryloxycarbonyl, aryloxycarbonylalkyl, arylsulfinyl, arylsulfinylalkyl, arylsulfonyl, arylsulfonylalkyl, arylthio, arylthioalkyl, carboxy, carboxyalkyl, cyano, cyanoalkyl, formyl, formylalkyl, halogen, haloalkoxy, haloalkyl, heteroaryl, heterocyclyl, hydroxy, hydroxyalkyl, mercapto, nitro, and the like;

v) the term "arylalkoxy", used alone or in any combination, refers to an aryl group which may be unsubstituted or substituted as previously defined and which is appended to the parent molecular moiety through an alkoxy group;

vi) the term "arylalkyl", used alone or in any combination, refers to an aryl group which may be unsubstituted or substituted as previously defined and which is appended to the parent molecular moiety through an alkyl group;

vii) the term "aryloxy", used alone or in any combination, refers to an aryl group which may be unsubstituted or substituted as previously defined and which is appended to the parent molecular moiety through an oxygen bridge;

viii) the term "arylcarbonyl" or "aroyl", used alone or in any combination, refers to an aryl group appended to the parent molecular moiety through a carbonyl group;

ix) the term "cycloalkyl", used alone or in any combination, refers to a saturated cyclic hydrocarbon moiety containing 3-15 carbon atoms, optionally substituted with one or more groups, each individually and independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylendioxy, alkylsulfinyl, alkylsulfinylalkyl, alkylsulfonyl, alkylsulfonylalkyl, alkylthio, alkylthioalkyl, alkynyl, amino, aminoalkyl, aminocarbonyl, aminocarbonylalkyl, aryl, arylalkenyl, arylalkyloxy, arylalkyl, aryloxy, aryloxycarbonyl, aryloxycarbonylalkyl, arylsulfinyl, arylsulfinylalkyl, arylsulfonyl, arylsulfonylalkyl, arylthio, arylthioalkyl, carboxy, carboxyalkyl, cyano, cyanoalkyl, formyl, formylalkyl, halogen, haloalkoxy, haloalkyl, heterocyclyl, hydroxy, hydroxyalkyl, mercapto, nitro, and the like, it being understood that polycyclic cycloalkyl groups one of the distal rings may be aromatic (e.g., 1-indanyl, 2-indanyl, tetrahydronaphthalene, and the like);

x) the term "heterocyclyl" alone or in any combination, refers to a monocyclic, bicyclic or polycyclic ring system containing up to 15 ring atoms, at least one of these being a hetero atom independently selected from nitrogen, oxygen or sulfur, which ring system may be saturated, partially unsaturated, unsaturated or aromatic and may be optionally substituted with one or more groups, each individually and independently selected from alkenyl, alkoxy, alkoxyalkyl, alkoxycarbonyl, alkoxycarbonylalkyl, alkyl, alkylcarbonyl, alkylcarbonylalkyl, alkylcarbonyloxy, alkylendioxy, alkylsulfinyl, alkylsulfinylalkyl, alkylsulfonyl, alkylsulfonylalkyl, alkylthio, alkylthioalkyl, alkynyl, amino, aminoalkyl, aminocarbonyl, aminocarbonylalkyl, aryl, arylalkenyl, arylalkyloxy, arylalkyl, aryloxy, aryloxycarbonyl, aryloxycarbonylalkyl, arylsulfinyl, arylsulfinylalkyl, arylsulfonyl, arylsulfonylalkyl, arylthio, arylthioalkyl, carboxy, carboxyalkyl, cyano, cyanoalkyl, cycloalkyl, formyl, formylalkyl, halogen, haloalkoxy, haloalkyl, heterocyclyl, heteroaryl, hydroxy, hydroxyalkyl, mercapto, nitro, and the like;

xi) the term "heteroaryl", used alone or in any combination, is a special case of heterocyclyl and refers to a mono- or bicyclic or polycyclic aromatic ring system, in which at least one heterocyclic ring is aromatic.

Compounds of the above general Formula $I_P$ are novel, with the exception of the following compounds which, however, are also potent CRTH2 receptor antagonists and were not previously described in this respect in the literature:

{3-[(E)-2-cyano-2-(4-fluoro-phenylcarbamoyl)-vinyl]-indol-1-yl}-acetic acid;

[3-((E)-2-cyano-2-m-tolylcarbamoyl-vinyl)-indol-1-yl]-acetic acid;

{3-[(E)-2-(3-bromo-phenylcarbamoyl)-2-cyano-vinyl]-indol-1-yl}-acetic acid;

[3-((E)-2-cyano-2-phenylcarbamoyl-vinyl)-indol-1-yl]-acetic acid;

[3-((E)-2-benzylcarbamoyl-2-cyano-vinyl)-indol-1-yl]-acetic acid;

[3-((E)-2-cyano-2-o-tolylcarbamoyl-vinyl)-indol-1-yl]-acetic acid;

[3-((E)-2-cyano-2-p-tolylcarbamoyl-vinyl)-indol-1-yl]-acetic acid;

{3-[(E)-2-(4-bromo-phenylcarbamoyl)-2-cyano-vinyl]-indol-1-yl}-acetic acid;

{3-[(E)-2-cyano-2-(4-ethyl-phenylcarbamoyl)-vinyl]-indol-1-yl}-acetic acid;

{3-[(E)-2-cyano-2-(4-methoxy-phenylcarbamoyl)-vinyl]-indol-1-yl}-acetic acid;

{3-[(E)-2-cyano-2-(4-ethoxy-phenylcarbamoyl)-vinyl]-indol-1-yl}-acetic acid;

[3-((E)-2-cyano-2-isopropylcarbamoyl-vinyl)-indol-1-yl]-acetic acid;

{3-[(E)-2-cyano-2-(3-ethoxy-phenylcarbamoyl)-vinyl]-indol-1-yl}-acetic acid;

{3-[(E)-2-cyano-3-[[2-(1H-indol-3-yl)ethyl]amino]-3-oxo-1-propenyl]-indol-1-yl}-acetic acid;

{3-[(E)-2-cyano-2-(4-chloro-phenylcarbamoyl)-vinyl]-indol-1-yl}-acetic acid.

A second aspect of the abovementioned particular variant of the invention is the use of compounds of the general Formula $I_P$ as medicaments to treat the aforementioned diseases.

A third aspect of the abovementioned particular variant of the invention relates to the novel compounds of the general Formula $II_P$

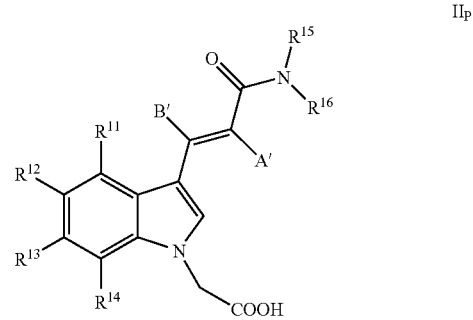

wherein

A' represents hydrogen; lower alkyl; halogen or cyano;

B' represents hydrogen; lower alkyl or halogen;

$R^{11}$, $R^{12}$, $R^{13}$ and $R^{14}$ independently represent hydrogen; lower alkyl; halogen; nitro; cyano or formyl;

$R^{15}$ and $R^{16}$ independently represent hydrogen; lower alkyl; lower alkenyl; aryl; lower alkoxy-aryl; lower alkoxycarbonyl-aryl; lower alkylcarbonyl-aryl; aryl-lower alkoxy-aryl; aryl-lower alkyl; aryl-lower alkyl-aryl; arylcarbonyl-aryl;

aryloxy-aryl; whereby the aryl group is unsubstituted or mono- or di-substituted with lower alkyl, lower alkoxy, halogen, cyano, lower alkoxycarbonyl, lower alkylcarbonyl, phenyl, benzyl, benzoyl, benzyloxy, benzyloxycarbonyl, trifluormethyl or trifluormethoxy; cycloalkyl or heteroaryl;

$R^{15}$ and $R^{16}$, together with the nitrogen atom to which they are attached, form a heterocyclic ring system;

and optically pure enantiomers, mixtures of enantiomers, racemates, optically pure diastereoisomers, mixtures of diastereoisomers, diastereoisomeric racemates, mixture of diastereoisomeric racemates, meso forms, geometric isomers, prodrugs of compounds in which a prodrug forming group is present, as well as solvates and morphological forms and pharmaceutically acceptable salts thereof;

with the proviso that the substituents $R^{11}$, $R^{12}$, $R^{13}$, $R^{14}$, $R^{15}$ and $R^{16}$ all at the same time do not represent hydrogen or in addition and in case either one of the substituents $R^{15}$ or $R^{16}$ represents hydrogen and the other aryl then the aryl group is not an unsubstituted indol-3-yl-ethyl, benzyl, or phenyl group, and also not a $C_1$-$C_3$ alkyl, $C_1$-$C_2$ alkoxy or halogen mono-substituted phenyl group, or $R^{15}$ and $R^{16}$ together with the nitrogen atom to which they are attached do not form a phenyl substituted piperazine ring;

it being understood however that in general Formula $II_P$, the same definitions i) to xi) apply as those given for general Formula $I_P$.

A fourth aspect of the abovementioned particular variant of the invention thus relates to these novel compounds per se as well as to their use as pharmaceutically active ingredients. A fifth aspect of the abovementioned particular variant of the invention relates to pharmaceutical compositions containing one or several of these novel compounds. A sixth aspect of the abovementioned particular variant of the invention relates to the use of these novel compounds as CRTH2 antagonists for the prevention and/or treatment of chronic and acute allergic immune disorders comprising allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, basophil-related diseases, such as basophilic leukemia and basophilic leukocytosis in humans and other mammals.

A seventh aspect of the abovementioned particular variant of the invention relates to novel compounds of the general Formula $III_P$

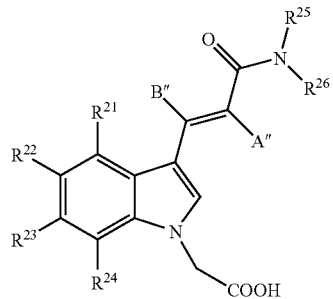

IIIp wherein

A" represents hydrogen; methyl; trifluoromethyl; chloro; or cyano;

B" represents hydrogen; methyl; trifluoromethyl; or chloro;

$R^{21}$, $R^{22}$, $R^{23}$ and $R^{24}$ represent independently hydrogen; lower alkyl; halo-lower alkyl; lower alkoxy; halogen; nitro; cyano or formyl;

$R^{25}$ and $R^{26}$ represent independently hydrogen, lower alkenyl, alkoxy-aryl, alkoxycarbonyl-aryl, lower alkyl, alkylcarbonyl-aryl, arylalkoxy-aryl, arylalkyl, arylalkyl-aryl, aryl, arylcarbonyl-aryl, aryloxy-aryl, cycloalkyl, heteroaryl;

$R^{25}$ and $R^{26}$, together with the nitrogen atom to which they are attached, form a heterocyclic ring system with 3 to 15 ring atoms;

$R^{25}$ represents hydrogen; lower alkyl; or arylalkyl; and $R^{26}$ represents lower alkyl; alkoxy-aryl; alkoxycarbonyl-aryl; alkylcarbonyl-aryl; arylalkoxy-aryl; arylalkyl; arylalkyl-aryl; arylcarbonyl-aryl; aryloxy-aryl or cyclylalkyl; and optically pure enantiomers, mixtures of enantiomers, racemates, optically pure diastereoisomers, mixtures of diastereoisomers, diastereoisomeric racemates, mixture of diastereoisomeric racemates, meso forms, geometric isomers, prodrugs of compounds in which a prodrug forming group is present, as well as solvates and morphological forms and pharmaceutically acceptable salts thereof;

with the proviso that the substituents $R^{21}$, $R^{22}$, $R^{23}$, $R^{24}$, $R^{25}$ and $R^{26}$ all at the same time do not represent hydrogen or in addition and in case either one of the substituents $R^{25}$ or $R^{26}$ represents hydrogen and the other aryl then the aryl group is not an unsubstituted indol-3-yl-ethyl, benzyl, or phenyl group, and also not a $C_1$-$C_3$ alkyl, $C_1$-$C_2$ alkoxy or halogen mono-substituted phenyl group, or $R^{25}$ and $R^{26}$ together with the nitrogen atom to which they are attached do not form a phenyl substituted piperazine ring;

it being understood however that in general Formula $III_P$, the same definitions i) to xi) apply as those given for general Formula $I_P$.

In an eighth aspect of the abovementioned particular variant of the invention, $R^{25}$ and $R^{26}$, together with the nitrogen atom to which they are attached, may form a heterocyclic ring system with 3 to 15 ring atoms and this preferred aspect encompasses novel compounds of Formula $IV_P$

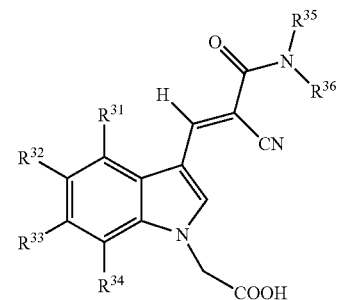

IVp wherein $R^{31}$, $R^{32}$, $R^{33}$ and $R^{34}$ represent independently methyl; trifluoromethyl; methoxy; fluoro, chloro;

$R^{35}$ and $R^{36}$, together with the nitrogen atom to which they are attached, form an acridine, azepine, azocine, carbazole, indole, phenanthiridine or quinoline ring; or $R^{35}$ represents hydrogen, $R^{36}$ represents 2-ethoxy-phenyl, 2-methoxycarbonyl-phenyl, 2-methyl-5-methoxycarbonyl-phenyl, 3-methoxycarbonylphenyl, 4-ethoxycarbonyl-phenyl; 3-methyl-butyl, propyl, 2-acetyl-phenyl, 4-acetyl-phenyl, 3-benzyloxy-phenyl, 4-benzyloxy-phenyl, benzyl, phenethyl; 2-benzyl-phenyl, 2-benzoyl-phenyl, 3-benzoyl-phenyl, 2,3-dihydro-benzo[1,4]dioxin-6-yl, 2,5-dimethyl-phenyl, 2-bromo-4-methyl-phenyl, 2-isopropyl-phenyl, 2-methoxy-dibenzofuran-3-yl, 2-methoxy-phenyl, 2-propyl-phenyl, 3,2'-dimethyl-biphenyl-4-yl, 3,5-bis-trifluoromethyl-phenyl, 3,5-dimethoxyphenyl, 3,5-dimethyl-phenyl, 3-bromo-4-methyl-phenyl, 3-bromophenyl, 3-chloro-4-methoxy-phenyl, 3-ethyl-phenyl, 3-fluoro-phenyl, 3-iodo-phenyl, 3-methoxy-phenyl, 3-nitro-phenyl, 4-bromo-2-methyl-phenyl, 4-bromo-3-chloro-phenyl, 4-bromo-3-methyl-phenyl, 4-butyl-phenyl, 4-chloro-2-methyl-phenyl, 4-cyano-phenyl, 4-iodo-phenyl, 4-isopropyl-phenyl, 4-methoxy-biphenyl-3-yl, 4-propyl-phenyl, 4-sec-butyl-phenyl, 4-tert-butyl-phenyl, 4-trifluoromethoxy-phenyl, 4-trifluoromethyl-phenyl, 5-chloro-2-methoxy-phenyl, 5-methoxy-2-methyl-phenyl, 9-ethyl-9H-carbazol-3-yl, 9H-fluoren-2-yl, 9-oxo-9H-fluoren-1-yl, 9-oxo-9H-fluoren-2-yl, 9-oxo-9H-fluoren-4-yl, benzo[1,3]dioxol-5-yl, biphenyl-4-yl, indan-5-yl, naphthalen-2-yl; 2,4-dichloro-phenoxy)-phenyl, 2-phenoxy-phenyl, 3-phenoxyphenyl, 4-phenoxy-phenyl, cyclohexylmethyl, or $R^{35}$ represents methyl; and $R^{36}$ represents 4-acetyl-phenyl, (R)-1-phenyl-ethyl, benzyl, 3-chloro-phenyl, 4-chloro-phenyl, 4-fluoro-phenyl, 4-methoxy-phenyl, o-tolyl, m-tolyl or p-tolyl;

and optically pure enantiomers, mixtures of enantiomers, racemates, optically pure diastereoisomers, mixtures of diastereoisomers, diastereoisomeric racemates, mixture of diastereoisomeric racemates, meso forms, geometric isomers, prodrugs of compounds in which a prodrug forming group is present, as well as solvates and morphological forms and pharmaceutically acceptable salts thereof.

In a ninth aspect of the abovementioned particular variant of the invention, the compounds of Formula IV$_P$ the substituent $R^{35}$ represents phenyl; and $R^{36}$ represents allyl, 2-cyanoethyl, butyl, carboxymethyl, ethyl, benzyl, phenethyl, phenyl or cyclohexyl.

In a tenth aspect of the abovementioned particular variant of the invention, the substituents $R^{35}$ and $R^{36}$, together with the nitrogen atom to which they are attached form an acridine; azepine; azocine; carbazole; indole; phenanthiridine; or quinoline ring; preferably 5,6-dihydro-phenanthridine; 9,10-dihydro-acridine; 5,6-dihydro-dibenzo[b,f]azocine; 10,11-dihydro-dibenzo[b,f]azepine; 11,12-dihydro-6H-dibenzo[b,f]azocine; 2,3-dihydro-indole; 3,4-dihydro-2H-quinoline; 6,11-dihydro-dibenzo[b,e]azepine; dibenzo[b,f]azepine ring.

Most preferred novel compounds of the abovementioned particular variant of the invention include, but are not limited to:

sodium[3-((E)-2-cyano-3-dibenzo[b,f]azepin-5-yl-3-oxo-propenyl)-indol-1-yl]-acetate;
{3-[(E)-2-(allyl-phenyl-carbamoyl)-2-cyano-vinyl]-indol-1-yl}-acetic acid;
{3-[(E)-2-cyano-2-(phenethyl-phenyl-carbamoyl)-vinyl]-indol-1-yl}-acetic acid;
{3-[(E)-2-(butyl-phenyl-carbamoyl)-2-cyano-vinyl]-indol-1-yl}-acetic acid;
(3-{(E)-2-cyano-2-[(2-cyano-ethyl)-phenyl-carbamoyl]-vinyl}-indol-1-yl)-acetic acid;
{3-[(E)-2-cyano-3-(10,11-dihydro-dibenzo[b,f]azepin-5-yl)-3-oxo-propenyl]-indol-1-yl}-acetic acid;
(3-{(E)-2-cyano-2-[(4-fluoro-phenyl)-methyl-carbamoyl]-vinyl}-indol-1-yl)-acetic acid;
{3-[(E)-2-cyano-2-(ethyl-phenyl-carbamoyl)-vinyl]-indol-1-yl}-acetic acid;
{3-[(E)-2-cyano-3-(6,11-dihydro-dibenzo[b,e]azepin-5-yl)-3-oxo-propenyl]-indol-1-yl}-acetic acid;
{3-[(E)-2-cyano-2-(cyclohexyl-phenyl-carbamoyl)-vinyl]-indol-1-yl}-acetic acid;
(3-{(E)-2-[(4-chloro-phenyl)-methyl-carbamoyl]-2-cyano-vinyl}-indol-1-yl)-acetic acid;
(3-{(E)-2-cyano-2-[(4-methoxy-phenyl)-methyl-carbamoyl]-vinyl}-indol-1-yl)-acetic acid;
{3-[(E)-2-cyano-2-(methyl-o-tolyl-carbamoyl)-vinyl]-indol-1-yl}-acetic acid;
[3-((E)-2-cyano-2-diphenethylcarbamoyl-vinyl)-indol-1-yl]-acetic acid;
(3-{(E)-2-[(4-acetyl-phenyl)-furan-2-ylmethyl-carbamoyl]-2-cyano-vinyl}-indol-1-yl)-acetic acid;
(3-{(E)-2-[(4-acetyl-phenyl)-methyl-carbamoyl]-2-cyano-vinyl}-indol-1-yl)-acetic acid;
{3-[(E)-2-cyano-3-(3,4-dihydro-2H-quinolin-1-yl)-3-oxo-propenyl]-indol-1-yl}-acetic acid.

Particularly preferred novel compounds of the abovementioned particular variant of the invention include:
{3-[(E)-2-cyano-2-(methyl-phenyl-carbamoyl)-vinyl]-indol-1-yl}-acetic acid;
(3-{(E)-2-[(3-chloro-phenyl)-methyl-carbamoyl]-2-cyano-vinyl}-indol-1-yl)-acetic acid;
{3-[(E)-2-(carboxymethyl-phenyl-carbamoyl)-2-cyano-vinyl]-indol-1-yl}-acetic acid;
{3-[(E)-2-(benzyl-phenyl-carbamoyl)-2-cyano-vinyl]-indol-1-yl}-acetic acid;
{3-[(E)-2-(3-benzoyl-phenylcarbamoyl)-2-cyano-vinyl]-indol-1-yl}-acetic acid;
{3-[(E)-2-cyano-2-(2-ethoxy-phenylcarbamoyl)-vinyl]-indol-1-yl}-acetic acid;
{3-[(E)-2-cyano-2-(4-methoxy-biphenyl-3-ylcarbamoyl)-vinyl]-indol-1-yl}-acetic acid;
[3-((E)-2-cyano-2-diphenylcarbamoyl-vinyl)-indol-1-yl]-acetic acid;
(3-{(E)-2-cyano-2-[2-(2,4-dichloro-phenoxy)-phenylcarbamoyl]-vinyl}-indol-1-yl)-acetic acid;
{3-[(E)-2-cyano-2-(2-methoxy-dibenzofuran-3-ylcarbamoyl)-vinyl]-indol-1-yl}-acetic acid;
{3-[(E)-2-cyano-2-(methyl-p-tolyl-carbamoyl)-vinyl]-indol-1-yl}-acetic acid;
{3-[(E)-2-cyano-2-(5-chloro-2-methoxy-phenylcarbamoyl)-vinyl]-indol-1-yl}-acetic acid;
{3-[(E)-2-cyano-2-(2-benzyl-phenylcarbamoyl)-vinyl]-indol-1-yl}-acetic acid;
{3-[(E)-2-cyano-3-(11,12-dihydro-6H-dibenzo[b,f]azocin-5-yl)-3-oxo-propenyl]-indol-1-yl}-acetic acid;
{3-[(E)-2-(2-benzoyl-phenylcarbamoyl)-2-cyano-vinyl]-indol-1-yl}-acetic acid;
{3-[(E)-2-cyano-3-(2,3-dihydro-indol-1-yl)-3-oxo-propenyl]-indol-1-yl}-acetic acid;
{3-[(E)-2-cyano-2-(2-phenoxy-phenylcarbamoyl)-vinyl]-indol-1-yl}-acetic acid;
{3-[(E)-2-cyano-2-(3,5-dimethyl-phenylcarbamoyl)-vinyl]-indol-1-yl}-acetic acid;
{3-[(E)-2-cyano-2-(3-bromo-4-methyl-phenylcarbamoyl)-vinyl]-indol-1-yl}-acetic acid;
{3-[(E)-2-cyano-2-(2-methoxy-phenylcarbamoyl)-vinyl]-indol-1-yl}-acetic acid;
{3-[(E)-2-cyano-2-(2-acetyl-phenylcarbamoyl)-vinyl]-indol-1-yl}-acetic acid;
[3-((E)-2-cyano-2-phenylcarbamoyl-vinyl)-7-methyl-indol-1-yl]-acetic acid.

Preferred novel compounds of the abovementioned particular variant of the invention include:

{3-[(E)-2-cyano-2-(4-trifluoromethoxy-phenylcarbamoyl)-vinyl]-indol-1-yl}-acetic acid;
(3-{(E)-2-cyano-2-[methyl-((R)-1-phenyl-ethyl)-carbamoyl]-vinyl}-indol-1-yl)-acetic acid;
3-[(E)-3-(1-carboxymethyl-1H-indol-3-yl)-2-cyano-acryloylamino]-benzoic acid methyl ester;
{3-[(E)-2-cyano-2-(9-oxo-9H-fluoren-4-ylcarbamoyl)-vinyl]-indol-1-yl}-acetic acid;
{3-[(E)-2-cyano-2-(4-iodo-phenylcarbamoyl)-vinyl]-indol-1-yl}-acetic acid;
{3-[(E)-2-(3-benzyloxy-phenylcarbamoyl)-2-cyano-vinyl]-indol-1-yl}-acetic acid;
{3-[(E)-2-(benzyl-methyl-carbamoyl)-2-cyano-vinyl]-indol-1-yl}-acetic acid;
{3-[(E)-2-cyano-2-(2-propyl-phenylcarbamoyl)-vinyl]-indol-1-yl}-acetic acid;
[5-bromo-3-((E)-2-cyano-2-phenylcarbamoyl-vinyl)-indol-1-yl]-acetic acid;
{3-[(E)-2-cyano-2-(3-methoxy-phenylcarbamoyl)-vinyl]-indol-1-yl}-acetic acid;
{3-[(E)-2-cyano-2-(3-nitro-phenylcarbamoyl)-vinyl]-indol-1-yl}-acetic acid;
{3-[(E)-2-cyano-2-(3,5-dimethoxy-phenylcarbamoyl)-vinyl]-indol-1-yl}-acetic acid;
{3-[(E)-2-cyano-2-(9-ethyl-9H-carbazol-3-ylcarbamoyl)-vinyl]-indol-1-yl}-acetic acid;
{3-[(E)-2-cyano-2-(2,3-dihydro-benzo[1,4]dioxin-6-ylcarbamoyl)-vinyl]-indol-1-yl}-acetic acid;
{3-[(E)-2-(3-chloro-4-methoxy-phenylcarbamoyl)-2-cyano-vinyl]-indol-1-yl}-acetic acid;
4-[(E)-3-(1-carboxymethyl-1H-indol-3-yl)-2-cyano-acryloylamino]-benzoic acid ethyl ester;
{3-[(E)-2-(4-acetyl-phenylcarbamoyl)-2-cyano-vinyl]-indol-1-yl}-acetic acid;
{3-[(E)-2-cyano-2-(2-isopropyl-phenylcarbamoyl)-vinyl]-indol-1-yl}-acetic acid;
{3-[(E)-2-(4-tert-butyl-phenylcarbamoyl)-2-cyano-vinyl]-indol-1-yl}-acetic acid;
{3-[(E)-2-cyano-2-(naphthalen-2-ylcarbamoyl)-vinyl]-indol-1-yl}-acetic acid;
{3-[(E)-2-(benzo[1,3]dioxol-5-ylcarbamoyl)-2-cyano-vinyl]-indol-1-yl}-acetic acid;
{3-[(E)-2-(2-bromo-4-methyl-phenylcarbamoyl)-2-cyano-vinyl]-indol-1-yl}-acetic acid;
{3-[(E)-2-cyano-2-(4-cyano-phenylcarbamoyl)-vinyl]-indol-1-yl}-acetic acid;
{3-[(E)-2-(4-bromo-3-methyl-phenylcarbamoyl)-2-cyano-vinyl]-indol-1-yl}-acetic acid;
[3-((E)-2-cyano-2-phenylcarbamoyl-vinyl)-5-fluoro-indol-1-yl]-acetic acid;
{3-[(E)-2-(biphenyl-4-ylcarbamoyl)-2-cyano-vinyl]-indol-1-yl}-acetic acid;
{3-[(E)-2-cyano-2-(4-isopropyl-phenylcarbamoyl)-vinyl]-indol-1-yl}-acetic acid;
{3-[(E)-2-(4-chloro-2-methyl-phenylcarbamoyl)-2-cyano-vinyl]-indol-1-yl}-acetic acid;
[3-((E)-2-cyano-2-phenylcarbamoyl-vinyl)-5-methyl-indol-1-yl]-acetic acid;
{3-[(E)-2-cyano-2-(4-propyl-phenylcarbamoyl)-vinyl]-indol-1-yl}-acetic acid;
{3-[(E)-2-cyano-2-(2,5-dimethyl-phenylcarbamoyl)-vinyl]-indol-1-yl}-acetic acid;
3-[(E)-3-(1-carboxymethyl-1H-indol-3-yl)-2-cyano-acryloylamino]-4-methyl-benzoic acid methyl ester;
2-[(E)-3-(1-carboxymethyl-1H-indol-3-yl)-2-cyano-acryloylamino]-benzoic acid methyl ester;
{3-[(E)-2-(4-sec-butyl-phenylcarbamoyl)-2-cyano-vinyl]-indol-1-yl}-acetic acid;
{3-[(E)-2-cyano-2-(3-iodo-phenylcarbamoyl)-vinyl]-indol-1-yl}-acetic acid;
{3-[(E)-2-(4-bromo-3-chloro-phenylcarbamoyl)-2-cyano-vinyl]-indol-1-yl}-acetic acid;
[3-((E)-2-cyano-2-cyclohexylcarbamoyl-vinyl)-indol-1-yl]-acetic acid;
{3-[(E)-2-cyano-2-(3-fluoro-phenylcarbamoyl)-vinyl]-indol-1-yl}-acetic acid;
{3-[(E)-2-cyano-2-(4-benzyloxy-phenylcarbamoyl)-vinyl]-indol-1-yl}-acetic acid;
{3-[(E)-2-cyano-2-(3,2'-dimethyl-biphenyl-4-ylcarbamoyl)-vinyl]-indol-1-yl}-acetic acid;
{3-[(E)-2-cyano-2-(5-methoxy-2-methyl-phenylcarbamoyl)-vinyl]-indol-1-yl}-acetic acid;
3-{benzyl-[(E)-3-(1-carboxymethyl-1H-indol-3-yl)-2-cyano-acryloyl]-amino}-propionic acid;
{3-[(E)-2-cyano-2-(9-oxo-9H-fluoren-2-ylcarbamoyl)-vinyl]-indol-1-yl}-acetic acid;
{3-[(E)-2-cyano-2-(3-ethyl-phenylcarbamoyl)-vinyl]-indol-1-yl}-acetic acid;
{3-[(E)-2-(3,5-bis-trifluoromethyl-phenylcarbamoyl)-2-cyano-vinyl]-indol-1-yl}-acetic acid;
[3-((E)-2-cyano-2-phenethylcarbamoyl-vinyl)-indol-1-yl]-acetic acid;
[3-((E)-2-cyano-2-phenylcarbamoyl-vinyl)-6-fluoro-indol-1-yl]-acetic acid;
{3-[(E)-2-(4-bromo-2-methyl-phenylcarbamoyl)-2-cyano-vinyl]-indol-1-yl}-acetic acid;
{3-[(E)-2-cyano-2-(4-trifluoromethyl-phenylcarbamoyl)-vinyl]-indol-1-yl}-acetic acid;
{3-[(E)-2-cyano-2-(4-phenoxy-phenylcarbamoyl)-vinyl]-indol-1-yl}-acetic acid;
{3-[(E)-2-cyano-2-(indan-5-ylcarbamoyl)-vinyl]-indol-1-yl}-acetic acid;
{3-[(E)-2-cyano-2-(9H-fluoren-2-ylcarbamoyl)-vinyl]-indol-1-yl}-acetic acid;
{3-[(E)-2-cyano-2-(cyclohexylmethyl-carbamoyl)-vinyl]-indol-1-yl}-acetic acid;
{3-[(E)-2-(4-butyl-phenylcarbamoyl)-2-cyano-vinyl]-indol-1-yl}-acetic acid;
{3-[(E)-2-(benzyl-carboxymethyl-carbamoyl)-2-cyano-vinyl]-indol-1-yl}-acetic acid;
{3-[(E)-2-cyano-2-(3-phenoxy-phenylcarbamoyl)-vinyl]-indol-1-yl}-acetic acid;
{3-[(E)-2-cyano-2-(9-oxo-9H-fluoren-1-ylcarbamoyl)-vinyl]-indol-1-yl}-acetic acid.

Other preferred novel compounds of the abovementioned particular variant of the invention include
[3-((E)-2-cyano-2-propylcarbamoyl-vinyl)-indol-1-yl]-acetic acid;
{3-[(E)-2-cyano-2-(3-methyl-butylcarbamoyl)-vinyl]-indol-1-yl}-acetic acid;
[3-((E)-2-cyano-2-phenylcarbamoyl-vinyl)-6-nitro-indol-1-yl]-acetic acid.

The following paragraphs provide definitions of i.a. the various chemical moieties that make up the compounds according to the invention and are intended to apply uniformly throughout the specification and claims unless an otherwise expressly set forth definition provides a broader or narrower definition.

Therefore, and unless explicitly stated otherwise, the general terms and names used hereinbefore and hereinafter preferably have within the context of this disclosure the following meanings:

Firstly, any reference to a compound of general formula I is to be understood as referring also to configurational isomers, mixtures of enantiomers such as racemates, diastereomers, mixtures of diastereomers, diastereomeric racemates, and mixtures of diastereomeric racemates, as well as salts, solvent complexes, and morphological forms of such compounds, as appropriate and expedient.

The term "alkyl" or "lower alkyl", as used herein, alone or in any combination, refers to a saturated aliphatic group including a straight or branched hydrocarbon chain containing 1-8 carbon atoms, preferably 1-4 carbon atoms. Representative examples of alkyl include, but are not limited to, methyl, ethyl, n-propyl, iso-propyl, n-butyl, sec-butyl, tert-butyl, iso-butyl (or 2-methylpropyl), n-pentyl (or n-amyl), iso-pentyl (or iso-amyl), n-hexyl, n-heptyl, n-octyl and the like.

The term "alkenyl" or "lower alkenyl", as used herein, alone or in any combination, refers to a straight or branched hydrocarbon chain containing 2-8 carbon atoms with at least one carbon-carbon double bond. Representative examples of alkenyl include, but are not limited to, ethenyl, 2-propenyl, 2-methyl-2-propenyl, 3-butenyl, 4-pentenyl, 5-hexenyl and the like.

The term "alkoxy" or "lower alkoxy", as used herein, alone or in any combination, refers to an alkyl group appended to the parent molecular moiety through an oxygen bridge. Representative examples of alkoxy include, but are not limited to, methoxy, ethoxy, propoxy, 2-propoxy, butoxy, tert-butoxy, pentyloxy, hexyloxy, and the like.

The term "aryl", as used herein, alone or in any combination (except for arylalkoxy, arylalkyl, aryloxy and arylcarbonyl which are defined below), refers either to a carbocyclic group having at least one aromatic ring, e.g. phenyl or biphenyl, or multiple condensed ring systems, in which at least one ring is aromatic (e.g. 1,2,3,4-tetrahydronaphthyl, naphthyl, anthryl, phenanthryl, fluorenyl, indanyl, and the like) or to a phenyl group having two vicinal substituents forming together a methylenedioxy chain or an ethylene dioxy chain (that is to a 2,3-dihydrobenzo[1,4]dioxinyl or a benzo[1,3] dioxolyl group). The aryl group may be optionally substituted with one to three functional groups individually and independently selected from alkoxy, alkoxycarbonyl, alkyl, alkylcarbonyl, arylalkoxy, arylcarbonyl, arylalkyl, aryloxy, cyano, halogen, haloalkoxy, haloalkyl, nitro, and the like. Besides, in the particular cases wherein the aryl group consists of multiple condensed ring systems, in which not all rings are aromatic, one of the carbon atoms that is not member of an aromatic ring may be in an oxidised form and the corresponding —CH$_2$— ring member will then be replaced by —C(O)—; representative examples of such aryl groups include, but are not limited to, 9-oxo-9H-fluorenyl.

A particular example of the "aryl" group is "phenyl". The term "phenyl", as used herein, alone or in any combination (except for phenylalkyl and diphenylalkyl which are defined below), refers to an unsubstituted phenyl group or to a phenyl group substituted with one to three functional groups individually and independently selected from alkoxy, alkoxycarbonyl, alkyl, alkylcarbonyl, arylalkoxy, arylcarbonyl, arylalkyl, aryloxy, cyano, halogen, haloalkoxy, haloalkyl, nitro, and the like.

The term "phenylalkyl", as used herein, alone or in any combination, refers to a phenyl group appended to the parent molecular moiety through an alkyl group wherein however the phenyl group may be unsubstituted or substituted with 1 to 3 substituents selected independently from the group consisting of halogen, alkyl, alkoxy, trifluoromethyl and trifluoromethoxy. Representative examples of phenylalkyl include, but are not limited to, benzyl, 2-phenylethyl, 3-phenylpropyl, and the like.

The term "diphenylalkyl", as used herein, alone or in any combination, refers to an alkyl group wherein two hydrogen atoms have each been replaced by an unsubstituted phenyl group.

The term "arylalkoxy", as used herein, alone or in any combination, refers to an aryl group appended to the parent molecular moiety through an alkoxy group wherein however the aryl group may be unsubstituted or substituted with 1 to 3 substituents selected independently from the group consisting of halogen, alkyl, alkoxy, trifluoromethyl and trifluoromethoxy. Representative examples of arylalkoxy include, but are not limited to, 2-phenylethoxy, 5-phenylpentyloxy, 3-naphth-2-ylpropoxy, and the like.

The term "arylalkyl", as used herein, alone or in any combination, refers to an aryl group appended to the parent molecular moiety through an alkyl group wherein however the aryl group may be unsubstituted or substituted with 1 to 3 substituents selected independently from the group consisting of halogen, alkyl, alkoxy, trifluoromethyl and trifluoromethoxy. Representative examples of arylalkyl include, but are not limited to, benzyl, 2-phenylethyl, 3-phenylpropyl, 2-naphth-2-ylethyl, and the like.

The term "aryloxy", as used herein, alone or in any combination, refers to an aryl group appended to the parent molecular moiety through an oxygen bridge wherein however the aryl group can be unsubstituted or substituted with 1 to 3 substituents selected independently from the group consisting of halogen, alkyl, alkoxy, trifluoromethyl and trifluoromethoxy. Representative examples of aryloxy include, but are not limited to, phenoxy, naphthyloxy, 3-bromophenoxy, 4-chlorophenoxy, 4-methylphenoxy, 3,4-dimethoxyphenoxy, and the like.

The term "arylcarbonyl" or "aroyl", as used herein, alone or in any combination, refers to an aryl group appended to the parent molecular moiety through a carbonyl group wherein however the aryl group can be unsubstituted or substituted with 1 to 3 substituents selected independently from the group consisting of halogen, alkyl, alkoxy, trifluoromethyl and trifluoromethoxy. Representative examples of alkylcarbonyl include, but are not limited to, phenylcarbonyl (or benzoyl), naphthylcarbonyl and the like.

The term "carbonyl", as used herein, alone or in any combination, refers to a —C(O)— group.

The term "carboxy", as used herein, alone or in any combination, refers to a —CO$_2$H group.

The term "carboxyalkyl", as used herein, alone or in any combination, refers to a carboxy group appended to the parent molecular moiety through an alkyl group. Representative examples of carboxyalkyl include, but are not limited to, carboxymethyl, 2-carboxyethyl, 3-carboxypropyl, and the like.

The term "cyano", as used herein, alone or in any combination, refers to a —C≡N group.

The term "cycloalkyl", as used herein, alone or in any combination, refers to a saturated cyclic hydrocarbon moiety containing 3-15 carbon atoms. Representative examples of cycloalkyl include, but are not limited to, cyclopropyl, cyclobutyl, cyclopentyl, cyclohexyl, cycloheptyl, cyclooctyl and the like.

The term "cyclylalkyl" or "cycloalkyl-alkyl", as used herein, alone or in any combination, refers to an cycloalkyl group appended to the parent molecular moiety through an alkyl group. Representative examples of cyclylalkyl or cycloalkyl-alkyl include, but are not limited to, cyclopropylmethyl, cyclohexylethyl, and the like.

The term "formyl", as used herein, alone or in any combination, refers to a —C(O)H group.

The term "halo" or "halogen", as used herein, alone or in any combination, refers to fluorine, bromine, chlorine, and iodine.

The term "heterocyclyl" or "heterocyclic ring system", as used herein, alone or in any combination, refers to a monocyclic, bicyclic or polycyclic ring system containing up to ring atoms, at least one of these being a heteroatom independently selected from the group consisting of nitrogen, oxygen and sulfur. The ring system may be saturated, partially unsaturated, unsaturated or aromatic. Representative examples of heterocyclyl or heterocyclic ring system include, but are not limited to, furyl, imidazolyl, imidazolinyl, imidazolidinyl, isothiazolyl, isoxazolyl, morpholinyl, oxadiazolyl, oxazolyl, oxazolinyl, oxazolidinyl, piperazinyl, piperidinyl, pyranyl, pyrazinyl, pyrazolyl, pyridyl, pyrimidinyl, pyridazinyl, pyrrolyl, pyrrolinyl, pyrrolidinyl, tetrahydrofuranyl, tetrahydrofuranyl, tetrahydrothienyl, thiadiazolyl, thiazolyl, thiazolinyl, thiazolidinyl, thienyl, thiomorpholinyl, benzimidazolyl, benzothiazolyl, benzothienyl, benzoxazolyl, benzofuranyl, indolyl, indolinyl, isobenzofuranyl, isobenzothienyl, isoindolyl, isoindolinyl, isoquinolinyl, dihydroisoquinolinyl, quinolinyl, dihydroquinolinyl, carbazolyl, phenothiazinyl, phenoxazinyl, dihydrodibenzoazocinyl, dibenzoazepinyl, dihydrodibenzoazepinyl, oxa-aza-dibenzocycloheptenyl, and the like. Defined heterocyclyl moieties may be optionally substituted with one or more groups, each individually and independently selected from the group consisting of alkoxy, alkyl, alkylcarbonyl, halogen, haloalkoxy and haloalkyl.

The term "heteroaryl", as used herein, alone or in any combination, refers to a mono-, bi- or tricyclic aromatic ring system containing up to 14 ring atoms wherein at least one of the rings contains at least one heteroatom independently selected from the group consisting of nitrogen, oxygen and sulfur. The heteroaryl group can be unsubstituted or substituted with 1 to 3 substituents selected independently from the group consisting of halogen, alkyl, alkoxy, trifluoromethyl and trifluoromethoxy. Representative examples of heteroaryl include, but are not limited to, thienyl, furanyl, pyrrolyl, thiazolyl, imidazolyl, oxazolyl, pyridyl, quinolinyl, benzimidazolyl, benzothiazolyl, benzothienyl, benzoxazolyl, benzofuranyl, indolyl, carbazolyl, phenothiazin, phenoxazin, and the like.

The term "nitro", as used herein, alone or in any combination, refers to a —$NO_2$ group.

The term "oxo", as used herein, alone or in any combination, refers to a =O group.

The term "oxy", as used herein, alone or in any combination, refers to a —O— group.

Within the scope of the present invention, unless indicated otherwise, compounds of formula I, $I_{C1}$, $I_{C2}$, $I_P$ or the novel compounds of the formula $II_P$, $III_P$ or $IV_P$ and pharmaceutically acceptable salts thereof are included that may exist in, and be isolated in, isomeric forms, including cis- or trans isomers or mixtures thereof, and tautomers. Other compounds of this invention may contain one or more stereogenic or asymmetric centers, such as one or more asymmetric carbon atoms, and thus may give rise to optically pure enantiomers, mixtures of enantiomers, racemates, enantiomer-pure diastereomers, mixtures of diastereomers, epimers, and other stereoisomeric forms that may be defined, in terms of absolute stereochemistry, as (R)-, (S)- or (R,S)-configured, preferably in the (R)- or (S)-configuration. Such isomers can be obtained by methods within the knowledge of one skilled in the art, e.g. by stereochemically controlled synthesis using chiral synthons or chiral reagents, or by means of classical separation techniques, such as chromatographic or crystallization methods, or by other methods known in the art, such as through formation of diastereomeric salts, for example by salt formation with an enantiomerically pure chiral acid, or by means of chromatography, for example by using chromatographic materials modified with chiral ligands. Furthermore, the present invention refers to compounds containing centers of any geometric asymmetry, like, for example, unsymmetrically substituted olefinic double bond, including E or Z geometric isomers and mixtures thereof. Generally, pure isomers of compounds of Formula I, $I_{C1}$, $I_{C2}$, $I_P$ or II are preferred over isomeric mixtures.

In the present invention, the compounds of formula I, $I_{C1}$, $I_{C2}$, $I_P$, $II_P$, $III_P$ or $IV_P$ may be used in the form of pharmaceutically acceptable salts. The term "pharmaceutically acceptable salts" refers to relatively non-toxic, inorganic or organic acid and base addition salts, which retain the biological effectiveness and properties of the parent compound, and which are not biologically or otherwise undesirable (see, e.g., Berge et al., *J. Pharm. Sci.* (1977), 66, 1-19 or "Salt selection for basic drugs", *Int. J. Pharm.* (1986), 33, 201-217).

Certain compounds of the present invention can contain one or more basic functional groups, such as amino, alkylamino, or arylamino, and, thus, be capable of forming pharmaceutically acceptable acid addition salts. These acid addition salts may be prepared by standard procedures in a suitable solvent from the parent compound of Formula I or II, with an appropriate amount of an inorganic acid, including, but not limited to, for example, hydrochloric acid, hydrobromic acid, sulfuric acid, or phosphoric acid; or of an organic acid, including, but not limited to, acetic acid, propionic acid, octanoic acid, decanoic acid, glycolic acid, pyruvic acid, oxalic acid, maleic acid, malonic acid, succinic acid, fumaric acid, tartaric acid, citric acid, ascorbic acid, amino acids, such as glutamic acid or aspartic acid, benzoic acid, cinnamic acid, salicylic acid, mandelic acid, methanesulfonic acid, ethanesulfonic acid, p-toluenesulfonic acid, or other acidic organic compounds.

Certain compounds of the present invention may, on the other hand, contain one or more acidic functional groups and, thus, be capable of forming pharmaceutically acceptable base addition salts. These salts can be prepared by addition of an appropriate amount, usually in stoichiometric ratio, of an alkaline reagent, such as hydroxide, carbonate or alkoxide, containing the appropriate cation, to the free acid in a suitable solvent. Preferred inorganic salts include, but are not limited to, ammonium, sodium, potassium, calcium or magnesium, also zinc salts and the like. Preferred salts derived from organic bases include, but are not limited to, salts of primary, secondary, and tertiary amines, substituted amines, cyclic amines, and basic ion exchange resins, such as isopropylamine, trimethylamine, diethylamine, triethylamine, tripropylamine, ethanolamine, lysine, arginine, N-ethylpiperidine, piperidine, polyamine resins, and the like.

Compounds of the present invention containing both acidic and basic groups can also form internal salts (zwitter ions).

For isolation or purification purposes, it is also possible to use pharmaceutically unacceptable salts, for example perchlorates, picolinates, picrates, or the like. For therapeutic use, only pharmaceutically acceptable salts or free compounds are employed, where applicable in the form of pharmaceutical preparations, and these are therefore preferred.

Certain compounds of formula I, $I_{C1}$, $I_{C2}$, $I_P$, $II_P$, $III_P$ or $IV_P$ including their salts, may exist in solvated as well unsolvated forms, such as, for example, hydrated forms, or their crystals may, for example, include the solvent used for crystallization. Different crystalline forms may be present. The present invention encompasses all such solvated and unsolvated forms.

The present invention also relates to prodrug derivatives of the parent compounds of formula I, $I_{C1}$, $I_{C2}$, $I_P$, $II_P$, $III_P$ or $IV_P$. The term "prodrug" refers to pharmacologically inactive precursors of a drug that may be converted into its therapeutically active form under physiological conditions in vivo, for example, when they undergo solvolysis, or enzymatic degradation in blood, or in cells, (Bundgard H., "Design of Prodrugs", pp. 7-9, 21-24, Elsevier, Amsterdam (1985); Silverman R. B., "The Organic Chemistry of Drug Design and Drug Action", pp. 352-401, Academic Press, San Diego, Calif. (1992); Higuchi T. et al., "Pro-drug as Novel Delivery Systems", A.C.S. Symposium Series, Vol. 14). The term "prodrug" also includes any covalently bonded carriers, which release the active parent compound in vivo when administered to a mammal. Prodrug modifications of a compound often offer advantages of solubility, bioavailability, absorption, tissue compatibility, tissue distribution, or delayed release in the mammalian organism. Prodrugs are variations or derivatives of the compounds of formula I, which have groups cleavable under metabolic conditions, for example, pharmaceutically acceptable esters, or amides. Such groups can be cleaved enzymatically or non-enzymatically, or hydrolytically to the free hydroxy, carboxy, or amino group of the active parent compound. In another embodiment, the prodrug is a reduced form, which is oxidized in vivo to the therapeutic compound, for example, a thiol, which is oxidized to a sulfonate or sulfate, an alcohol to a carboxylic acid.

Further included within the scope of the present invention are pharmaceutically acceptable esters of the compounds of formula I, $I_{C1}$, $I_{C2}$, $I_P$, $II_P$, $III_P$ or $IV_P$. The term "pharmaceutically acceptable esters" refers to relatively non-toxic, esterified products of the parent compound. These esters can be prepared in situ during the final isolation and purification of the compounds, or by separately reacting the purified compounds in its free acid or hydroxyl form with a suitable esterifying agent. Carboxylic acids can be converted into esters via treatment with an alcohol in the presence of a catalyst. Hydroxyl containing derivatives can be converted into esters via treatment with an esterifying agent such as alkanoyl halides. The term further includes lower hydrocarbon groups capable of being solvated under physiological conditions, for example, alkyl esters, preferred methyl, ethyl, and propyl ester, methoxymethyl ester, methylthiomethyl ester, pivaloyloxymethyl ester and the like (see, e.g., Berge et al., *J. Pharm. Sci.* (1977), 66, 1-19).

The compounds of the present invention have useful, in particular pharmacologically useful, properties. They are able to specifically antagonize the effect of endogenous $PGD_2$ on the CRTH2 receptor.

A compound or a pharmaceutical composition of the invention may be used as a drug (medicine) or therapeutic agent for prevention and/or treatment of both chronic and acute allergic/immune disorders such as allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, basophil-related diseases, such as basophilic leukemia and basophilic leukocytosis.

In another aspect, the compounds of formula I, $I_{C1}$, $I_{C2}$ or $I_P$ may be used as standard or reference compounds in tests or assays involving the inhibition of the CRTH2 receptor. Such compounds could be made commercially available for use as a reference, quality standard or control, for example in pharmaceutical research when developing new assays or protocols related to CRTH2 activity.

As mentioned earlier, compounds of formula I, $I_{C1}$, $I_{C2}$ or $I_P$, or salts, or prodrugs thereof, antagonize the $PGD_2$ activation of the CRTH2 receptor. The biological effect of such compounds may be tested in a variety of in vitro, ex vivo and in vivo assays.

The ability of the compounds of formula I, $I_{C1}$, $I_{C2}$ or $I_P$ to bind to the CRTH2 receptor may be measured by methods similar to those described in Sawyer N. et al., *Br. J. Pharmacol.* (2002), 137, 1163-1172 and by the method described below in Example B-1.

With this type of assay, $IC_{50}$ values (i.e. the concentrations where half-maximal inhibition of the interaction is found) in the range of 0.001 to 10 µM, preferably values below 1 µM, in particular values below 0.05 µM, are found with test compounds of formula I, $I_{C1}$, $I_{C2}$ or $I_P$ (see the paragraph entitled "Biological results").

A functional assay with cells expressing the human CRTH2 receptor may be used to detect changes in the levels of intracellular calcium concentration following compound treatment. After addition of the compound the cells are challenged with $PGD_2$. In a Fluorescent Imaging Plate Reader (FLIPR™, Molecular Devices, Sunnyvale, Calif.) fluorescence emission is recorded during both additions, emission peak values above base level after $PGD_2$ addition were exported, normalized to low controls (no $PGD_2$) and high controls (no active compound). The relative values of the remaining activity were used to determine $IC_{50}$ values by curve fitting the data to a single site to a four-parameter logistic sigmoid dose response curve of the equation $(A+((B-A)/(1+((C/x)^D))))$.

The ability of the compounds to antagonize $PGD_2$ induced change of intracellular calcium levels via CRTH2 activation may be measured by methods known of one skilled in the art or by the method described below in Example B-2.

With this assay, $IC_{50}$ values (i.e. the concentration of a compound at which the remaining activity is 50%) in the range of 0.001 and 10 µM, preferably below 0.5 µM, are obtained with test compounds of formula I, $I_{C1}$, $I_{C2}$ or $I_P$ (see the paragraph entitled "Biological results").

The results of these assays clearly demonstrate that the present invention provides functional antagonists of the $PGD_2$ receptor.

On the basis of the biological studies discussed hereinabove, a compound of Formula I according to the invention may show therapeutic efficacy against chronic and acute allergic/immune disorders such as allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, basophil-related diseases, such as basophilic leukemia and basophilic leukocytosis.

A compound of formula I, $I_{C1}$, $I_{C2}$ or $I_P$, a pharmaceutically acceptable salt or a prodrug thereof, can be administered alone in pure form or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of Formula I can besides or in addition be administered especially for prevention and/or treatment of both chronic and acute allergic or immune disorders in combination with other inflammatory diseases. Long-term therapy is equally possible as is adjuvant therapy in the context of other treatment strategies, as described above. Other possible treatments are preventive therapies, for example in patients at risk.

The invention relates to pharmaceutical compositions comprising compounds of formula I, $I_{C1}$, $I_{C2}$ or $I_P$, to their use in therapeutic, in a broader aspect of the invention also prophylactic treatment or a method of treatment of the diseases mentioned above, to the compounds for said use and to the preparation of pharmaceutical formulations (medicines).

The pharmaceutically acceptable compounds of the present invention may be used, for example, for the preparation of pharmaceutical compositions that comprise an effective amount of the active ingredient together or in admixture with a significant amount of one or more inorganic, organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, for the treatment or, in a broader aspect of the invention, prevention of (i.e. prophylaxis against) a disease that responds to blockade of the interaction of the CRTH2 receptor with $PGD_2$, comprising an amount of a compound of formula I, $I_{C1}$, $I_{C2}$ or $I_P$ or a pharmaceutically acceptable salt or a prodrug thereof, which is effective for said inhibition, together with at least one pharmaceutically acceptable carrier.

The pharmaceutical compositions according to the invention are those for enteral administration, such as nasal, buccal, rectal, dermal or, especially oral administration, and for parenteral administration, such as intramuscular, intravenous or subcutaneous, intrasternal, intravitreal, injection or infusion, to warm-blooded animals, especially humans. Such compositions comprise an effective dose of the pharmaceutically active ingredient, alone or together with a significant amount of a pharmaceutically acceptable carrier. The dosage of the active ingredient depends on the species of warm-blooded animal, the body weight, the age and the individual conditions, individual pharmacokinetic data, the disease to be treated and the mode of administration.

The invention relates also to a process or a method for the treatment of a pathological condition mentioned hereinabove, especially a disease, which responds to blockade of the interaction of the CRTH2 receptor with $PGD_2$, especially allergic/immune disorders such as allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, basophil-related diseases, such as basophilic leukemia and basophilic leukocytosis. The compounds of formula I, $I_{C1}$, $I_{C2}$, $I_P$ or salts or prodrugs thereof can be administered as such or especially in the form of pharmaceutical compositions.

The dose to be administered to warm-blooded animals, for example humans of approximately 70 kg body weight, is preferably from approximately 3 mg to approximately 30 g, more preferably from approximately 10 mg to approximately 1000 mg per person per day, divided preferably into 1 to 3 single doses which may, for example, be of the same size. The amount of the compound actually administered will typically be determined by a physician, in the light of the relevant circumstances, including the condition to be treated, the chosen route of administration, the actual compound administered, the age, the weight, and response of the individual patient, the severity of the patient's symptoms, and the like, for example, children usually receive half of the adults dose.

The pharmaceutical compositions comprise from approximately 1% to approximately 95%, preferably from approximately 20% to approximately 90%, active ingredient. Pharmaceutical compositions according to the invention may be, for example, in unit dosage forms such as coated and uncoated tablets, pills, ampoules, vials, suppositories, dragées, or capsules. Further dosage forms are, for example, ointments, creams, pastes, emulsions, foams, chewable gums, tinctures, lip-sticks, drops, sprays or aerosols, syrups or elixirs, dispersions, transdermal patches or pads, or via an intravitreal device that releases the compound in a sustained capacity, and the like. Examples are capsules containing from about 0.05 g to about 1.0 g active ingredient.

The pharmaceutical compositions of the present invention are prepared in a manner known, per se, for example by means of conventional mixing, granulating, coating, dissolving, lyophilizing or confectioning processes.

Solutions of the active ingredient, and also suspensions, and especially isotonic aqueous solutions or suspensions, are preferably used, it being possible, for example in the case of lyophilized compositions, that comprise the active ingredient alone or together with a carrier, for example mannitol, for such solutions or suspensions to be produced prior to use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chain fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is mono- or poly-hydroxy, for example a mono-, di- or trihydroxy, alcohol, for example methanol, ethanol, propanol, butanol, or pentanol or the isomers thereof, but especially glycol and glycerol. The following examples of fatty acid esters are therefore to be mentioned: ethyl oleate, isopropyl myristate, isopropyl palmitate, "Labrafil M2375" (polyoxyethylene glycerol trioleate, Gattefossé, Paris), "Miglyol 812" (triglyceride of saturated fatty acids with chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection or infusion compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice, or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum Arabic, talc, polyvinylpyrrolidone, polyethylene glycol, and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and of soft sealed capsules made of gelatine and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilizers. In soft capsules the active ingredient is preferably dissolved or suspended in suitable oil excipients, such as fatty oils, paraffin oil or liquid polyethylene glycols, it being possible also for stabilizers and/or antibacterial agents to be added. Dyes or pigments may be added to the tablets or dragée coatings or the capsule casings, for example for identification purposes or to indicate different doses of active ingredient.

For parenteral administration, aqueous solutions of an active ingredient in water-soluble form, for example of a water-soluble salt, or aqueous injection suspensions that contain viscosity-increasing substances and stabilizers, are especially suitable. The active ingredient, optionally together with excipients, can also be in the form of a lyophilizate and be made into a solution before parenteral administration by the addition of solvents.

A further object of the invention is a process for preparing pyridoindol derivatives according to Formula I, $I_{C1}$, $I_{C2}$ or $I_P$. Compounds according to formula I of the present invention are prepared according to the general sequence of reactions outlined in the schemes below, wherein $R^1$, $R^2$, $R^3$, $R^4$, $R^5$ and $R^6$ are as defined in formula I, $I_{C1}$, $I_{C2}$ or $I_P$. The compounds obtained may also be converted into a pharmaceutically acceptable salt thereof in a manner known per se.

Compounds of the invention may be manufactured by the application or adaptation of known methods, by which is meant methods used heretofore or described in the literature, for example those described by Larock R. C. in "Comprehensive organic transformations: a guide to functional group preparations", VCH publishers, 1999.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for example see Greene T. W. and Wuts P. G. M. in "Protective groups in organic synthesis" Wiley-Interscience, 1999.

Generally, the synthesis of indolacetic acid derivatives of formula I starts as outlined in Scheme 1 and 2 with indole of formula 1, which by means of phosphorous oxychloride in dimethylformamide is converted in a Vilsmeyer reaction to the formyl derivative of formula 2 (R. Gastpar et al., *J. Med. Chem.* (1998), 41, 4965-4972). Subsequent condensation with a secondary amine, such as pyrrolidine or the like, in a solvent appropriate to azeotropically remove water formed in a reaction, such as toluene, benzene or the like, leads to Schiff base of formula 3, that then reacts with a compound of formula L-CH$_2$CO$_2$R, in which R represents an alkyl group, preferably ethyl or tert-butyl, and L is a leaving group, in the presence of a base, such as caesium carbonate, sodium hydride or the like, in a suitable solvent, such as alcohol, preferably ethanol, or acetone, tetrahydrofuran, dioxane, to yield indolium salt of Formula 4. Suitable L is a leaving group such as halo, in particular bromo or chloro. Preferably, the compound of formula L-CH$_2$CO$_2$R is ethyl bromoacetate.

Indolium salt of formula 4 is condensed with cyanoacetic acid ester of formula NC—CH$_2$—COOR', wherein R' represents an alkyl group, preferably ethyl or tert.-butyl, in the presence of a base, such as sodium ethoxide, to form cyanoacrylic ester of formula 5 (T. Moriya et al., *Chem. Pharm. Bull.* 1980, 28, 1711-1721). Cleavage of the ester group, either under acidic or basic conditions, such as TFA in dichloromethane or sodium hydroxide in THF, respectively, gave carboxylic acid of formula 6, which then was converted to the corresponding acyl halide of formula 7 by means of a halogenating reagent under conditions known to a skilled person. Preferably, the carboxylic acid is converted to the acid chloride using oxalyl chloride in the presence of a catalytical amount of dimethylformamide in an appropriate solvent, such as dichloromethane or toluene or the like.

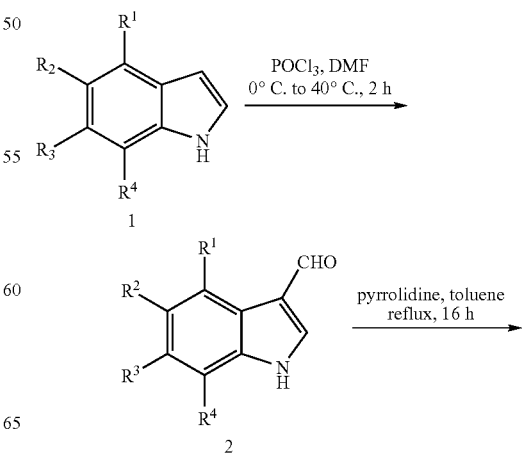

Scheme 2

Step a)

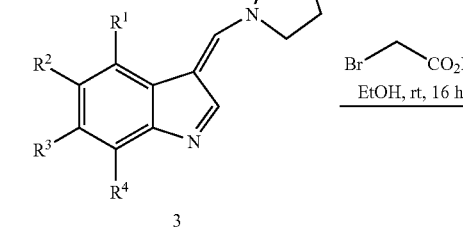

3

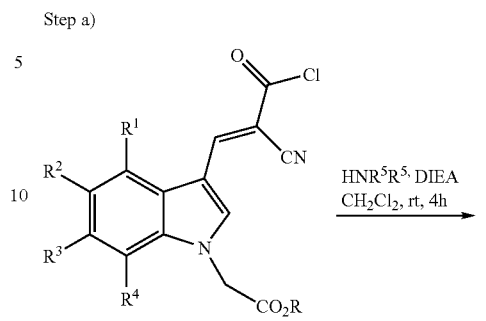

Intermediate A-G

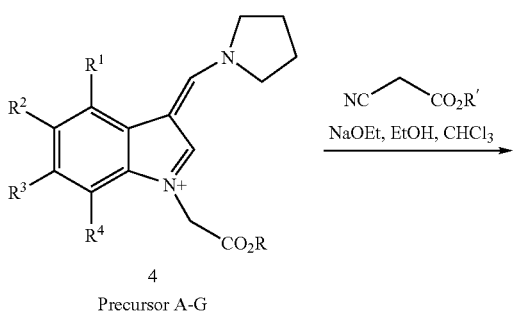

4

Precursor A-G

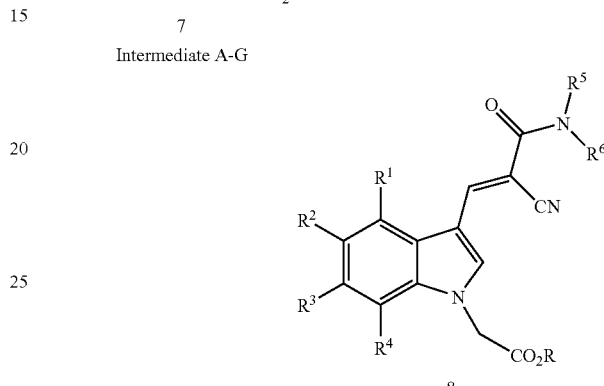

8

Step b)

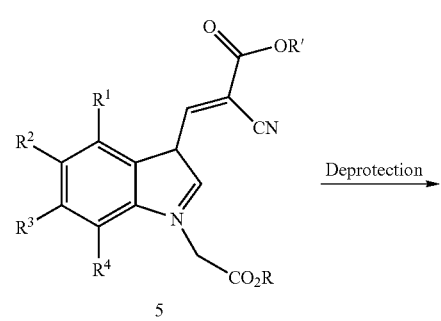

5

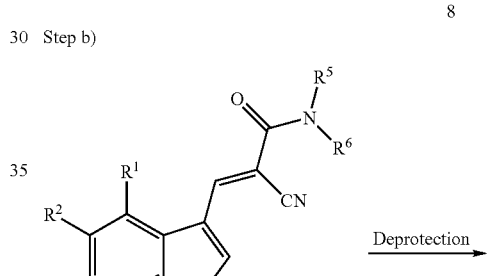

8

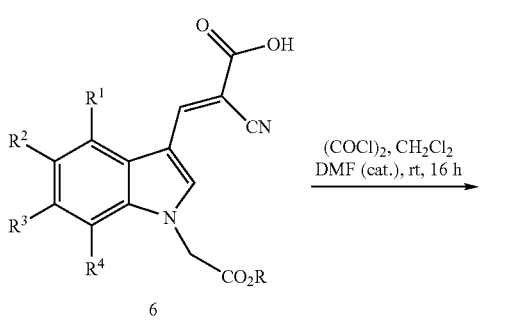

6

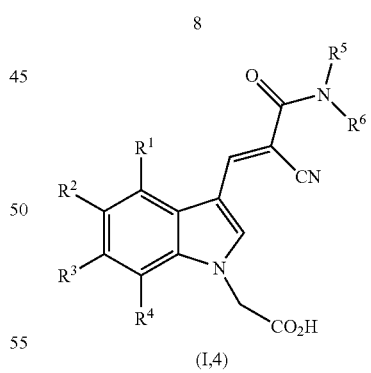

(I,4)

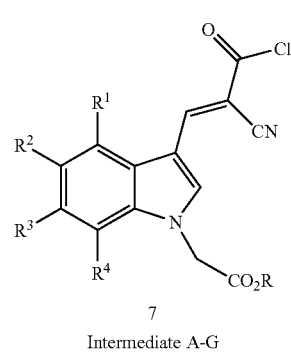

7

Intermediate A-G

The treatment of an acyl halide of formula 7 with a primary amine of formula $R^6$—$NH_2$ in a suitable solvent, such as dichloromethane, tetrahydrofuran, or N,N-dimethylformamide, gives a N-substituted amide of formula 8, wherein $R^5$ is a hydrogen atom, while a secondary amine of formula $NHR^5R^6$ gives a N,N-disubstituted amide of formula 8. Preferably a base such as triethylamine, N,N-diisopropylethylamine, N-ethyl-morpholine, N-methylpiperidine, or pyridine is added to combine with the liberated hydrochloric acid.

Hydrolysis of the ester group R in formula 8 can be carried out using routine procedures, as outlined in Scheme 2, Step b), for example by stirring with aqueous sodium hydroxide, or trifluoroacetic acid to give a compound of formula (I.,4).

Alternatively, indolacetic acid derivatives of Formula I can be synthesized in two consecutive steps as outlined in Scheme 3, starting from abovementioned Schiff base of formula 4 (Step c), which is reacted first with 2-cyano-acetamide of formula NC—CH₂—CONR⁵R⁶ to form an amide of Formula 8. Final deprotection under standard conditions, as outlined in Scheme 3, Step b), delivers a final compound of formula (I,4).

The reagent 2-cyano-acetamide of formula NC—CH²—CONR⁵R⁶ is prepared from cyanoacetic acid and a primary or secondary amine under conditions known to a skilled person.

Scheme 3

Step c)

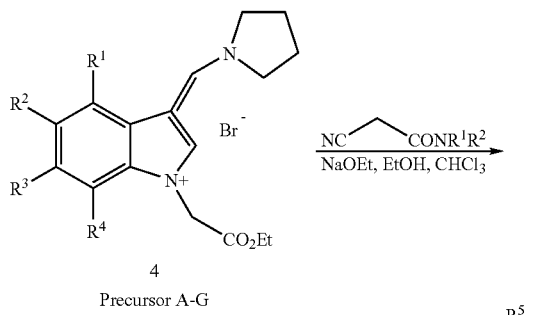

Step b)

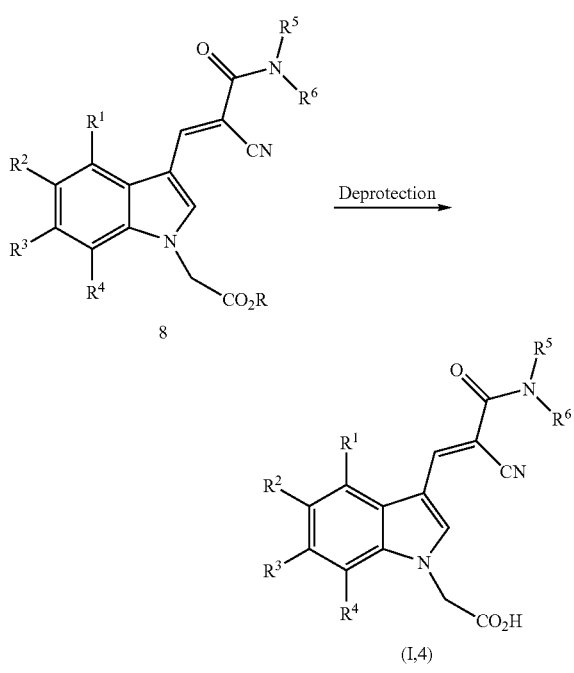

Particular embodiments of the invention are described in the following Examples, which serve to illustrate the invention in more detail without limiting its scope in any way.

EXAMPLES

Temperatures are indicated in degrees Celsius (° C.). Unless otherwise indicated, the reactions take place at room temperature (rt).

In mixtures, relations of parts of solvent or eluent or reagent mixtures in liquid form are given as volume relations (v/v), unless indicated otherwise.

ABBREVIATIONS AND ACRONYMS USED

AcOH: acetic acid; NH₄OH: ammonium hydroxide; BSA: bovine serum albumin; calcd: calculated; CH₂Cl₂: dichloromethane; DIEA: N,N-diisopropylethylamine; DMF: N,N-dimethylformamide, DMSO: dimethyl sulfoxide; EDTA: ethylenediaminetetraacetic acid; Et₃N: triethylamine; EtOAc: ethyl acetate; EtOH: ethanol; g: gram; h: hour; H₂O: water; HCl: hydrochloric acid; HEPES: 4-(2-hydroxyethyl)-piperazin-1-ethanesulfonic acid buffer; HPLC: high-performance liquid chromatography; k: kilo; K₂CO₃: potassium carbonate; KHSO₄: potassium hydrogenosulfate; l: liter; MgCl₂: magnesium chloride; MgSO₄: magnesium sulfate; l: micro; m: milli; mol: mole; M: molar; MeOH: methanol; Me: methyl; min: minute; ESI-MS: electrospray ionization mass spectrometry; N: normality of solution; NaN₃: sodium azide; NaCl: sodium chloride; NaHCO₃: sodium hydrogenocarbonate; Na₂CO₃: sodium carbonate; NaOH: sodium hydroxide; Na₂SO₄: sodium sulfate; PBS: phosphate buffer saline; PGD₂: prostaglandin D2; PMSF: phenyl methanesulfonyl fluoride; POCl₃: phosphorous oxychloride; THF: tetrahydrofuran; $t_R$: retention time; Tris: tris-(hydroxymethyl)aminomethane buffer.

Analytical HPLC Conditions as Used in the Examples Below

LC-1: Analytical HPLC on a Xterra™ MS C₁₈ column (50×2.1 mm, 5 μm, Waters):

Linear gradient of water/0.06% formic acid (A) and acetonitrile/0.06% formic acid (B) from 5% to 95% B over 6 min; flow rate 0.25 ml/min, detection at 215 nm.

LC-2: Analytical HPLC on a GromSil MS C₁₈ column (50×2.1 mm, 5 μm, Waters):

Linear gradient of water/0.06% formic acid (A) and acetonitrile/0.06% formic acid (B) from 5% to 95% B over 6 min; flow rate 0.25 ml/min, detection at 215 nm.

LC-3: Analytical HPLC on a Waters Xterra™ MS C18 column (4.6×50 mm, 5 mm):

Linear gradient of water/0.06% formic acid (A) and acetonitrile/0.06% formic acid (B) from 5% to 95% B over 1 min; flow rate 3 ml/min.

LC-4: Analytical HPLC on a Zorbax SB-AQ column (4.6×50 mm, 5 mm):

Linear gradient of water/0.06% formic acid (A) and acetonitrile/0.06% formic acid (B) from 5% to 95% B over 1 min; flow rate 3 ml/min.

LC-5: Analytical HPLC on a Zorbax SB-AQ column (50×4.6 mm, 5 mm, Agilent 1100 equipped with a binary pump Dionex P580, a Photodiode Array Detector Dionex PDA-100 and a mass spectrometer Finnigan AQA):

Linear gradient of water/0.04% TFA (A) and acetonitrile (B) from 5% to 95% B over 1 min; flow rate 4.5 ml/min, detection at 210, 220, 230, 254 and 280 nm.

Synthesis of Precursors A-G of Formula 4

Precursor A: 1-ethoxycarbonylmethyl-3-pyrrolidin-1-ylmethylene-3H-indolium bromide

A-a) 3-Pyrrolidin-1-yl-methylene-3H-indole

In a round bottom flask equipped with a Dean-Starck condenser, 1H-indole-3-carbaldehyde (40 g, 0.275 mmol) and pyrrolidine (27 ml, 0.330 mmol) were suspended in toluene (480 ml) and kept heating at reflux overnight. After cooling to rt, the solid was filtered off, washed with toluene and recrystallized from THF (100 ml) affording subtitle compound (47.7 g) as a reddish solid in 87% yield.

$t_R$ (LC-2): 0.47 min; ESI-MS(+): m/z 199.46 [M+H]$^+$ (calcd 198.26 for $C_{13}H_{14}N_2$).

A-b) 1-Ethoxycarbonylmethyl-3-pyrrolidin-1-ylmethylene-3H-indolium bromide

Ethyl bromoacetate (6.1 ml, 55.4 mmol) was added dropwise to a stirred solution of 3-pyrrolidin-1-yl-methylene-3H-indole (10 g, 50.4 mmol) in EtOH (40 ml) and the reaction mixture was kept stirring at rt overnight. The solid was filtered off, washed with small portions of EtOH and then dried in vacuo, affording title compound (17 g) as a beige solid in 93% yield. $t_R$ (LC-1): 1.45 min; ESI-MS(+): m/z 285.31 [M]$^+$ (calcd 285.36 for $C_{17}H_{21}BrN_2O_2^+$).

Precursor B: 5-bromo-1-ethoxycarbonylmethyl-3-pyrrolidin-1-ylmethylene-3H-indolium bromide The title compound is prepared using a procedure analogous to Precursor A, substituting 5-bromo-1H-indole-3-carbaldehyde for 1H-indole-3-carbaldehyde. $t_R$ (LC-2): 1.52 min; ESI-MS(+): m/z 365.10 [M+H]$^+$ (calcd 364.26 for $C_{17}H_{20}BrN_2O_2^+$).

Preparation of 5-bromo-1H-indole-3-carbaldehyde

Dry DMF (7.5 ml) is cooled to 0° C. and treated dropwise with POCl$_3$ (3.66 ml, 40 mmol). After stirring at this temperature for 15 min, a solution of 5-bromo-1H-indole (784 mg, 4 mmol) in dry DMF (2 ml) is added and the reaction mixture is allowed to warm to rt within 1 h. Stirring is continued at 40° C. for an additional hour, then the reaction mixture is cooled to rt and poured onto ice. Aqueous NaOH solution is added to neutralize the acidic solution, adjusting to pH 6. After stirring overnight at rt, the precipitate was collected by filtration, washed with water and dried under high vacuum to give pure subtitle compound (932 mg) as a beige solid in quantitative yield.

$t_R$ (LC-2): 1.85 min; ESI-MS(+): m/z 226.10 [M+2]$^+$ (calcd 224.05 for $C_9H_6BrNO$).

Precursor C: 1-Ethoxycarbonylmethyl-7-methyl-3-pyrrolidin-1-ylmethylene-3H-indolium bromide The title compound is prepared using a procedure analogous to the preparation procedure for Precursor B, substituting 7-methyl-1H-indole-3-carbaldehyde for 5-bromo-1H-indole-3-carbaldehyde. Preparation of 7-methyl-1H-indole-3-carbaldehyde is performed analogous to 5-bromo-1H-indole-3-carbaldehyde. $t_R$ (LC-1) 1.56 min; ESI-MS(+): m/z 299.47 [M]$^+$ (calcd 299.39 for $C_{18}H_{23}N_2O_2^+$).

Precursor D: 1-Ethoxycarbonylmethyl-5-fluoro-3-pyrrolidin-1-ylmethylene-3H-indolium bromide The title compound is prepared using a procedure analogous to the preparation procedure for Precursor B, substituting 5-fluoro-1H-indole-3-carbaldehyde for 5-bromo-1H-indole-3-carbaldehyde. Preparation of 5-fluoro-1H-indole-3-carbaldehyde is performed analogous to 5-bromo-1H-indole-3-carbaldehyde. $t_R$ (LC-2) 1.45 min; ESI-MS(+): m/z 303.26 [M]$^+$ (calcd 303.35 for $C_{17}H_{20}FN_2O_2^+$).

Precursor E: 1-Ethoxycarbonylmethyl-5-methyl-3-pyrrolidin-1-ylmethylene-3H-indolium bromide The title compound is prepared using a procedure analogous to the preparation procedure for Precursor A, substituting 5-methyl-1H-indole-3-carbaldehyde for 1H-indole-3-carbaldehyde. Preparation of 5-methyl-1H-indole-3-carbaldehyde is performed analogous to 5-bromo-1H-indole-3-carbaldehyde. $t_R$ (LC-2) 1.46 min; ESI-MS(+): m/z 299.25 [M]$^+$ (calcd 299.39 for $C_{18}H_{23}N_2O_2^+$).

Precursor F: 1-Ethoxycarbonylmethyl-6-fluoro-3-pyrrolidin-1-ylmethylene-3H-indolium bromide The title compound is prepared using a procedure analogous to the preparation procedure for Precursor A, substituting 6-fluoro-1H-indole-3-carbaldehyde for 1H-indole-3-carbaldehyde. Preparation of 6-fluoro-1H-indole-3-carbaldehyde is performed analogous to 5-bromo-1H-indole-3-carbaldehyde. $t_R$ (LC-2): 1.45 min; ESI-MS(+): m/z 303.26 [M]$^+$ (calcd 303.35 for $C_{17}H_{20}FN_2O_2^+$).

Precursor G: 1-Ethoxycarbonylmethyl-6-nitro-3-pyrrolidin-1-ylmethylene-3H-indolium bromide The title compound is prepared using a procedure analogous to the preparation procedure for Precursor A, substituting 6-nitro-1H-indole-3-carbaldehyde for 1H-indole-3-carbaldehyde. Preparation of 6-nitro-1H-indole-3-carbaldehyde is performed analogous to 5-bromo-1H-indole-3-carbaldehyde. $t_R$ (LC-2): 1.37 min; ESI-MS(+): m/z 330.26 [M]$^+$ (calcd 330.36 for $C_{17}H_{20}N_3O_4^+$).

Preparation of Intermediates A-G of Formula 7

Intermediate A: Ethyl[3-(2-chlorocarbonyl-2-cyano-vinyl)-indol-1-yl]-acetate To a stirred suspension of 2-cyano-3-(1-ethoxycarbonylmethyl-1H-indol-3-yl)-acrylic acid (3.0 g, 10 mmol) in dry dichloromethane (120 ml), in the presence of a few drops of dry DMF, was added oxalyl chloride (1.7 ml, 20 mmol). After stirring at rt overnight, the volatiles were removed under reduced pressure, the residue azeotoped twice with dry toluene and dried in vacuo, affording crude title compound (3.18 g) in quantitative yield. This material was stored under argon and was used without further purification.

A-c) 2-Cyano-3-(1-ethoxycarbonylmethyl-1H-indol-3-yl)-acrylic acid

To a stirred solution of Precursor A (1-ethoxycarbonylmethyl-3-pyrrolidin-1-yl-methylene-3H-indolium bromide, 4.0 g, 10.8 mmol) and tert-butyl cyanoacetate (15.0 g, 10.8 mmol) in chloroform (100 ml) was added dropwise a solution of sodium ethylate (0.74 g, 10.8 mmol) in dry EtOH (40 ml). The reaction mixture was kept stirring at rt overnight, then diluted with EtOAc (60 ml) and water (30 ml), acidified to pH 3 by adding 1N aqueous HCl. After phase separation, the aqueous phase was extracted twice with EtOAc. The combined organic layers were washed with water and brine, dried over $Na_2SO_4$, and the solvent removed under reduced pressure. The residue was dissolved in dichloromethane (20 ml) and treated with trifluoroacetic acid (8.3 ml, 108 mmol) at rt for 4 h. The volatiles were removed under reduced pressure and the residue was azeotoped three times with toluene, then re-crystallized from EtOAc affording subtitle compound (3.15 g) as a yellow solid in 97% yield: $t_R$ (LC-2) 1.98 min; ESI-MS(+): m/z 324.35 [M+Na]$^+$ (calcd 298.29 for $C_{16}H_{14}N_2O_4$).

Intermediate B: Ethyl[3-(2-chlorocarbonyl-2-cyano-vinyl)-5-bromo-indol-1-yl]-acetate The title compound is prepared using a procedure analogous to Intermediate A, substituting Precursor B (5-bromo-1-ethoxycarbonylmethyl-3-pyrrolidin-1-ylmethylene-3H-indolium) for Precursor A.

Intermediate C: Ethyl[3-(2-chlorocarbonyl-2-cyano-vinyl)-7-methyl-indol-1-yl]-acetate The title compound is prepared using a procedure analogous to Intermediate A, substituting Precursor C for Precursor A.

Intermediate D: Ethyl[3-(2-chlorocarbonyl-2-cyano-vinyl)-5-fluoro-indol-1-yl]-acetate The title compound is prepared using a procedure analogous to Intermediate A, substituting Precursor D for Precursor A.

Intermediate E: Ethyl[3-(2-chlorocarbonyl-2-cyano-vinyl)-5-methyl-indol-1-yl]-acetate The title compound is prepared using a procedure analogous to Intermediate A, substituting Precursor E for Precursor A.

Intermediate F: Ethyl[3-(2-chlorocarbonyl-2-cyano-vinyl)-6-fluoro-indol-1-yl]-acetate The title compound is prepared using a procedure analogous to Intermediate A, substituting Precursor F for Precursor A.

Intermediate G: Ethyl[3-(2-chlorocarbonyl-2-cyano-vinyl)-6-nitro-indol-1-yl]-acetate The title compound is prepared using a procedure analogous to Intermediate A, substituting Precursor G for Precursor A.

Example 1

[3-((E)-2-Cyano-2-phenylcarbamoyl-vinyl)-indol-1-yl]-acetic acid

Step A: Ethyl[3-(2-cyano-2-phenylcarbamoyl-vinyl)-indol-1-yl]-acetate

Aniline (8 μl, 0.09 mmol) is added to a stirred solution of Intermediate A (25 mg, 0.08 mmol) and DIEA (41 μl, 0.24 mmol) in dry dichloromethane (1 ml). The reaction mixture is stirred at rt overnight, then is washed with 1N aqueous HCl, water and saturated aqueous $NaHCO_3$ solution. The solvent of the organic phase is removed yielding crude subtitle compound:

$t_R$ (LC-2) 2.18 min (single peak); ESI-MS(+): m/z 374.45 [M+H]$^+$ (calcd 373.40 for $C_{22}H_{19}N_3O_3$).

Step B)

A stirred solution of crude ethyl [3-(2-cyano-2-phenylcarbamoyl-vinyl)-indol-1-yl]-acetate (0.079 mmol) in THF (0.8 ml) is treated with 0.2N aqueous NaOH (0.4 ml, 0.08 mmol) at rt for 10 min. The yellow reaction mixture is diluted with water (2 ml) and washed twice with diethyl ether (2 ml). The aqueous phase is acidified to pH 1 by adding conc. HCl and extracted with dichloromethane. The solvent is evaporated and the residue is recrystallized from acetonitrile yielding pure title compound.

$t_R$ (LC-2) 1.91 min (single peak); ESI-MS(+): m/z 346.16 [M+H]$^+$ (calcd 345.35 for $C_{20}H_{15}N_3O_3$).

Alternatively to re-crystallization, final purification of the title compound is performed by column chromatography on silica gel (hexane/EtOAc 3:1, containing 2% of AcOH), or by preparative reversed-phase HPLC.

Alternatively, indolacetic acid derivatives of the general Formula I are prepared as described below for Example 107, starting with the respective Precursor B and 2-cyano-acetamide reagent of Formula NC—$CH_2$—$CONR^5R^6$.

Example 107

[5-Bromo-3-((E)-2-cyano-2-phenylcarbamoyl-vinyl)-indol-1-yl]-acetic acid

Step a) Ethyl[5-bromo-3-((E)-2-cyano-2-phenylcarbamoyl-vinyl)-indol-1-yl]-acetate A mixture of 2-cyano-N-phenyl-acetamide (122 mg, 0.14 mmol) and sodium ethylate (9.3 mg, 0.14 mmol) in dry ethanol (1 ml) is ultra-sonicated for 2 min and then added to a solution of Precursor B (50 mg, 0.14 mmol) in dry ethanol (1 ml). The reaction mixture is stirred at rt for 15 min, the precipitate is filtered off and washed twice with a small amount of ethanol. Pure subtitle compound is obtained as a brownish solid (24 mg) in 39% yield: $t_R$ (LC-2) 2.51 min; ESI-MS(+): m/z 454.09 [M+2]$^+$ (calcd 452.30 for $C_{22}H_{18}BrN_3O_3$).

Step b)

The title compound is obtained using conditions for the hydrolysis of the above ester analogous to Example 1.

$t_R$ (LC-2) 2.25 min; ESI-MS(+): m/z 424.08 [M+H]$^+$ (calcd 423.03 for $C_{20}H_{14}BrN_3O_3$).

Preparation of 2-cyano-acetamide reagents of Formula NC—$CH_2$—$CONR^5R^6$ 2-cyano-N-phenyl-acetamide Cyanoacetic acid (1.0 g, 11.7 mmol) is added to a stirred suspension of $PCl_5$ (2.4 g, 11.7 mmol) in dry dichloromethane (200 ml). The reaction mixture is heated to reflux and kept stirring for 30 min. After cooling to rt, aniline (1.07 ml, 11.7 mmol) is added dropwise and the reaction is stirred at reflux for additional 2 h, then cooled to 0° C. and neutralized by addition of aqueous saturated $Na_2CO_3$ solution. The precipitate is filtered off, washed with water and dried under high vacuum to give title compound (1.54 g) as a white solid in 82% yield: $t_R$ (LC-2) 1.50 min; ESI-MS(+): m/z 183.33 [M+Na]$^+$ (calcd 160.17 for $C_9H_8N_2O$).

Other Useful 2-cyano-acetamide reagents

The following 2-cyano-acetamide reagents were prepared using a procedure analogous to the preparation of 2-cyano-N-phenyl-acetamide, substituting the appropriate amine for aniline:

| Compound | Formula Mol Weight | $t_R$ [min] (Method) | MS Data m/z [M + H]$^+$ |
|---|---|---|---|
| 2-cyano-N-(4-fluoro-phenyl)-N-methyl-acetamide | C10H9N2OF 192.19 | 1.65 (LC-1) | 193.14 |
| 2-cyano-N-cyclohexyl-N-phenyl-acetamide | C15H18N2O 242.30 | 2.12 (LC-2) | 243.22 |
| N-butyl-2-cyano-N-phenyl-acetamide | C13H16N2O 216.30 | 2.00 (LC-2) | 217.19 |
| N-benzyl-2-cyano-N-phenyl-acetamide | C16H14N2O 250.30 | 2.02 (LC-2) | 251.18 |
| 3-(10,11-dihydro-dibenzo[b,f]azepin-5-yl)-3-oxo-propionitrile | C17H14N2O 262.31 | 2.00 (LC-2) | 263.15 |
| 3-(3,4-dihydro-2H-quinolin-1-yl)-3-oxo-propionitrile | C12H12N2O 200.24 | 1.73 (LC-2) | 201.21 |
| 3-(2-chloro-phenothiazin-10-yl)-3-oxo-propionitrile | C15H9N2SOCl 300.77 | 2.22 (LC-2) | 301.03 |
| 2-cyano-N-phenyl-N-thiophen-3-ylmethyl-acetamide | C14H12N2OS 256.33 | 1.01 (LC-4) | 256.89 |
| 2-cyano-N-(2,2-diphenyl-ethyl)-N-phenyl-acetamide | C23H2ON2O 340.42 | 1.15 (LC-4) | 341.97 |
| 3-(6,11-dihydro-dibenzo[b,e]azepin-5-yl)-3-oxo-propionitrile | C17H14N2O 262.31 | 1.03 (LC-4) | 363.26 |
| 2-cyano-N-(3-fluoro-phenyl)-N-methyl-acetamide | C10H9FN2O 192.19 | 0.88 (LC-3) | 192.94 |
| 2-cyano-N-methyl-N-(2-trifluoromethyl-phenyl)-acetamide | C11H9F3N2O 242.20 | 0.98 (LC-3) | 242.97 |
| 2-cyano-N-(3,4-dichloro-phenyl)-N-methyl-acetamide | C10H8Cl2N2O 243.09 | 0.99 (LC-4) | 242.98 |
| 2-cyano-N-(2,4-difluoro-phenyl)-N-methyl-acetamide | C10H8F2N2O 210.18 | 0.91 (LC-3) | 210.21 |
| 3-(3,4-dihydro-1H-isoquinolin-2-yl)-3-oxo-propionitrile | C12H12N2O 200.24 | 0.89 (LC-4) | 201.12 |
| 3-oxo-3-(7-trifluoromethyl-3,4-dihydro-2H-quinolin-1-yl)-propionitrile | C13H11F3N2O 268.23 | 1.03 (LC-4) | 268.87 |
| 2-cyano-N-ethyl-N-(4-trifluoromethoxy-phenyl)-acetamide | C12H11F3N2O2 272.22 | 1.10 (LC-3) | 272.77 |
| 3-(5,11-dihydrodibenzo[b,e] [1,4]oxazepin-5-yl)-3-oxo-propionitrile | C16H12N2O2 264.28 | 1.01 (LC-4) | 264.95 |

Phenethyl-phenyl-amine
(HNR11R12 for Example 84)

Sodium triacetoxyborohydride (5.46 g, 26 mmol) is added in small portions to a stirred solution of aniline (2.0 g, 21.5 mmol) and phenylacetaldehyde (2.83 g, 24 mmol) in dry DMF/MeOH/AcOH (87:10:3, 120 ml). After stirring at rt for 90 min, the volatiles are removed under reduced pressure. The residue is dissolved in dichloromethane (200 ml) and extracted twice with 1 N HCl. The combined aqueous layers are washed with EtOAc, then ammonium hydroxide solution is added to pH 9, and the mixture is extracted with dichloromethane. The solvent is evaporated, and the crude product is purified by silica gel chromatography (hexane/EtOAc, 5:1) affording pure title compound as a yellow oil.

$t_R$ (LC-2) 2.16 min; ESI-MS (positive ion) m/z 198.22 [M+H]$^+$ (calcd 197.28 for $C_{14}H_{15}N$).

5,6,11,12-tetrahydro-dibenzo[b,f]azocine
(HNR11R12 for Example 85)

To a suspension of 11,12-dihydro-5H-dibenzo[b,f]azocin-6-one (2.0 g, 8.96 mmol) in dry THF (20 ml) is added dropwise a solution of LiAlH$_4$ (1.0 N in THF, 8.96 ml) over a period of 10 min. After ceasing of gas evolution, the reaction mixture is kept stirring at reflux overnight, then quenched by the addition of water (0.48 ml). The precipitate is filtered off and the filtrate is extracted twice with EtOAc. The combined organic layers are dried over Na$_2$SO$_4$, the solvent is evaporated and the residue recrystallized from boiling hexane to give off white crystals of the title compound (1.35 g) in 72% yield: $t_R$ (LC-2) 1.65 min; ESI-MS(+): m/z 210.70 [M+H]$^+$ (calcd 209.29 for $C_{15}H_{15}N$).

6,11-Dihydro-5H-dibenzo[b,e]azepine (HNR11R12 for Example 89)

Step i) 5,11-Dihydro-dibenzo[b,e]azepin-6-one

A suspension of anhydrous aluminum chloride (319 mg, 2.39 mmol) in o-xylene is heated to 110° C. Then, a solution of 2-benzylphenylisocyanate (500 mg, 2.39 mmol) is added dropwise and the brown reaction mixture is kept stirring at 150° C. during 1 h. After cooling to rt, the solvent is evaporated, the residue is dissolved in dichloromethane/methanol (19:1) and filtered through a small plug of silica gel. The solvent is evaporated and the crude product is recrystallized from acetonitrile to give pure subtitle compound as a beige solid (170 mg) in 34% yield (Warawa et al., *J. Med. Chem.* 2001, 44, 372-389): $t_R$ (LC-2) 1.87 min; ESI-MS(+): m/z 210.13 [M+H]$^+$ (calcd 209.24 for $C_{14}H_{11}NO$).

Step ii)

To a stirred solution of 55,11-dihydro-dibenzo[b,e]azepin-6-one (170 mg, 0.81 mmol) in dry THF (20 ml) is added dropwise a solution of LiAlH$_4$ (1.0 N in THF, 0.81 mmol) over a period of 10 min. After ceasing of gas evolution the reaction mixture is kept stirring at reflux overnight, cooled to rt and poured onto water (100 ml). The mixture is extracted with diethyl ether, the combined organic layers are dried over $Na_2SO_4$ and the solvent removed under reduced pressure. The residue is recrystallized from boiling hexane affording title compound as an off white solid (130 mg) in 82% yield: $t_R$ (LC-2) 2.09 min; ESI-MS(+): m/z 197.33 $[M+2H]^+$ (calcd 195.26 for $C_{14}H_{13}N$).

Diphenethyl-amine (HNR11R12 for Example 90)

Sodiumtriacetoxyborohydride (8.87 g, 41.3 mmol) is added in small portions at 0° C. to a stirred solution of phenethylamine (5.0 g, 41.3 mmol) and phenylacetaldehyde (4.96 g, 41.3 mmol) in methanol (50 ml). The reaction mixture is stirred at rt overnight, poured onto saturated aqueous $KH_2PO_4$ solution and extracted twice with EtOAc. The solvent is evaporated, the residue is taken up in 1N HCl and washed twice with dichloromethane. The aqueous layer is adjusted to pH 9 by the addition of ammonium hydroxide solution and extracted with dichloromethane. Drying the combined organic layers over $Na_2SO_4$ and evaporating the solvents give crude title compound as a pale yellow oil.

$t_R$ (LC-2) 1.40 min; ESI-MS(+): m/z 226.23 $[M+H]^+$ (calcd 225.33 for $C_{16}H_{19}N$).

Examples 2-106 and 108-156 of the following Tables 1 to 8 are prepared using a procedure analogous to that described for Example 1, substituting the appropriate amine for aniline and the appropriate Intermediate for Intermediate A respectively; or analogous to that described for Example 107, substituting the appropriate 2-cyano-acetamide for 2-cyano-N-phenyl-acetamide and the appropriate Precursor for Precursor B.

TABLE 1

Examples 1-106 with the general structure of

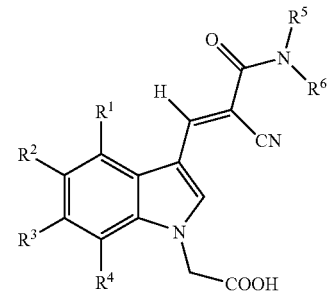

I

| Ex. | Name | $R^5$ | $R^6$ | Formula Mol weight | $t_R$ [min] (Meth.) | MS Data m/z $[M + H]^+$ |
|---|---|---|---|---|---|---|
| 1 | [3-((E)-2-cyano-2-phenylcarbamoyl-vinyl)-indol-1-yl]-acetic acid | H | phenyl | C20H15N3O3 345.357 | 1.91 (LC-2) | 346.16 |
| 2 | [3-((E)-2-cyano-2-m-tolylcarbamoyl-vinyl)-indol-1-yl]-acetic acid | H | 3-methyl-phenyl | C21H17N3O3 359.384 | 2.22 (LC-1) | 260.20 |
| 3 | {3-[(E)-2-cyano-2-(4-methoxy-phenylcarbamoyl)-vinyl]-indol-1-yl}-acetic acid | H | 4-methoxy-phenyl | C21H17N3O4 375.383 | 2.10 (LC-1) | 376.25 |
| 4 | {3-[(E)-2-(3-bromo-phenylcarbamoyl)-2-cyano-vinyl]-indol-1-yl}-acetic acid | H | 3-bromo-phenyl | C20H14N3O3Br 424.253 | 2.34 (LC-1) | 426.00 |
| 5 | {3-[(E)-2-cyano-2-(cyclohexylmethyl-carbamoyl)-vinyl]-indol-1-yl}-acetic acid | H | cyclohexyl-methyl | C21H23N3O3 365.432 | 2.08 (LC-2) | 366.24 |
| 6 | [3-((E)-2-cyano-2-phenethylcarbamoyl-vinyl)-indol-1-yl]-acetic acid | H | phenethyl | C22H19N3O3 373.411 | 1.94 (LC-2) | 374.20 |
| 7 | [3-((E)-2-cyano-2-isopropylcarbamoyl-vinyl)-indol-1-yl]-acetic acid | H | isopropyl | C17H17N3O3 311.34 | 1.73 (LC-2) | 312.34 |
| 8 | [3-((E)-2-cyano-2-propylcarbamoyl-vinyl)-indol-1-yl]-acetic acid | H | propyl | C17H17N3O3 311.34 | 1.73 (LC-2) | 312.23 |
| 9 | [3-((E)-2-cyano-2-cyclohexylcarbamoyl-vinyl)-indol-1-yl]-acetic acid | H | cyclohexyl | C20H21N3O3 351.405 | 1.96 (LC-2) | 352.26 |

TABLE 1-continued

Examples 1-106 with the general structure of

I

| Ex. | Name | R⁵ | R⁶ | Formula Mol weight | $t_R$ [min] (Meth.) | MS Data m/z [M + H]⁺ |
|---|---|---|---|---|---|---|
| 10 | {3-[(E)-2-cyano-2-(3-methyl butylcarbamoyl)-vinyl]-indol-1-yl}-acetic acid | H | 3-methyl-butyl | C19H21N3O3 339.394 | 1.96 (LC-2) | 340.20 |
| 11 | [3-((E)-2-benzylcarbamoyl-2-cyano-vinyl)-indol-1-yl]-acetic acid | H | benzyl | C21H17N3O3 359.384 | 1.91 (LC-2) | 360.21 |
| 12 | {3-[(E)-2-(benzyl-phenyl-carbamoyl)-2-cyano-vinyl]-indol-1-yl}-acetic acid | phenyl | benzyl | C27H21N3O3 435.482 | 2.34 (LC-1) | 436.26 |
| 13 | {3-[(E)-2-cyano-2-(4-cyano-phenylcarbamoyl)-vinyl]-indol-1-yl}-acetic acid | H | 4-cyano-phenyl | C21H14N4O3 370.367 | 2.15 (LC-1) | 371.09 |
| 14 | [3-((E)-2-cyano-2-o-tolylcarbamoyl-vinyl)-indol-1-yl]-acetic acid | H | o-tolyl | C21H17N3O3 359.384 | 2.14 (LC-1) | 360.26 |
| 15 | {3-[(E)-2-cyano-2-(4-ethyl-phenylcarbamoyl)-vinyl]-indol-1-yl}-acetic acid | H | 4-ethyl-phenyl | C22H19N3O3 373.411 | 2.33 (LC-1) | 374.21 |
| 16 | {3-[(E)-2-cyano-2-(4-fluoro-phenylcarbamoyl)-vinyl]-indol-1-yl}-acetic acid | H | 4-fluoro-phenyl | C20H14N3O3F 363.347 | 2.16 (LC-1) | 364.21 |
| 17 | {3-[(E)-2-cyano-2-(4-phenoxy-phenylcarbarnoyl)-vinyl]-indol-1-yl}-acetic acid | H | 4-phenoxy-phenyl | C26H19N3O4 437.454 | 2.42 (LC-1) | 438.30 |
| 18 | {3-[(E)-2-cyano-2-(naphthalen-2-ylcarbamoyl)-vinyl]-indol-1-yl}-acetic acid | H | naphthalen-2-yl | C24H17N3O3 395.417 | 2.33 (LC-1) | 396.32 |
| 19 | {3-[(E)-2-cyano-2-(2-isopropyl-phenylcarbamoyl)-vinyl]-indol-1-yl}-acetic acid | H | 2-isopropyl-phenyl | C23H21N3O3 387.438 | 2.27 (LC-1) | 388.23 |
| 20 | [3-((E)-2-cyano-2-p-tolylcarbamoyl-vinyl)-indol-1-yl]-acetic acid | H | p-tolyl | C21H17N3O3 359.384 | 2.23 (LC-1) | 360.26 |
| 21 | {3-[(E)-2-cyano-2-(4-isopropyl-phenylcarbamoyl)-vinyl]-indol-1-yl}-acetic acid | H | 4-isopropyl-phenyl | C23H21N3O3 387.438 | 2.40 (LC-1) | 388.29 |

TABLE 1-continued

Examples 1-106 with the general structure of

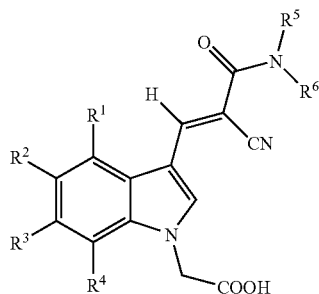

| Ex. | Name | R⁵ | R⁶ | Formula Mol weight | $t_R$ [min] (Meth.) | MS Data m/z [M + H]⁺ |
|---|---|---|---|---|---|---|
| 22 | {3-[(E)-2-cyano-2-(3-methoxy-phenylcarbarnoyl)-vinyl]-indol-1-yl}-acetic acid | H | 3-methoxy-phenyl | C21H17N3O4 375.383 | 2.16 (LC-1) | 376.12 |
| 23 | {3-[(E)-2-cyano-2-(3-fluoro-phenylcarbamoyl)-vinyl]-indol-1-yl}-acetic acid | H | 3-fluoro-phenyl | C20H14N3O3F 363.347 | 2.21 (LC-1) | 364.15 |
| 24 | {3-[(E)-2-cyano-2-(9H-fluoren-2-ylcarbamoyl)-vinyl]-indol-1-yl}-acetic acid | H | 9H-fluoren-2-yl | C27H19N3O3 433.466 | 2.47 (LC-1) | 434.22 |
| 25 | {3-[(E)-2-cyano-2-(4-propyl-phenylcarbamoyl)-vinyl]-indol-1-yl}-acetic acid | H | 4-propyl-phenyl | C23H21N3O3 387.438 | 2.43 (LC-1) | 388.16 |
| 26 | {3-[(E)-2-(biphenyl-4-ylcarbamoyl)-2-cyano-vinyl]-indol-1-yl}-acetic acid | H | biphenyl-4-yl | C26H19N3O3 421.455 | 2.44 (LC-1) | 422.24 |
| 27 | {3-[(E)-2-cyano-2-(3,2'-dimethyl-biphenyl-4-ylcarbamoyl)-vinyl]-indol-1-yl}-acetic acid | H | 3,2'-dimethyl-biphenyl-4-yl | C28H23N3O3 449.509 | 2.53 (LC-1) | 450.15 |
| 28 | {3-[(E)-2-(4-tert-butyl-phenylcarbamoyl)-2-cyano-vinyl]-indol-1-yl}-acetic acid | H | 4-tert-butyl-phenyl | C24H23N3O3 401.465 | 2.46 (LC-1) | 402.24 |
| 29 | {3-[(E)-2-(2-benzyl-phenylcarbamoyl)-2-cyano-vinyl]-indol-1-yl}-acetic acid | H | 2-benzyl-phenyl | C27H21N3O3 435.482 | 2.35 (LC-1) | 436.13 |
| 30 | {3-[(E)-2-(4-butyl-phenylcarbamoyl)-2-cyano-vinyl]-indol-1-yl}-acetic acid | H | 4-butyl-phenyl | C24H23N3O3 401.465 | 2.52 (LC-1) | 402.37 |
| 31 | {3-[(E)-2-(2-acetyl-phenylcarbamoyl)-2-cyano-vinyl]-indol-1-yl}-acetic acid | H | 2-acetyl-phenyl | C22H17N3O4 387.394 | 2.24 (LC-1) | 388.16 |
| 32 | {3-[(E)-2-cyano-2-(indan-5-ylcarbamoyl)-vinyl]-indol-1-yl}-acetic acid | H | indan-5-yl | C23H19N3O3 385.422 | 2.36 (LC-1) | 386.19 |
| 33 | {3-[(E)-2-(4-sec-butyl-phenylcarbamoyl)-2-cyano-vinyl]-indol-1-yl}-acetic acid | H | 4-sec-butyl-phenyl | C24H23N3O3 401.465 | 2.51 (LC-1) | 402.24 |
| 34 | {3-[(E)-2-cyano-2-(4-ethoxy-phenylcarbamoyl)-vinyl]-indol-1-yl}-acetic acid | H | 4-ethoxy-phenyl | C22H19N3O4 389.41 | 2.20 (LC-1) | 390.20 |

TABLE 1-continued

Examples 1-106 with the general structure of

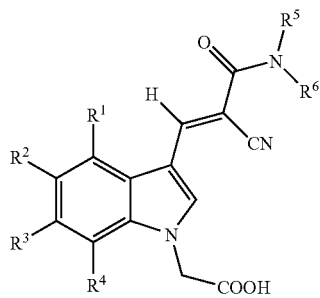

I

| Ex. | Name | R⁵ | R⁶ | Formula Mol weight | $t_R$ [min] (Meth.) | MS Data m/z [M + H]⁺ |
|---|---|---|---|---|---|---|
| 35 | {3-[(E)-2-cyano-2-(3-ethoxy-phenylcarbamoyl)-vinyl]-indol-1-yl}-acetic acid | H | 3-ethoxy-phenyl | C22H19N3O4 389.41 | 2.25 (LC-1) | 390.14 |
| 36 | {3-[(E)-2-cyano-2-(2-propyl phenylcarbamoyl)-vinyl]-indol-1-yl}-acetic acid | H | 2-propyl-phenyl | C23H21N3O3 387.438 | 2.33 (LC-1) | 388.23 |
| 37 | {3-[(E)-2-cyano-2-(3-phenoxy-phenylcarbamoyl)-vinyl]-indol-1-yl}-acetic acid | H | 3-phenoxy-phenyl | C26H19N3O4 437.454 | 2.44 (LC-1) | 438.18 |
| 38 | {3-[(E)-2-cyano-2-(3-ethyl-phenylcarbamoyl)-vinyl]-indol-1-yl}-acetic acid | H | 3-ethyl-phenyl | C22H19N3O3 373.411 | 2.33 (LC-1) | 374.21 |
| 39 | {3-[(E)-2-cyano-2-(2-ethoxy phenylcarbamoyl)-vinyl]-indol-1-yl}-acetic acid | H | 2-ethoxy-phenyl | C22H19N3O4 389.41 | 2.39 (LC-1) | 390.20 |
| 40 | {3-[(E)-2-(3-benzyloxy-phenylcarbamoyl)-2-cyano-vinyl]-indol-1-yl}-acetic acid | H | 3-benzyloxy-phenyl | C27H21N3O4 451.481 | 2.42 (LC-1) | 452.19 |
| 41 | {3-[(E)-2-(4-bromo-phenylcarbamoyl)-2-cyano-vinyl]-indol-1-yl}-acetic acid | H | 4-bromo-phenyl | C20H14N3O3Br 424.253 | 2.33 (LC-1) | 424.09 |
| 42 | {3-[(E)-2-cyano-2-(4-iodo-phenylcarbamoyl)-vinyl]-indol-1-yl}-acetic acid | H | 4-iodo-phenyl | C20H14N3O3I 471.249 | 2.37 (LC-1) | 472.00 |
| 43 | {3-[(E)-2-cyano-2-(3-iodo-phenylcarbamoyl)-vinyl]-indol-1-yl}-acetic acid | H | 3-iodo-phenyl | C20H14N3O3I 471.249 | 2.37 (LC-1) | 472.00 |
| 44 | (3-{(E)-2-cyano-2-[(4-fluoro-phenyl)-methyl-carbamoyl]-vinyl}-indol-1-yl)-acetic acid | methyl | 4-fluoro-phenyl | C21H16N3O3F 377.374 | 2.08 (LC-1) | 378.22 |
| 45 | (3-{(E)-2-cyano-2-[(4-methoxy-phenyl)-methyl-carbamoyl]-vinyl}-indol-1-yl)-acetic acid | methyl | 4-methoxy-phenyl | C22H19N3O4 389.41 | 2.06 (LC-1) | 390.20 |
| 46 | {3-[(E)-2-cyano-2-(methyl-phenyl-carbamoyl)-vinyl]-indol-1-yl}-acetic acid | methyl | phenyl | C21H17N3O3 359.384 | 2.05 (LC-1) | 360.20 |

TABLE 1-continued

Examples 1-106 with the general structure of I

| Ex. | Name | R⁵ | R⁶ | Formula Mol weight | $t_R$ [min] (Meth.) | MS Data m/z [M + H]⁺ |
|---|---|---|---|---|---|---|
| 47 | {3-[(E)-2-cyano-3-(3,4-dihydro-2H-quinolin-1-yl)-3-oxo-propenyl]-indol-1-yl}-acetic acid | | 3,4-dihydro-2H-quinolin-yl | C23H19N3O3 385.422 | 2.16 (LC-1) | 386.25 |
| 48 | {3-[(E)-2-cyano-2-(methyl-p-tolyl-carbamoyl)-vinyl]-indol-1-yl}-acetic acid | methyl | p-tolyl | C22H19N3O3 373.411 | 2.14 (LC-1) | 374.21 |
| 49 | (3-{(E)-2-cyano-2-[2-(2,4-dichloro-phenoxy)-phenylcarbamoyl]-vinyl}-indol-1-yl)-acetic acid | H | 2,4-dichloro-phenoxy)-phenyl | C26H17N3O4Cl2 506.344 | 2.25 (LC-1) | 374.15 |
| 50 | {3-[(E)-2-cyano-2-(2,5-dimethyl-phenylcarbamoyl)-vinyl]-indol-1-yl}-acetic acid | H | 2,5-dimethyl-phenyl | C22H19N3O3 373.411 | 2.25 (LC-1) | 374.15 |
| 51 | {3-[(E)-2-cyano-2-(9-ethyl-9H-carbazol-3-ylcarbamoyl)-vinyl]-indol-1-yl}-acetic acid | H | 9-ethyl-9H-carbazol-3-yl | C28H22N4O3 462.508 | 2.48 (LC-1) | 463.21 |
| 52 | {3-[(E)-2-(3,5-bis-trifluoromethyl-phenylcarbamoyl)-2-cyano-vinyl]-indol-1-yl}-acetic acid | H | 3,5-bis-trifluoromethyl-phenyl | C22H13N3O3F6 481.351 | 2.56 (LC-1) | 482.07 |
| 53 | {3-[(E)-2-cyano-2-(5-methoxy-2-methyl-phenylcarbamoyl)-vinyl]-indol-1-}-acetic acid | H | 5-methoxy-2-methyl-phenyl | C22H19N3O4 389.41 | 2.16 (LC-1) | 390.14 |
| 54 | {3-[(E)-2-(3-benzoyl-phenylcarbamoyl)-2-cyano-vinyl]-indol-1-yl}-acetic acid | H | 3-benzoyl-phenyl | C27H19N3O4 449.465 | 2.33 (LC-1) | 450.09 |
| 55 | {3-[(E)-2-(4-benzyloxy-phenylcarbamoyl)-2-cyano-vinyl]-indol-1-yl}-acetic acid | H | 4-benzyloxy-phenyl | C27H21N3O4 451.481 | 2.40 (LC-1) | 452.19 |
| 56 | {3-[(E)-2-cyano-2-(3-nitro-phenylcarbamoyl)-vinyl]-indol-1-yl}-acetic acid | H | 3-nitro-phenyl | C20H14N4O5 390.354 | 2.20 (LC-1) | 391.09 |
| 57 | {3-[(E)-2-cyano-2-(9-oxo-9H-fluoren-2-ylcarbamoyl)-vinyl]-indol-1-yl}-acetic acid | H | 9-oxo-9H-fluoren-2-yl | C27H17N3O4 447.449 | 2.36 (LC-1) | 448.05 |
| 58 | {3-[(E)-2-cyano-2-(4-methoxy-biphenyl-3-ylcarbamoyl)-vinyl]-indol-1-yl}-acetic acid | H | 4-methoxy-biphenyl-3-yl | C27H21N3O4 451.481 | 2.56 (LC-1) | 452.12 |

TABLE 1-continued

Examples 1-106 with the general structure of

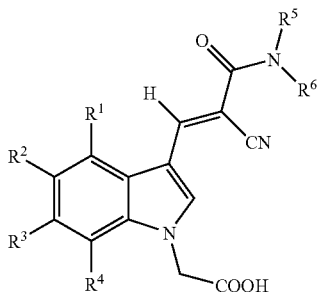

I

| Ex. | Name | R[5] | R[6] | Formula Mol weight | $t_R$ [min] (Meth.) | MS Data m/z [M + H]+ |
|---|---|---|---|---|---|---|
| 59 | {3-[(E)-2-cyano-2-(2-methoxy-dibenzofuran-3-ylcarbamoyl)-vinyl]-indol-1-yl}-acetic acid | H | 2-methoxy-dibenzofuran-3-yl | C27H19N3O5 465.464 | 2.63 (LC-1) | 466.14 |
| 60 | {3-[(E)-2-cyano-2-(9-oxo-9H-fluoren-4-ylcarbamoyl)-vinyl]-indol-1-yl}-acetic acid | H | 9-oxo-9H-fluoren-4-yl | C27H17N3O4 447.449 | 2.224 (LC-1) | 48.11 |
| 61 | {3-[(E)-2-cyano-2-(9-oxo-9H-fluoren-1-ylcarbamoyl)-vinyl]-indol-1-yl}-acetic acid | H | 9-oxo-9H-fluoren-1-yl | C27H17N3O4 447.449 | 2.22 (LC-1) | 448.11 |
| 62 | {3-[(E)-2-(2-benzoyl-phenylcarbamoyl)-2-cyano-vinyl]-indol-1-yl}-acetic acid | H | 2-benzoyl-phenyl | C27H19N3O4 449.465 | 2.43 (LC-1) | 450.15 |
| 63 | {3-[(E)-2-(3-chloro-4-methoxy-phenylcarbamoyl)-2-cyano-vinyl]-indol-1-yl}-acetic acid | H | 3-chloro-4-methoxy-phenyl | C21H16N3O4Cl 409.828 | 2.21 (LC-1) | 410.08 |
| 64 | {3-[(E)-2-(5-chloro-2-methoxy-phenylcarbarnoyl)-2-cyano-vinyl]-indol-1-yl}-acetic acid | H | 5-chloro-2-methoxy-phenyl | C21H16N3O4Cl 409.828 | 2.45 (LC-1) | 410.08 |
| 65 | 3-[(E)-3-(1-carboxymethyl-1H-indol-3-yl)-2-cyano-acryloylamino]-4-methyl-benzoic acid methyl ester | H | 2-methyl-5-methoxycarbonyl-phenyl | C23H19N3O5 417.42 | 2.15 (LC-1) | 418.10 |
| 66 | {3-[(E)-2-(4-chloro-2-methyl-phenylcarbamoyl)-2-cyano-vinyl]-indol-1-yl}-acetic acid | H | 4-chloro-2-methyl-phenyl | C21H16N3O3Cl 393.829 | 2.31 (LC-1) | 394.09 |
| 67 | 2-[(E)-3-(1-carboxymethyl-1H-indol-3-yl)-2-cyano-acryloylamino]-benzoic acid methyl ester | H | 2-methoxy-carbonyl-phenyl | C22H17N3O5 403.393 | 2.35 (LC-1) | 426.13 [M + Na]+ |
| 68 | {3-[(E)-2-cyano-2-(4-trifluoromethoxy-phenylcarbamoyl)-vinyl]-indol-1-yl}-acetic acid | H | 4-trifluoro-methoxy-phenyl | C21H14N3O4F3 429.353 | 2.37 (LC-1) | 430.08 |
| 69 | {3-[(E)-2-cyano-2-(3,5-dimethyl-phenylcarbamoyl)-vinyl]-indol-1-yl}-acetic acid | H | 3,5-dimethyl-phenyl | C22H19N3O3 373.411 | 2.33 (LC-1) | 374.15 |

TABLE 1-continued

Examples 1-106 with the general structure of

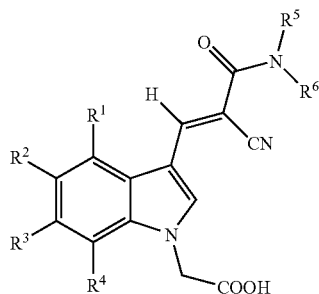

I

| Ex. | Name | R⁵ | R⁶ | Formula Mol weight | $t_R$ [min] (Meth.) | MS Data m/z [M + H]⁺ |
|---|---|---|---|---|---|---|
| 70 | {3-[(E)-2-(3-bromo-4-methyl-phenylcarbamoyl)-2-cyano-vinyl]-indol-1-yl}-acetic acid | H | 3-bromo-4-methyl-phenyl | C21H16N3O3Br 438.28 | 2.41 (LC-1) | 438.04 |
| 71 | {3-[(E)-2-(4-bromo-3-methyl-phenylcarbamoyl)-2-cyano-vinyl]-indol-1-yl}-acetic acid | H | 4-bromo-3-methyl-phenyl | C21H16N3O3Br 438.28 | 2.42 (LC-1) | 440.02 |
| 72 | 4-[(E)-3-(1-carboxymethyl-1H-indol-3-yl)-2-cyano-acryloylamino]-benzoic acid ethyl ester | H | 4-ethoxycarbonyl-phenyl | C23H19N3O5 417.42 | 2.27 (LC-1) | 418.10 |
| 73 | 3-[(E)-3-(1-carboxymethyl-1H-indol-3-yl)-2-cyano-acryloylamino]-benzoic acid methyl ester | H | 3-methoxycarbonyl-phenyl | C22H17N3O5 403.393 | 2.15 (LC-1) | 404.09 |
| 74 | {3-[(E)-2-cyano-2-(4-trifluoromethyl-phenylcarbamoyl)-vinyl]-indol-1-yl}-acetic acid | H | 4-trifluoromethyl-phenyl | C21H14N3O3F3 413.354 | 2.36 (LC-1) | 414.09 |
| 75 | {3-[(E)-2-cyano-2-(3,5-dimethoxy-phenylcarbamoyl)-vinyl]-indol-1-yl}-acetic acid | H | 3,5-dimethoxy-phenyl | C22H19N3O5 405.409 | 2.18 (LC-1) | 406.13 |
| 76 | {3-[(E)-2-(4-bromo-3-chloro-phenylcarbamoyl)-2-cyano-vinyl]-indol-1-yl}-acetic acid | H | 4-bromo-3-chloro-phenyl | C20H13N3O3BrCl 458.698 | 2.45 (LC-1) | 459.96 |
| 77 | {3-[(E)-2-(4-bromo-2-methyl-phenylcarbamoyl)-2-cyano-vinyl]-indol-1-yl}-acetic acid | H | 4-bromo-2-methyl-phenyl | C21H16N3O3Br 438.28 | 2.35 (LC-1) | 440.02 |
| 78 | {3-[(E)-2-(4-acetyl-phenylcarbamoyl)-2-cyano-vinyl]-indol-1-yl}-acetic acid | H | 4-acetyl-phenyl | C22H17N3O4 387.394 | 2.06 (LC-1) | 388.16 |
| 79 | {3-[(E)-2-(2-bromo-4-methyl-phenylcarbamoyl)-2-cyano-vinyl]-indol-1-yl}-acetic acid | H | 2-bromo-4-methyl-phenyl | C21H16N3O3Br 438.28 | 2.41 (LC-1) | 440.02 |
| 80 | {3-[(E)-2-(benzo[1,3]dioxol-5-ylcarbamoyl)-2-cyano-vinyl]-indol-1-yl}-acetic acid | H | benzo[1,3]dioxol-5-yl | C21H15N3O5 389.366 | 2.10 (LC-1) | 390.07 |

TABLE 1-continued

Examples 1-106 with the general structure of

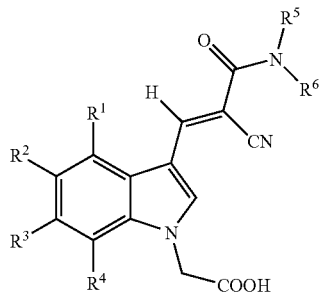

I

| Ex. | Name | R⁵ | R⁶ | Formula Mol weight | $t_R$ [min] (Meth.) | MS Data m/z $[M + H]^+$ |
|---|---|---|---|---|---|---|
| 81 | {3-[(E)-2-cyano-2-(2,3-dihydro-benzo[1,4]dioxin-6-ylcarbamoyl)-vinyl]-indol-1-yl}-acetic acid | H | 2,3-dihydro-benzo[1,4]dioxin-6-yl | C22H17N3O5 403.393 | 2.08 (LC-1) | 404.09 |
| 82 | {3-[(E)-2-cyano-2-(2-methoxy-phenylcarbamoyl)-vinyl]-indol-1-yl}-acetic acid | H | 2-methoxy-phenyl | C21H17N3O4 375.383 | 2.28 (LC-1) | 376.31 |
| 83 | {3-[(E)-2-cyano-2-(2-phenoxy-phenylcarbamoyl)-vinyl]-indol-1-yl}-acetic acid | H | 2-phenoxy-phenyl | C26H19N3O4 437.454 | 2.48 (LC-1) | 438.24 |
| 84 | sodium {3-[(E)-2-cyano-2-(phenethyl-phenyl-carbamoyl)-vinyl]-indol-1-yl}-acetate | phenyl | phenethyl | C28H22N3O3Na 471.491 | 2.37 (LC-1) | 450.15 |
| 85 | sodium {3-[(E)-2-cyano-3-(11,12-dihydro-6H-dibenzo[b,f]azocin-5-yl)-3-oxo-propenyl]-indol-1-yl}-acetate | 11,12-dihydro-6H-dibenzo[b,f]azocin-5-yl | | C29H22N3O3Na 483.502 | 2.33 (LC-1) | 462.19 |
| 86 | sodium [3-((E)-2-cyano-2-diphenylcarbamoyl-vinyl)-indol-1-yl]-acetate | phenyl | phenyl | C26H18N3O3Na 443.437 | 2.20 (LC-1) | 422.12 |
| 87 | sodium [3-((E)-2-cyano-3-dibenzo[b,f]azepin-5-yl-3-oxo-propenyl)-indol-1-yl]-acetate | dibenzo[b,f]azepin-5-yl | | C28H18N3O3Na 467.459 | 2.26 (LC-1) | 446.14 |
| 88 | sodium (3-{(E)-2-[(4-chloro-phenyl)-methyl-carbamoyl]-2-cyano-vinyl}-indol-1-yl)-acetate | methyl | 4-chloro-phenyl | C21H15N3O3ClNa 415.811 | 2.14 (LC-1) | 416.06 |
| 89 | {3-[(E)-2-cyano-3-(6,11-dihydro-dibenzo[b,e]azepin-5-yl)-3-oxo-propenyl]-indol-1-yl}-acetic acid | 6,11-dihydro-dibenzo[b,e]azepin-5-yl | | C28H21N3O3 447.493 | 2.31 (LC-1) | 448.24 |
| 90 | [3-((E)-2-cyano-2-diphenethylcarbamoyl-vinyl)-indol-1-yl]-acetic acid | phenethyl | phenethyl | C30H27N3O3 477.562 | 2.40 (LC-1) | 478.31 |
| 91 | {3-[(E)-2-cyano-3-(10,11-dihydro-dibenzo[b,f]azepin-5-yl)-3-oxo-propenyl]-indol-1-yl}-acetic acid | 10,11-dihydro-dibenzo[b,f]azepin-5-yl | | C28H21N3O3 447.493 | 2.27 (LC-1) | 448.30 |

TABLE 1-continued

Examples 1-106 with the general structure of

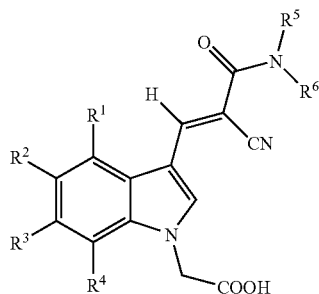

I

| Ex. | Name | R⁵ | R⁶ | Formula Mol weight | t_R [min] (Meth.) | MS Data m/z [M + H]⁺ |
|---|---|---|---|---|---|---|
| 92 | (3-{(E)-2-cyano-2-[methyl-((R)-1-phenyl-ethyl)-carbamoyl]-vinyl}-indol-1-yl)-acetic acid | methyl | (R)-1-phenyl-ethyl | C23H21N3O3 387.438 | 2.23 (LC-1) | 388.23 |
| 93 | {3-[(E)-2-(benzyl-methyl-carbamoyl)-2-cyano-vinyl]-indol-1-yl}-acetic acid | methyl | benzyl | C22H19N3O3 373.411 | 2.13 (LC-1) | 374.21 |
| 94 | (3-{(E)-2-[(4-acetyl-phenyl)-methyl-carbamoyl]-2-cyano-vinyl}-indol-1-yl)-acetic acid | methyl | 4-acetyl-phenyl | C23H19N3O4 401.421 | 2.00 (LC-1) | 402.18 |
| 95 | (3-{(E)-2-[(4-acetyl-phenyl)-furan-2-ylmethyl-carbamoyl]-2-cyano-vinyl}-indol-1-yl)-acetic acid | furan-2-ylmethyl | 4-acetyl-phenyl | C27H21N3O5 467.48 | 2.15 (LC-1) | 468.07 |
| 96 | {3-[(E)-2-(benzyl-carboxymethyl-carbamoyl)-2-cyano-vinyl]-indol-1-yl}-acetic acid | benzyl | carboxy-methyl | C23H19N3O5 417.42 | 2.01 (LC-1) | 416.19 [M − H]⁻ |
| 97 | 3-{benzyl-[(E)-3-(1-carboxymethyl-1H-indol-3-yl)-2-cyano-acryloyl]-amino}-propionic acid | benzyl | carboxyethyl | C24H21N3O5 431.447 | 1.97 (LC-1) | 432.18 432.18 |
| 98 | {3-[(E)-2-cyano-3-(2,3-dihydro-indol-1-yl)-3-oxo-propenyl]-indol-1-yl}-acetic acid | 2,3-dihydro-indol-1-yl | | C22H17N3O3 371.395 | 2.2 (LC-1) | 372.19 |
| 99 | {3-[(E)-2-(carboxymethyl-phenyl-carbamoyl)-2-cyano-vinyl]-indol-1-yl}-acetic acid | phenyl | carboxy-methyl | C22H17N3O5 403.393 | 1.86 (LC-1) | 402.11 [M − H]⁻ |
| 100 | (3-{(E)-2-cyano-2-[(2-cyano-ethyl)-phenyl-carbamoyl]-vinyl}-indol-1-yl)-acetic acid | phenyl | 2-cyano-ethyl | C23H18N4O3 398.421 | 2.01 (LC-1) | 399.18 |
| 101 | (3-{(E)-2-[(3-chloro-phenyl)-methyl-carbamoyl]-2-cyano-vinyl}-indol-1-yl)-acetic acid | methyl | 3-chloro-phenyl | C21H16N3O3Cl 393.829 | 2.14 (LC-1) | 394.15 |
| 102 | {3-[(E)-2-(allyl-phenyl-carbamoyl)-2-cyano-vinyl]-indol-1-yl}-acetic acid | phenyl | allyl | C23H19N3O3 385.422 | 2.18 (LC-1) | 386.19 |
| 103 | {3-[(E)-2-cyano-2-(cyclohexyl-phenyl-carbamoyl)-vinyl]-indol-1-yl}-acetic acid | phenyl | cyclohexyl | C26H25N3O3 427.503 | 2.43 (LC-1) | 428.23 |

TABLE 1-continued

Examples 1-106 with the general structure of

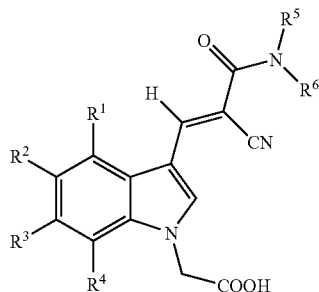

I

| Ex. | Name | R⁵ | R⁶ | Formula Mol weight | $t_R$ [min] (Meth.) | MS Data m/z [M + H]⁺ |
|---|---|---|---|---|---|---|
| 104 | {3-[(E)-2-cyano-2-(methyl-o-tolyl-carbamoyl)-vinyl]-indol-1-yl}-acetic acid | methyl | o-tolyl | C22H19N3O3 373.411 | 2.09 (LC-1) | 374.21 |
| 105 | {3-[(E)-2-cyano-2-(ethyl-phenyl-carbamoyl)-vinyl]-indol-1-yl}-acetic acid | phenyl | ethyl | C22H19N3O3 373.411 | 2.13 (LC-1) | 374.21 |
| 106 | {3-[(E)-2-(butyl-phenyl-carbamoyl)-2-cyano-vinyl]-indol-1-yl}-acetic acid | phenyl | butyl | C24H23N3O3 401.465 | 2.34 (LC-1) | 402.24 |

Formula, wherein R[hu 1 [l =[0 R[hu 2 [l [32 [0 R[hu 3 [l =[0 R[hu 4 [l =[0 11.

TABLE 2

Examples 107-109 with the general structure of

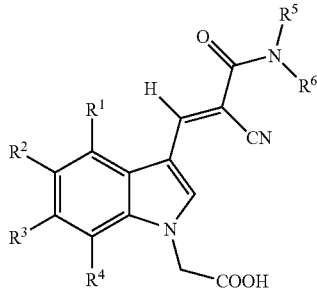

I

| Ex. | Name | R² | R⁵ | R⁶ | Formula Mol weight | $t_R$ [min] (Method) | MS Data m/z [M + H]⁺ |
|---|---|---|---|---|---|---|---|
| 107 | [5-bromo-3-((E)-2-cyano-2-phenylcarbamoyl-vinyl)-indol-1-yl]-acetic acid | bromo | H | phenyl | C20H14N3O3Br 424.253 | 2.25 (LC-2) | 448.04 [M + Na]⁺ |
| 108 | [3-((E)-2-cyano-2-phenylcarbamoyl-vinyl)-5-fluoro-indol-1-yl]-acetic acid | fluoro | H | phenyl | C20H14N3O3F 363.347 | 2.13 (LC-2) | 364.21 |
| 109 | [3-((E)-2-cyano-2-phenylcarbamoyl-vinyl)-5-methyl-indol-1-yl]-acetic acid | methyl | H | phenyl | C21H17N3O3 359.384 | 2.18 (LC-2) | 360.20 |

Formula I, wherein R¹ = R³ = R⁴ = H.

TABLE 3

Examples 110-111 with the general structure of

[Structure I: indole with R¹, R², R³, R⁴ substituents on benzene ring, 3-position bears (E)-CH=C(CN)-C(O)-N(R⁵)(R⁶), N-1 bears CH₂COOH]

I

| Ex. | Name | R³ | R⁵ | R⁶ | Formula Mol weight | $t_R$ [min] (Method) | MS Data m/z [M + H]⁺ |
|---|---|---|---|---|---|---|---|
| 110 | [3-((E)-2-cyano-2-phenylcarbamoyl-vinyl)-6-fluoro-indol-1-yl]-acetic acid | fluoro | H | phenyl | C20H14N3O3F 363.347 | 2.14 (LC-2) | 364.14 |
| 111 | [3-((E)-2-cyano-2-phenylcarbamoyl-vinyl)-6-nitro-indol-1-yl]-acetic acid | nitro | H | phenyl | C20H14N4O5 390.354 | 2.12 (LC-2) | 391.22 |

Formula I, wherein R¹ = R² = R⁴ = H.

TABLE 4

Example 112 with the general structure of

[Structure I: indole with R¹, R², R³, R⁴ substituents, 3-position bears (E)-CH=C(CN)-C(O)-N(R⁵)(R⁶), N-1 bears CH₂COOH]

I

| Ex. | Compound | R⁴ | R⁵ | R⁶ | Formula Mol weight | $t_R$ [min] (Method) | MS Data m/z [M + H]⁺ |
|---|---|---|---|---|---|---|---|
| 112 | [3-((E)-2-cyano-2-phenylcarbamoyl-vinyl)-7-methyl-indol-1-yl]-acetic acid | methyl | H | phenyl | C21H17N3O3 359.384 | 2.16 (LC-2) | 360.20 |

Formula I, wherein R¹ = R² = R³ = H.

TABLE 5

Examples 113-132 with the general structure of

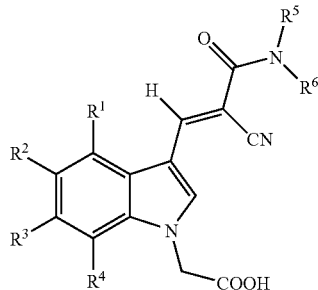

I

| Ex. | Name | R⁵ | R⁶ | Formula Mol weight | $t_R$ [min] (Meth.) | MS Data m/z [M + H]⁺ |
|---|---|---|---|---|---|---|
| 113 | {3-[(E)-3-(2-chloro-phenothiazin-10-yl)-2-cyano-3-oxo-propenyl]-indol-1-yl}-acetic acid | 2-chloro-phenothiazin-10-yl | | C26H16N3O3ClS 485.95 | 1.17 (LC-4) | 508.04 [M + Na]⁺ |
| 114 | {3-[(E)-2-cyano-2-(phenyl-thiophen-3-ylmethyl-carbamoyl)-vinyl]-indol-1-yl}-acetic acid | phenyl | thiophen-3-ylmethyl | C25H19N3O3S 441.51 | 1.10 (LC-4) | 442.81 |
| 115 | (3-{(E)-2-cyano-2-[(2,2-diphenyl-ethyl)-phenyl-carbamoyl]-vinyl}-indol-1-yl)-acetic acid | phenyl | (2,2-diphenyl-ethyl) | C34H27N3O3 525.606 | 1.18 (LC-4) | 526.06 |
| 116 | (3-{(E)-2-Cyano-2-[phenyl-(3-phenyl-propyl)-carbamoyl]-vinyl}-indol-1-yl)-acetic acid | phenyl | 3-phenyl-propyl | C29H25N3O3 463.536 | 1.14 (LC-4) | 464.07 |
| 117 | [3-((E)-2-cyano-2-{[2-(4-fluoro-phenyl)-ethyl]-phenyl-carbamoyl}-vinyl)-indol-1-yl]-acetic acid | phenyl | 4-fluoro-phenyl-ethyl | C28H22N3O3F 467.499 | 1.13 (LC-4) | 468.98 |
| 118 | {3-[(E)-2-cyano-3-(11H-10-oxa-5-aza-dibenzo[a,d]cyclohepten-5-yl)-3-oxo-propenyl]-indol-1-yl}-acetic acid | 11H-10-oxa-5-aza-dibenzo[a,d]cyclohepten-5-yl | | C27H19N3O4 449.465 | 1.10 (LC-4) | 450.98 |
| 119 | {3-[(E)-2-cyano-2-(isopropyl-phenyl-carbamoyl)-vinyl]-indol-1-yl}-acetic acid | isopropyl | phenyl | C23H21N3O3 387.438 | 1.10 (LC-3) | 387.86 |
| 120 | (3-{(E)-2-cyano-2-[(3,4-dichloro-phenyl)-methyl-carbamoyl]-vinyl}-indol-1-yl)-acetic acid | methyl | 3,4-dichloro-phenyl | C21H15N3O3Cl2 428.274 | 1.11 (LC-3) | 427.86 [M − H]⁻ |
| 121 | (3-{(E)-2-cyano-2-[ethyl-(4-trifluoromethoxy-phenyl)-carbamoyl]-vinyl}-indol-1-yl)-acetic acid | ethyl | 4-trifluoromethoxy-phenyl | C23H18N3O4F3 457.407 | 1.16 (LC-3) | 458.94 |
| 122 | {3-[(E)-2-(benzhydryl-carbamoyl)-2-cyano-vinyl]-indol-1-yl}-acetic acid | H | benzhydryl | C27H21N3O3 435.482 | 1.16 (LC-3) | 435.96 |
| 123 | (3-{(E)-2-cyano-2-[methyl-(2-trifluoromethoxy-phenyl)-carbamoyl]-vinyl}-indol-1-yl)-acetic acid | methyl | 2-trifluoromethoxy-phenyl | C22H16N3O4F3 443.38 | 1.10 (LC-3) | 443.85 |
| 124 | {3-[(E)-2-cyano-2-(2,4-difluoro-phenylcarbamoyl)-vinyl]-indol-1-yl}-acetic acid | H | 2,4-difluoro-phenyl | C20H13N3O3F2 381.337 | 1.07 (LC-3) | 382.94 |

TABLE 5-continued

Examples 113-132 with the general structure of

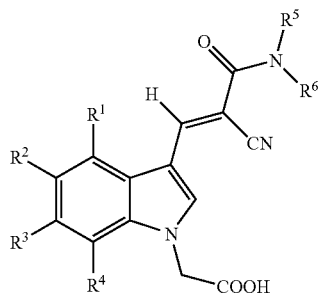

I

Formula I, wherein $R^1 = R^2 = R^3 = R^4 = H$.

| Ex. | Name | $R^5$ | $R^6$ | Formula Mol weight | $t_R$ [min] (Meth.) | MS Data m/z $[M + H]^+$ |
|---|---|---|---|---|---|---|
| 125 | (3-{(E)-2-cyano-2-[methyl-(4-trifluoromethoxy-phenyl)-carbamoyl]-vinyl}-indol-1-yl)-acetic acid | methyl | 4-trifluoromethoxy-phenyl | C22H16N3O4F3 443.38 | 1.11 (LC-3) | 444.96 |
| 126 | {3-[(E)-2-cyano-2-(ethyl-naphthalen-1-yl-carbamoyl)-vinyl]-indol-1-yl}-acetic acid | ethyl | naphthalen-1-yl | C26H21N3O3 423.471 | 1.14 (LC-3) | 423.84 |
| 127 | (3-{(E)-2-cyano-2-[(2,4-difluoro-phenyl)-methyl-carbamoyl]-vinyl}-indol-1-yl)-acetic acid | methyl | 2,4-difluoro-phenyl | C21H15N3O3F2 395.364 | 1.05 (LC-3) | 396.92 |
| 128 | {3-[(E)-2-cyano-2-(2,4,6-trifluoro-phenylcarbamoyl)-vinyl]-indol-1-yl}-acetic acid | H | 2,4,6-trifluoro-phenyl | C20H12N3O3F3 399.327 | 1.03 (LC-3) | 400.94 |
| 129 | {3-[(E)-2-cyano-2-(2,3,4-trifluoro-phenylcarbamoyl)-vinyl]-indol-1-yl}-acetic acid | H | 2,3,4-trifluoro-phenyl | C20H12N3O3F3 399.327 | 1.10 (LC-3) | 399.76 |
| 130 | {3-[(E)-2-cyano-3-(3,4-dihydro-1H-isoquinolin-2-yl)-3-oxo-propenyl]-indol-1-yl}-acetic acid | 3,4-dihydro-1H-isoquinolin-2-yl | | C23H19N3O3 385.422 | 1.07 (LC-3) | 386.96 |
| 131 | {3-[(E)-2-cyano-3-oxo-3-(7-trifluoromethyl-3,4-dihydro-2H-quinolin-1-yl)-propenyl]-indol-1-yl}-acetic acid | 7-trifluoromethyl-3,4-dihydro-2H-quinolin-1-yl | | C24H18N3O3F3 453.419 | 1.13 (LC-3) | 454.92 |
| 132 | (3-{(B)-2-cyano-2-[(3-fluoro-phenyl)-methyl-carbamoyl]-vinyl}-indol-1-yl)-acetic acid | methyl | 3-fluoro-phenyl | C21H16N3O3F 377.89 | 1.03 (LC-3) | 377.89 |

TABLE 6

Examples 133-147 with the general structure of

I

| Ex. | Compound | R² | R⁵ | R⁶ | Formula Mol weight | t_R [min] (Method) | MS Data m/z [M + H]⁺ |
|---|---|---|---|---|---|---|---|
| 133 | [3-((E)-2-cyano-3-dibenzo[b,f]azepin-5-yl-3-oxo-propenyl)-5-fluoro-indol-1-yl]-acetic acid | fluoro | dibenzo[b,f]azepin-5-yl | | C28H18N3O3F 463.467 | 1.00 (LC-5) | 464.29 |
| 134 | {3-[(E)-2-cyano-3-(6,11-dihydro-dibenzo[b,e]azepin-5-yl)-3-oxo-propenyl]-5-fluoro-indol-1-yl}-acetic acid | fluoro | 6,11-dihydro-dibenzo[b,e]azepin-5-yl | | C28H20N3O3F 465.483 | 1.02 (LC-5) | 466.3 |
| 135 | {3-[(E)-2-(benzyl-phenyl-carbamoyl)-2-cyano-vinyl]-5-fluoro-indol-1-yl}-acetic acid | fluoro | benzyl | phenyl | C27H20N3O3F 453.472 | 1.00 (LC-5) | 454.28 |
| 136 | {3-[(E)-2-cyano-2-(cyclohexyl-phenyl-carbamoyl)-vinyl]-5-fluoro-indol-1-yl}-acetic acid | fluoro | cyclohexyl | phenyl | C26H24N3O3F 493 | 1.03 (LC-5) | 446.31 |
| 137 | {3-[(E)-2-(butyl-phenyl-carbamoyl)-2-cyano-vinyl]-5-fluoro-indol-1-yl}-acetic acid | fluoro | butyl | phenyl | C24H22N3O3F 419.455 | 1.01 (LC-5) | 420.29 |
| 138 | (3-{(E)-2-cyano-2-[(4-fluoro-phenyl)-methyl-carbamoyl]-vinyl}-5-fluoro-indol-1-yl)-acetic acid | fluoro- | methyl | 4-fluoro-phenyl | C21H15N3O3F2 395.364 | 1.04 (LC-3) | 396.02 |
| 139 | (3-{(E)-2-cyano-2-[(3-fluoro-phenyl)-methyl-carbamoyl]-vinyl}-5-fluoro-indol-1-yl)-acetic acid | fluoro | methyl | 3-fluoro-phenyl | C21H15N3O3F2 395.364 | 1.04 (LC-3) | 396.02 |
| 140 | (3-{(E)-2-cyano-2-[(3,4-dichloro-phenyl)-methyl-carbamoyl]-vinyl}-5-fluoro-indol-1-yl)-acetic acid | fluoro | methyl | 3,4-dichloro-phenyl | C21H14N3O3Cl2F 446.264 | 1.15 (LC-3) | 447.86 |
| 141 | (3-{(E)-2-cyano-2-[methyl-(2-trifluoromethyl-phenyl)-carbamoyl]-vinyl}-5-fluoro-indol-1-yl)-acetic acid | fluoro | methyl | 2-trifluoromethyl-phenyl | C22H15N3O3F4 445.371 | 0.97 (LC-5) | 446.2 |

TABLE 6-continued

Examples 133-147 with the general structure of

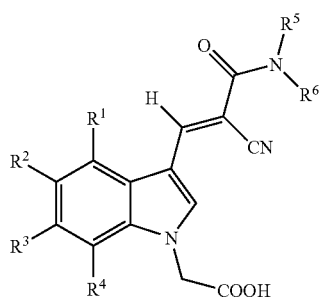

I

Formula I, wherein $R^1 = R^3 = R^4 = H$.

| Ex. | Compound | $R^2$ | $R^5$ | $R^6$ | Formula Mol weight | $t_R$ [min] (Method) | MS Data m/z $[M + H]^+$ |
|---|---|---|---|---|---|---|---|
| 142 | (3-{(E)-2-cyano-2-[(2,4-difluoro-phenyl)-methyl-carbamoyl]-vinyl}-5-fluoro-indol-1-yl)-acetic acid | fluoro | methyl | 2,4-difluoro-phenyl | C21H14N3O3F3 413.354 | 0.95 (LC-5) | 414.2 |
| 143 | {3-[(E)-2-cyano-2-(phenyl-thiophen-3-ylmethyl-carbamoyl)-vinyl]-5-fluoro-indol-1-yl}-acetic acid | fluoro | phenyl | thiophen-3-ylmethyl | C25H18N3O3FS 459.5 | 1.15 (LC-3) | 460.05 |
| 144 | {3-[(E)-2-cyano-3-oxo-3-(7-trifluoromethyl-4-dihydro-2H-quinolin-1-yl) propenyl]-5-fluoro-indol-1-yl}-acetic acid | fluoro | 7-trifluoromethyl-3,4-dihydro-2H-quinolin-1-yl | | C24H17N3O3F4 471.409 | 1.15 (LC-3) | 472.99 |
| 145 | (3-{(E)-2-cyano-2-[ethyl-(4-trifluoromethoxy-phenyl)-carbamoyl]-vinyl}-5-fluoro-indol-1-yl)-acetic acid | fluoro | ethyl | 4-trifluoromethoxy-phenyl | C23H17N3O4F4 475.397 | 1.20 (LC-3) | 475.97 |
| 146 | {3-[(E)-2-cyano-3-(3,4-dihydro-1H-isoquinolin-2-yl)-3-oxo-propenyl]-5-fluoro-indol-1-yl}-acetic acid | fluoro | 3,4-dihydro-1H-isoquinolin-2-yl | | C23H18N3O3F 403.412 | 1.09 (LC-3) | 403.98 |
| 147 | {3-[(E)-2-cyano-2-(phenethyl-phenyl-carbamoyl)-vinyl]-5-fluoro-indol-1-yl}-acetic acid | fluoro | phenyl | phenethyl | C28H22N3O3F 467.499 | 1.22 (LC-3) | 468.08 |

TABLE 7

Examples 148-154 with the general structure of

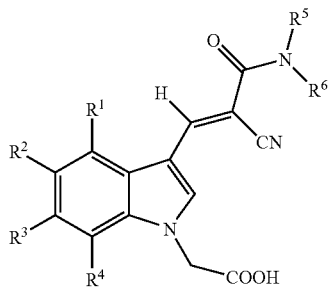

Formula I, wherein $R^1 = R^2 = R^4 = H$.

| Ex. | Compound | $R^3$ | $R^5$ | $R^6$ | Formula Mol weight | $t_R$ [min] (Method) | MS Data m/z $[M + H]^+$ |
|---|---|---|---|---|---|---|---|
| 148 | [3-((E)-2-cyano-3-dibenzo[b,f]azepin-5-yl-3-oxo-propenyl)-6-methyl-indol-1-yl]-acetic acid | methyl | dibenzo[b,f]azepin-5-yl | | C29H21N3O3 459.504 | 1.01 (LC-5) | 460.31 |
| 149 | {3-[(E)-2-cyano-3-(6,11-dihydro-dibenzo[b,e]azepin-5-yl)-3-oxo-propenyl]-6-methyl-indol-1-yl}-acetic acid | methyl | 6,11-dihydro-dibenzo[b,e]azepin-5-yl | | C29H23N3O3 461.52 | 1.03 (LC-5) | 462.32 |
| 150 | {3-[(E)-2-cyano-3-(10,11-dihydro-dibenzo[b,f]azepin-5-yl)-3-oxo-propenyl]-6-methyl-indol-1-yl}-acetic acid | methyl | 10,11-dihydro-dibenzo[b,f]azepin-5-yl | | C29H23N3O3 461.52 | 1.02 (LC-5) | 462.32 |
| 151 | {3-[(E)-2-(benzyl-phenyl-carbamoyl)-2-cyano-vinyl]-6-methyl-indol-1-yl}-acetic acid | methyl | phenyl | benzyl | C28H23N3O3 449.509 | 1.02 (LC-5) | 450.31 |
| 152 | {3-[(E)-2-cyano-2-(cyclohexyl-phenyl-carbamoyl)-vinyl[-6-methyl-indol-1-yl}-acetic acid | methyl | phenyl | cyclohexyl | C27H27N3O3 441.529 | 1.05 (LC-5) | 442.32 |
| 153 | (3-{(E)-2-cyano-2-[(4-fluoro-phenyl)-methyl-carbamoyl]-vinyl}-6-methyl-indol-1-yl)-acetic acid | methyl | methyl | 4-fluoro-phenyl | C22H18N3O3F 391.401 | 0.95 (LC-5) | 392.26 |
| 154 | {3-[(E)-2-(butyl-phenyl-carbamoyl)-2-cyano-vinyl]-6-methyl-indol-1-yl}-acetic acid | methyl | butyl | phenyl | C25H25N3O3 415.492 | 1.02 (LC-5) | 416.33 |

TABLE 8

Examples 155-156 with the general structure of

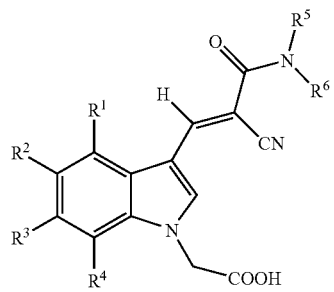

Formula I, wherein $R^1 = R^2 = R^3 = H$.

| Ex. | Compound | $R^4$ | $R^5$ | $R^6$ | Formula Mol weight | $t_R$ [min] (Method) | MS Data m/z $[M + H]^+$ |
|---|---|---|---|---|---|---|---|
| 155 | {3-[(E)-2-cyano-2-(cyclohexyl-phenyl-carbamoyl)-vinyl]-7-methyl-indol-1-yl}-acetic acid | methyl | phenyl | cyclohexyl | C27H27N3O3 441.529 | 1.04 (LC-5) | 442.33 |
| 156 | (3-{(E)-2-cyano-2-[(4-fluoro-phenyl)-methyl-carbamoyl]-vinyl}-7-methyl-indol-1-yl)-acetic acid | methyl | methyl | 4-fluoro-phenyl | C22H18N3O3F 391.401 | 0.98 (LC-5) | 334.26 |

Biological Assays

Example B-1

Preparation of CRTH2 Membranes an Radioligand Binding Assay

Preparation of the membranes and radioligand binding assays are performed according to known procedures, e.g. Sawyer N. et al. (*Br. J. Pharmacol.*, 2002, 137, 1163-1172). A clonal HEK 293 cell line, expressing high level of recombinant hCRTH2 receptor, is selected for the preparation of membranes. Cells are detached from culture plates in 5 ml buffer A per plate (5 mM Tris, 1 mM MgCl$_2$x6H$_2$O, 0.1 mM PMSF, 0.1 mM phenanthroline) using a police rubber and transferred into centrifugation tubes and frozen at −80° C. After thawing, the cells are centrifuged at 500 g for 5 min and then resuspended in buffer A. Cells are then fragmented by homogenization with a Polytron homogenizer for 30 s. The membrane fragments are centrifuged at 3000 g for 40 min and resuspended in membranes in buffer B (50 mM Tris, 25 mM MgCl$_2$, 250 mM saccharose, pH 7.4) and aliquots are stored frozen.

Binding assay is performed in a total volume of 250 µl. In each well, 75 µl buffer C (50 mM Tris, 100 mM NaCl, 1 mM EDTA, 0.1% BSA (protease free), 0.01% NaN$_3$, pH 7.4) was mixed with 50 µl {$^3$H}-PGD$_2$ (at 2.5 nM (220.000 dpm per well) from Amersham, TRK734), 100 µl CRTH2 membranes to give 80 µg per well and 25 µl of test compound in buffer C containing 1% DMSO. For unspecific binding, PGD2 is added to the reaction mixture at 1 µM final concentration. This binding assay mix is incubated at rt for 90 min and then filtered through a GF/C filter plate. The filter is washed three times with ice cold binding buffer. Then, 40 µl per well Microscint-40 (Packard) are added and the bound radioactivity is quantified by means of Topcount (Packard).

Example B-2

Intracellular Calcium Mobilization Assay (FLIPR)

Cells (HEK-293), stably expressing the hCRTH$_2$ receptor under the control of the cytomegalovirus promotor from a single insertion of the expression vector pcDNA5 (Invitrogen), are grown to confluency in DMEM (low glucose, Gibco) medium supplemented with 10% fetal calf serum (both Bioconcept, Switzerland) under standard mammalian cell culture conditions (37° C. in a humidified atmosphere of 5% CO$_2$). Cells are detached from culture dishes using a dissociation buffer (0.02% EDTA in PBS, Gibco) for 1 min, and collected by centrifugation at 200 g at rt for 5 min in assay buffer (equal parts of Hank's BSS (HBSS, Bioconcept) and DMEM (low glucose, without phenol red, Gibco)). After incubation for 45 min (37° C. and 5% CO$_2$) in the presence of 1 µM Fluo-4 and 0.04% Pluronic F-127 (both Molecular Probes), 20 mM HEPES (Gibco) in assay buffer, the cells are washed with and resuspended in assay buffer, then seeded onto 384-well FLIPR assay plates (Greiner) at 50,000 cells in 66 µl per well), and sedimented by centrifugation.

Stock solutions of test compounds are made up at a concentration of 10 mM in DMSO, and serially diluted in assay buffer to concentrations required for inhibition dose response curves. Prostaglandin D$_2$ (Biomol, Plymouth Meeting, Pa.) is used as an agonist.

A FLIPR384 instrument (Molecular Devices) is operated according to the manufacturer's standard instructions, adding 4 µl of test compound dissolved at 10 mM in DMSO and diluted prior to the experiment in assay buffer to obtain the desired final concentration. 10 µl of 80 nM prostaglandin $D_2$ (Biomol, Plymouth Meeting, Pa.) in assay buffer, supplemented with 0.8% bovine serum albumin (fatty acid content<0.02%, Sigma), is then added to obtain a final concentration of 10 nM and 0.1%, respectively. Changes in fluorescence are monitored before and after the addition of test compounds at $\lambda_{ex}$=488 nm and $\lambda_{em}$=540 nm. Emission peak values above base level after prostaglandin $D_2$ addition are exported after base line subtraction. Values are normalized to high-level control (no test compound added) after subtraction of base line value (no prostaglandin $D_2$ added). The program XLlfit 3.0 (IDBS) is used to fit the data to a single site dose response curve of the equation (A+((B−A)/(1+((C/x)^D)))) and to calculate the $IC_{50}$ values.

BIOLOGICAL RESULTS

The following results have been obtained using the procedures given above (biological tests B1 and B2) for the above mentioned example compounds:

| Example No. | CRTH2 binding $IC_{50}$ (nM) (method B1 above) | CRTH2 FLIPR $IC_{50}$ (nM) (method B2 above) |
|---|---|---|
| 12 | 29 | 90 |
| 29 | 42 | 151 |
| 45 | 7 | 48 |
| 46 | 11 | 61 |
| 47 | 9 | 54 |
| 49 | 35 | 146 |
| 54 | 18 | 98 |
| 64 | 40 | 61 |
| 70 | 76 | 58 |
| 87 | 12 | 57 |
| 89 | 6 | 114 |
| 94 | 10 | 181 |
| 99 | 16 | 159 |
| 101 | 15 | 182 |
| 113 | 9 | 66 |
| 141 | 17 | 47 |
| 149 | 49 | 253 |

The invention claimed is:
1. A compound of formula $I_{C1}$

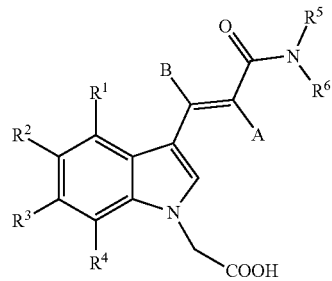

wherein
A represents cyano;
B represents hydrogen;
$R^1$, $R^2$, $R^3$ and $R^4$ independently represent hydrogen, alkyl, halogen, nitro, cyano or formyl; and
$R^5$ and $R^6$ independently represent hydrogen, alkyl, cycloalkyl, cycloalkyl-alkyl, heteroaryl, heteroaryl-alkyl, alkenyl, carboxyalkyl, cyanoalkyl, diphenylalkyl, aryl, aryl-alkoxy-aryl, aryl-alkyl, aryl-alkyl-aryl, aryl-carbonyl-aryl or aryloxy-aryl, or $R^5$ and $R^6$, together with the nitrogen atom to which they are attached, form a heterocyclic ring system;
or a salt of the compound of formula $I_{C1}$;
with the proviso that the compound is not:
{3-[(E)-2-cyano-2-(4-fluoro-phenylcarbamoyl)-vinyl]-indol-1-yl}-acetic acid;
[3-((E)-2-cyano-2-m-tolylcarbamoyl-vinyl)-indol-1-yl]-acetic acid;
{3-[(E)-2-(3-bromo-phenylcarbamoyl)-2-cyano-vinyl]-indol-1-yl}-acetic acid;
[3-((E)-2-cyano-2-phenylcarbamoyl-vinyl)-indol-1-yl]-acetic acid;
[3-((E)-2-benzylcarbamoyl-2-cyano-vinyl)-indol-1-yl]-acetic acid;
[3-((E)-2-cyano-2-o-tolylcarbamoyl-vinyl)-indol-1-yl]-acetic acid;
[3-((E)-2-cyano-2-p-tolylcarbamoyl-vinyl)-indol-1-yl]-acetic acid;
{3-[(E)-2-(4-bromo-phenylcarbamoyl)-2-cyano-vinyl]-indol-1-yl}-acetic acid;
{3-[(E)-2-cyano-2-(4-ethyl-phenylcarbamoyl)-vinyl]-indol-1-yl}-acetic acid;
{3-[(E)-2-cyano-2-(4-methoxy-phenylcarbamoyl)-vinyl]-indol-1-yl}-acetic acid;
{3-[(E)-2-cyano-2-(4-ethoxy-phenylcarbamoyl)-vinyl]-indol-1-yl}-acetic acid;
[3-((E)-2-cyano-2-isopropylcarbamoyl-vinyl)-indol-1-yl]-acetic acid;
{3-[(E)-2-cyano-2-(3-ethoxy-phenylcarbamoyl)-vinyl]-indol-1-yl}-acetic acid;
{3-[(E)-2-cyano-3-[[2-(1H-indol-3-yl)ethyl]amino]-3-oxo-1-propenyl]-indol-1-yl}-acetic acid;
{3-[(E)-2-cyano-2-(4-chloro-phenylcarbamoyl)-vinyl]-indol-1-yl}-acetic acid;
{3-[(E)-2-cyano-3-(4-methyl-piperidin-1-yl)-3-oxo-propenyl]-indol-1-yl}-acetic acid;
{3-[(E)-2-(3-chloro-4-methyl-phenylcarbamoyl)-2-cyano-vinyl]-indol-1-yl}-acetic acid;
{3-[(E)-2-cyano-2-(3-phenyl-propylcarbamoyl)-vinyl]-indol-1-yl}-acetic acid;
{3-[(E)-2-cyano-2-(2,3-dichloro-phenylcarbamoyl)-vinyl]-indol-1-yl}-acetic acid;
{3-[(E)-2-(5-chloro-2-methyl-phenylcarbamoyl)-2-cyano-vinyl]-indol-1-yl}-acetic acid;
{3-[(E)-2-cyano-2-(4-methoxy-benzylcarbamoyl)-vinyl]-indol-1-yl}-acetic acid;
{3-[(E)-2-cyano-2-(2-fluoro-phenylcarbamoyl)-vinyl]-indol-1-yl}-acetic acid; or
{3-[(E)-2-cyano-3-oxo-3-(4-phenyl-piperazin-1-yl)-propenyl]-indol-1-yl}-acetic acid.

2. The compound according to claim 1, wherein the groups $R^5$ and $R^6$ do not form a heterocyclic ring system together with the nitrogen atom to which they are attached; or a salt of the compound.

3. The compound according to claim 2, wherein $R^5$ is aryl and $R^6$ is alkyl, cycloalkyl, alkenyl, cyanoalkyl, diphenylalkyl, heteroaryl-alkyl, aryl-alkyl or aryl; or a salt of the compound.

4. The compound according to claim 2, wherein $R^5$ is aryl-alkyl and $R^6$ is alkyl, aryl or aryl-alkyl; or a salt of the compound.

5. The compound according to claim 1, wherein the groups $R^5$ and $R^6$ form a heterocyclic ring system together with the nitrogen atom to which they are attached; or a salt of the compound.

6. The compound according to claim 1, wherein the compound is:

{3-[(E)-2-cyano-2-(cyclohexylmethyl-carbamoyl)-vinyl]-indol-1-yl}-acetic acid;
[3-((E)-2-cyano-2-phenethylcarbamoyl-vinyl)-indol-1-yl]-acetic acid;
[3-((E)-2-cyano-2-propylcarbamoyl-vinyl)-indol-1-yl]-acetic acid;
[3-((E)-2-cyano-2-cyclohexylcarbamoyl-vinyl)-indol-1-yl]-acetic acid;
{3-[(E)-2-cyano-2-(3-methyl-butylcarbamoyl)-vinyl]-indol-1-yl}-acetic acid;
{3-[(E)-2-(benzyl-phenyl-carbamoyl)-2-cyano-vinyl]-indol-1-yl}-acetic acid;
{3-[(E)-2-cyano-2-(4-cyano-phenylcarbamoyl)-vinyl]-indol-1-yl}-acetic acid;
{3-[(E)-2-cyano-2-(4-phenoxy-phenylcarbamoyl)-vinyl]-indol-1-yl}-acetic acid;
{3-[(E)-2-cyano-2-(naphthalen-2-ylcarbamoyl)-vinyl]-indol-1-yl}-acetic acid;
{3-[(E)-2-cyano-2-(2-isopropyl-phenylcarbamoyl)-vinyl]-indol-1-yl}-acetic acid;
{3-[(E)-2-cyano-2-(4-isopropyl-phenylcarbamoyl)-vinyl]-indol-1-yl}-acetic acid;
{3-[(E)-2-cyano-2-(3-methoxy-phenylcarbamoyl)-vinyl]-indol-1-yl}-acetic acid;
{3-[(E)-2-cyano-2-(3-fluoro-phenylcarbamoyl)-vinyl]-indol-1-yl}-acetic acid;
{3-[(E)-2-cyano-2-(9H-fluoren-2-ylcarbamoyl)-vinyl]-indol-1-yl}-acetic acid;
{3-[(E)-2-cyano-2-(4-propyl-phenylcarbamoyl)-vinyl]-indol-1-yl}-acetic acid;
{3-[(E)-2-(biphenyl-4-ylcarbamoyl)-2-cyano-vinyl]indol-1-yl}-acetic acid;
{3-[(E)-2-cyano-2-(3,2'-dimethyl-biphenyl-4-ylcarbamoyl)-vinyl]-indol-1-yl}-acetic acid;
{3-[(E)-2-(4-tert-butyl-phenylcarbamoyl)-2-cyano-vinyl]-indol-1-yl}-acetic acid;
{3-[(E)-2-(2-benzyl-phenylcarbamoyl)-2-cyano-vinyl]indol-1-yl}-acetic acid;
{3-[(E)-2-cyano-2-(4-butyl-phenylcarbamoyl)-vinyl]-indol-1-yl}-acetic acid;
{3-[(E)-2-(2-acetyl-phenylcarbamoyl)-2-cyano-vinyl]-indol-1-yl}-acetic acid;
{3-[(E)-2-cyano-2-(indan-5-ylcarbamoyl)-vinyl]-indol-1-yl}-acetic acid;
{3-[(E)-2-(4-Sec-butyl-phenylcarbamoyl)-2-cyano-vinyl]-indol-1-yl}-acetic acid;
{3-[(E)-2-cyano-2-(2-propyl-phenylcarbamoyl)-vinyl]-indol-1-yl}-acetic acid;
{3-[(E)-2-cyano-2-(3-phenoxy-phenylcarbamoyl)-vinyl]-indol-1-yl}-acetic acid;
{3-[(E)-2-cyano-2-(3-ethyl-phenylcarbamoyl)-vinyl]-indol-1-yl}-acetic acid;
{3-[(E)-2-cyano-2-(2-ethoxy-phenylcarbamoyl)-vinyl]-indol-1-yl}-acetic acid;
{3-[(E)-2-(3-benzyloxy-phenylcarbamoyl)-2-cyano-vinyl]-indol-1-yl}-acetic acid;
{3-[(E)-2-cyano-2-(4-iodo-phenylcarbamoyl)-vinyl]-indol-1-yl}-acetic acid;
{3-[(E)-2-cyano-2-(3-iodo-phenylcarbamoyl)-vinyl]-indol-1-yl}-acetic acid;
(3-{(E)-2-cyano-2-[(4-fluoro-phenyl)-methyl-carbamoyl]-vinyl}-indol-1-yl)-acetic acid;
(3-{(E)-2-cyano-2-[(4-methoxy-phenyl)-methyl-carbamoyl]-vinyl}-indol-1-yl)-acetic acid;
{3-[(E)-2-cyano-2-(methyl-phenyl-carbamoyl)-vinyl]-indol-1-yl}-acetic acid;
{3-[(E)-2-cyano-3-(3,4-dihydro-2H-quinolin-1-yl)-3-oxo-propenyl]-indol-1-yl}-acetic acid;
{3-[(E)-2-cyano-2-(methyl-p-tolyl-carbamoyl)-vinyl]-indol-1-yl}-acetic acid;
(3-{(E)-2-cyano-2-[2-(2,4-dichloro-phenoxy)-phenylcarbamoyl]-vinyl}-indol-1-yl)-acetic acid;
{3-[(E)-2-cyano-2-(2,5-dimethyl-phenylcarbamoyl)-vinyl]-indol-1-yl}-acetic acid;
{3-[(E)-2-cyano-2-(9-ethyl-9H-carbazol-3-ylcarbamoyl)-vinyl]-indol-1-yl}-acetic acid;
{3-[(E)-2-(3,5-bis-trifluoromethyl-phenylcarbamoyl)-2-cyano-vinyl]-indol-1-yl}-acetic acid;
{3-[(E)-2-cyano-2-(5-methoxy-2-methyl-phenylcarbamoyl)-vinyl]-indol-1-yl}-acetic acid;
{3-[(E)-2-(3-benzoyl-phenylcarbamoyl)-2-cyano-vinyl]-indol-1-yl}-acetic acid;
{3-[(E)-2-(4-benzyloxy-phenylcarbamoyl)-2-cyano-vinyl]-indol-1-yl}-acetic acid;
{3-[(E)-2-cyano-2-(3-nitro-phenylcarbamoyl)-vinyl]-indol-1-yl}-acetic acid;
{3-[(E)-2-cyano-2-(9-oxo-9H-fluoren-2-ylcarbamoyl)-vinyl]indol-1-yl}-acetic acid;
{3-[(E)-2-cyano-2-(4-methoxy-biphenyl-3-ylcarbamoyl)-vinyl]-indol-1-yl}-acetic acid;
{3-[(E)-2-cyano-2-(2-methoxy-dibenzofuran-3-ylcarbamoyl)-vinyl]indol-1-yl}-acetic acid;
{3-[(E)-2-cyano-2-(9-oxo-9H-fluoren-4-ylcarbamoyl)-vinyl]-indol-1-yl}-acetic acid;
{3-[(E)-2-cyano-2-(9-oxo-9H-fluoren-1-ylcarbamoyl)-vinyl]-indol-1-yl}-acetic acid;
{3-[(E)-2-(2-benzoyl-phenylcarbamoyl)-2-cyano-vinyl]-indol-1-yl}-acetic acid;
{3-[(E)-2-(3-chloro-4-methoxy-phenylcarbamoyl)-2-cyano-vinyl]-indol-1-yl}-acetic acid;
{3-[(E)-2-(5-chloro-2-methoxy-phenylcarbamoyl)-2-cyano-vinyl]-indol-1-yl}-acetic acid;
3-[(E)-3-(1-carboxymethyl-1H-indol-3-yl)-2-cyano-acryloylamino]-4-methyl-benzoic acid methyl ester;
2-[(E)-3-(1-carboxymethyl-1H-indol-3-yl)-2-cyano-acryloylamino]-benzoic acid methyl ester;
{3-[(E)-2-cyano-2-(4-trifluoromethoxy-phenylcarbamoyl)-vinyl]-indol-1-yl}-acetic acid;
{3-[(E)-2-cyano-2-(3,5-dimethyl-phenylcarbamoyl)-vinyl]-indol-1-yl}-acetic acid;
{3-[(E)-2-(3-bromo-4-methyl-phenylcarbamoyl)-2-cyano-vinyl]-indol-1-yl}-acetic acid;
{3-[(E)-2-(4-bromo-3-methyl-phenylcarbamoyl)-2-cyano-vinyl]-indol-1-yl}-acetic acid;
4-[(E)-3-(1-carboxymethyl-1H-indol-3-yl)-2-cyano-acryloylamino]-benzoic acid ethyl ester;
3-[(E)-3-(1-carboxymethyl-1H-indol-3-yl)-2-cyano-acryloylamino]-benzoic acid methyl ester;
{3-[(E)-2-cyano-2-(4-trifluoromethyl-phenylcarbamoyl)-vinyl]-indol-1-yl}-acetic acid;
{3-[(E)-2-cyano-2-(3,5-dimethoxy-phenylcarbamoyl)-vinyl]-indol-1-yl}-acetic acid;
{3-[(E)-2-(4-bromo-3-chloro-phenylcarbamoyl)-2-cyano-vinyl]-indol-1-yl}-acetic acid;
{3-[(E)-2-(4-bromo-2-methyl-phenylcarbamoyl)-2-cyano-vinyl]-indol-1-yl}-acetic acid;
{3-[(E)-2-(4-acetyl-phenylcarbamoyl)-2-cyano-vinyl]-indol-1-yl}-acetic acid;
{3-[(E)-2-(2-bromo-4-methyl-phenylcarbamoyl)-2-cyano-vinyl]-indol-1-yl}-acetic acid;

{3-[(E)-2-(benzo[1,3]dioxol-5-ylcarbamoyl)-2-cyano-vinyl]-indol-1-yl}-acetic acid;
{3-[(E)-2-cyano-2-(phenethyl-phenyl-carbamoyl)-vinyl]-indol-1-yl}-acetic acid;
{3-[(E)-2-cyano-3-(11,12-dihydro-6H-dibenzo[b,f]azocin-5-yl)-3-oxo-propenyl]-indol-1-yl}-acetic acid;
[3-((E)-2-cyano-2-diphenylcarbamoyl-vinyl)-indol-1-yl]-acetic acid;
[3-((E)-2-cyano-3-dibenzo[b,f]azepin-5-yl-3-oxo-propenyl)-indol-1-yl]-acetic acid;
(3-{(E)-2-[(4-chloro-phenyl)-methyl-carbamoyl]-2-cyano-vinyl}-indol-1-yl)-acetic acid;
{3-[(E)-2-cyano-3-(6,11-dihydro-dibenzo[b,e]azepin-5-yl)-3-oxo-propenyl]-indol-1-yl}-acetic acid;
[3-((E)-2-cyano-2-diphenethylcarbamoyl-vinyl)-indol-1-yl]-acetic acid;
{3-[(E)-2-cyano-3-(10,11-dihydro-dibenzo[b,f]azepin-5-yl)-3-oxo-propenyl]-indol-1-yl}-acetic acid;
(3-{(E)-2-cyano-2-[methyl-((R)-1-phenyl-ethyl)-carbamoyl]-vinyl}-indol-1-yl)-acetic acid;
{3-[(E)-2-(benzyl-methyl-carbamoyl)-2-cyano-vinyl]-indol-1-yl}-acetic acid;
(3-{(E)-2-[(4-acetyl-phenyl)-methyl-carbamoyl]-2-cyano-vinyl}-indol-1-yl)-acetic acid;
(3-{(E)-2-[(4-acetyl-phenyl)-furan-2-ylmethyl-carbamoyl]-2-cyano-vinyl}-indol-1-yl)-acetic acid;
{3-[(E)-2-(benzyl-carboxymethyl-carbamoyl)-2-cyano-vinyl]-indol-1-yl}-acetic acid;
3-{benzyl-[(E)-3-(1-carboxymethyl-1H-indol-3-yl)-2-cyano-acryloyl]-amino}-propionic acid;
{3-[(E)-2-cyano-3-(2,3-dihydro-indol-1-yl)-3-oxo-propenyl]-indol-1-yl}-acetic acid;
{3-[(E)-2-(carboxymethyl-phenyl-carbamoyl)-2-cyano-vinyl]-indol-1-yl}-acetic acid;
(3-{(E)-2-cyano-2-[(2-cyano-ethyl)-phenyl-carbamoyl]-vinyl}-indol-1-yl)-acetic acid;
(3-{(E)-2-[(3-chloro-phenyl)-methyl-carbamoyl]-2-cyano-vinyl}-indol-1-yl)-acetic acid;
{3-[(E)-2-(allyl-phenyl-carbamoyl)-2-cyano-vinyl]-indol-1-yl}-acetic acid;
{3-[(E)-2-cyano-2-(cyclohexyl-phenyl-carbamoyl)-vinyl]-indol-1-yl}-acetic acid;
{3-[(E)-2-cyano-2-(methyl-o-tolyl-carbamoyl)-vinyl]-indol-1-yl}-acetic acid;
{3-[(E)-2-cyano-2-(ethyl-phenyl-carbamoyl)-vinyl]-indol-1-yl}-acetic acid;
{3-[(E)-2-(butyl-phenyl-carbamoyl)-2-cyano-vinyl]-indol-1-yl}-acetic acid;
[5-bromo-3-((E)-2-(cyano-2-phenylcarbamoyl-vinyl)-indol-1-yl]-acetic acid;
[3-((E)-2-cyano-2-phenylcarbamoyl-vinyl)-5-fluoro-indol-1-yl]-acetic acid;
[3-((E)-2-cyano-2-phenylcarbamoyl-vinyl)-5-methyl-indol-1-yl]-acetic acid;
[3-((E)-2-cyano-2-phenylcarbamoyl-vinyl)-6-fluoro-indol-1-yl]-acetic acid;
[3-((E)-2-cyano-2-phenylcarbamoyl-vinyl)-6-nitro-indol-1-yl]-acetic acid;
[3-((E)-2-cyano-2-phenylcarbamoyl-vinyl)-7-methyl-indol-1-yl]-acetic acid;
{3-[(E)-3-(2-chloro-phenothiazin-10-yl)-2-cyano-3-oxo-propenyl]-indol-1-yl}-acetic acid;
{3-[(E)-2-cyano-2-(phenyl-thiophen-3-ylmethyl-carbamoyl)-vinyl]-indol-1-yl}-acetic acid;
(3-{(E)-2-cyano-2-[(2,2-diphenyl-ethyl)-phenyl-carbamoyl]-vinyl}-indol-1-yl)-acetic acid;
(3-{(E)-2-cyano-2-[phenyl-(3-phenyl-propyl)-carbamoyl]-vinyl}-indol-1-yl)-acetic acid;
[3-((E)-2-cyano-2-{[2-(4-fluoro-phenyl)-ethyl]-phenyl-carbamoyl}-vinyl)-indol-1-yl]-acetic acid;
{3-[(E)-2-cyano-3-(11H-10-oxa-5-aza-dibenzo[a,d]cyclohepten-5-yl)-3-oxo-propenyl]-indol-1-yl}-acetic acid;
{3-[(E)-2-cyano-2-(isopropyl-phenyl-carbamoyl)-vinyl]-indol-1-yl}-acetic acid;
(3-{(E)-2-cyano-2-[(3,4-dichloro-phenyl)-methyl-carbamoyl]-vinyl}-indol-1-yl)-acetic acid;
(3-{(E)-2-cyano-2-[ethyl-(4-trifluoromethoxy-phenyl)-carbamoyl]-vinyl}-indol-1-yl)-acetic acid;
{3-[(E)-2-(benzhydryl-carbamoyl)-2-cyano-vinyl]-indol-1-yl}-acetic acid;
(3-{(E)-2-cyano-2-[methyl-(2-trifluoromethoxy-phenyl)-carbamoyl]-vinyl}-indol-1-yl)-acetic acid;
{3-[(E)-2-cyano-2-(2,4-difluoro-phenylcarbamoyl)-vinyl]-indol-1-yl}-acetic acid;
(3-{(E)-2-cyano-2-[methyl-(4-trifluoromethoxy-phenyl)-carbamoyl]-vinyl}-indol-1-yl)-acetic acid;
{3-[(E)-2-cyano-2-(ethyl-naphthalen-1-yl-carbamoyl)-vinyl]-indol-1-yl}-acetic acid;
(3-{(E)-2-cyano-2-[(2,4-difluoro-phenyl)-methyl-carbamoyl]-vinyl}-indol-1-yl)-acetic acid;
{3-[(E)-2-cyano-2-(2,4,6-trifluoro-phenylcarbamoyl)-vinyl]-indol-1-yl}-acetic acid;
{3-[(E)-2-cyano-2-(2,3,4-trifluoro-phenylcarbamoyl)-vinyl]-indol-1-yl}-acetic acid;
{3-[(E)-2-cyano-3-(3,4-dihydro-1H-isoquinolin-2-yl)-3-oxo-propenyl]-indol-1-yl}-acetic acid;
{3-[(E)-2-cyano-3-oxo-3-(7-trifluoromethyl-3,4-dihydro-2H-quinolin-1-yl)-propenyl]-indol-1-yl}-acetic acid;
(3-{(E)-2-cyano-2-[(3-fluoro-phenyl)-methyl-carbamoyl]-vinyl}-indol-1-yl)-acetic acid;
[3-((E)-2-cyano-3-dibenzo[b,f]azepin-5-yl-3-oxo-propenyl)-5-fluoro-indol-1-yl]-acetic acid;
{3-[(E)-2-cyano-3-(6,11-dihydro-dibenzo[b,e]azepin-5-yl)-3-oxo-propenyl]-5-fluoro-indol-1-yl}-acetic acid;
{3-[(E)-2-(benzyl-phenyl-carbamoyl)-2-cyano-vinyl]-5-fluoro-indol-1-yl}-acetic acid;
{3-[(E)-2-cyano-2-(cyclohexyl-phenyl-carbamoyl)-vinyl]-5-fluoro-indol-1-yl}-acetic acid;
{3-[(E)-2-(butyl-phenyl-carbamoyl)-2-cyano-vinyl]-5-fluoro-indol-1-yl}-acetic acid;
(3-{(E)-2-cyano-2-[(4-fluoro-phenyl)-methyl-carbamoyl]-vinyl}-5-fluoro-indol-1-yl)-acetic acid;
(3-{(E)-2-cyano-2-[(3-fluoro-phenyl)-methyl-carbamoyl]-vinyl}-5-fluoro-indol-1-yl)-acetic acid;
(3-{(E)-2-cyano-2-[(3,4-dichloro-phenyl)-methyl-carbamoyl]-vinyl}-5-fluoro-indol-1-yl)-acetic acid;
(3-{(E)-2-cyano-2-[methyl-(2-trifluoromethyl-phenyl)-carbamoyl]-vinyl}-5-fluoro-indol-1-yl)-acetic acid;
(3-{(E)-2-cyano-2-[(2,4-difluoro-phenyl)-methyl-carbamoyl]-vinyl}-5-fluoro-indol-1-yl)-acetic acid;
{3-[(E)-2-cyano-2-(phenyl-thiophen-3-ylmethyl-carbamoyl)-vinyl]-5-fluoro-indol-1-yl}-acetic acid;
{3-[(E)-2-cyano-3-oxo-3-(7-trifluoromethyl-3,4-dihydro-2H-quinolin-1-yl)-propenyl]-5-fluoro-indol-1-yl}-acetic acid;
(3-{(E)-2-cyano-2-[ethyl-(4-trifluoromethoxy-phenyl)-carbamoyl]-vinyl}-5-fluoro-indol-1-yl)-acetic acid;
{3-[(E)-2-cyano-3-(3,4-dihydro-1H-isoquinolin-2-yl)-3-oxo-propenyl]-5-fluoro-indol-1-yl}-acetic acid;
{3-[(E)-2-cyano-2-(phenethyl-phenyl-carbamoyl)-vinyl]-5-fluoro-indol-1-yl}-acetic acid;

[3-((E)-2-cyano-3-dibenzo[b,f]azepin-5-yl-3-oxo-propenyl)-6-methyl-indol-1-yl]-acetic acid;

{3-[(E)-2-cyano-3-(6,11-dihydro-dibenzo[b,e]azepin-5-yl)-3-oxo-propenyl]-6-methyl-indol-1-yl}-acetic acid;

{3-[(E)-2-cyano-3-(10,11-dihydro-dibenzo[b,f]azepin-5-yl)-3-oxo-propenyl]-6-methyl-indol-1-yl}-acetic acid;

{3-[(E)-2-(benzyl-phenyl-carbamoyl)-2-cyano-vinyl]-6-methyl-indol-1-yl}-acetic acid;

{3-[(E)-2-cyano-2-(cyclohexyl-phenyl-carbamoyl)-vinyl]-6-methyl-indol-1-yl}-acetic acid;

(3-{(E)-2-cyano-2-[(4-fluoro-phenyl)-methyl-carbamoyl]-vinyl}-6-methyl-indol-1-yl)-acetic acid;

{3-[(E)-2-(butyl-phenyl-carbamoyl)-2-cyano-vinyl]-6-methyl-indol-1-yl}-acetic acid;

{3-[(E)-2-cyano-2-(cyclohexyl-phenyl-carbamoyl)-vinyl]-7-methyl-indol-1-yl}-acetic acid; or (3-{(E)-2-cyano-2-[(4-fluoro-phenyl)-methyl-carbamoyl]-vinyl}-7-methyl-indol-1-yl)-acetic acid; or a salt of the compound.

7. The compound according to claim 1, wherein the compound is of formula $I_{C2}$

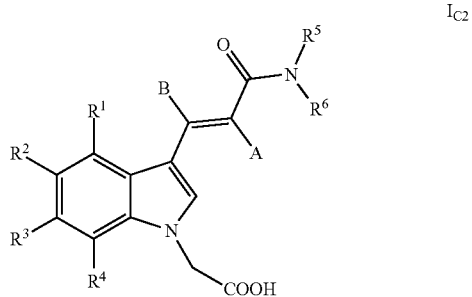

wherein

A represents cyano;

B represents hydrogen;

$R^1$, $R^2$, $R^3$ and $R^4$ independently represent hydrogen, alkyl, halogen, nitro, cyano or formyl; and $R^5$ and $R^6$ independently represent hydrogen, alkyl, cycloalkyl, cycloalkyl-alkyl, heteroaryl, heteroaryl-alkyl, alkenyl, carboxyalkyl, cyanoalkyl, diphenylalkyl, aryl, aryl-alkoxy-aryl, aryl-alkyl, aryl-alkyl-aryl, arylcarbonyl-aryl or aryloxy-aryl, or $R^5$ and $R^6$, together with the nitrogen atom to which they are attached, form a heterocyclic ring system;

provided that at least one of the following conditions must be met:

one of $R^1$, $R^2$, $R^3$ and $R^4$ is different from a hydrogen atom; or when $R^5$ and $R^6$ are such that they do not form a heterocyclic ring system together with the nitrogen atom to which they are attached, then both $R^5$ and —$R^6$ are different from hydrogen and one of $R^5$ and $R^6$ is different from alkyl; or when $R^5$ and $R^6$ are such that they form a heterocyclic ring system together with the nitrogen atom to which they are attached, then said heterocyclic ring system is neither an unsubstituted or substituted piperidine nor an unsubstituted or substituted piperazine; or a salt of the compound.

8. A pharmaceutical composition comprising at least one compound according to claim 1 and a pharmaceutically acceptable carrier.

9. A method for treating chronic or acute allergic immune disorders comprising the administration of a therapeutically effective amount of the compound according to claim 1, wherein the disorder is allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, anaphylactic shock, urticaria, eczema, itching, inflammation, ischemia-reperfusion injury, pleuritis, ulcerative colitis, Churg-Strauss syndrome, sinusitis, basophilic leukemia, or basophilic leukocytosis.

10. The compound of claim 1, wherein the compound is {3-[(E)-2-cyano-3-(3,4-dihydro-2H-quinolin-1-yl)-3-oxo-propenyl]-indol-1-yl}-acetic acid.

11. The compound of claim 1, wherein:

A is cyano;

B is hydrogen;

$R^1$, $R^2$, $R^3$ and $R^4$ are all hydrogen atoms or one of $R^1$, $R^2$, $R^3$ and $R^4$ is halogen while the others are all hydrogen; and at least one of $R^5$ and $R^6$ is chosen from the group consisting of heteroaryl, heteroaryl-alkyl, diphenylalkyl, aryl, aryl-alkoxy-aryl, aryl-alkyl, aryl-alkyl-aryl, arylcarbonyl-aryl and aryloxy-aryl; or $R^5$ and $R^6$, together with the nitrogen atom to which they are attached, form a heterocyclic ring system; or a salt of the compound.

12. A method for treating chronic or acute allergic immune disorders comprising the administration of a therapeutically effective amount of the compound according to claim 11, wherein the disorder is allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, anaphylactic shock, urticaria, eczema, itching, inflammation, ischemia-reperfusion injury, pleuritis, ulcerative colitis, Churg-Strauss syndrome, sinusitis, basophilic leukemia, or basophilic leukocytosis.

13. The method for treating chronic or acute allergic immune disorders comprising the administration of a therapeutically effective amount of the compound according to claim 6, wherein the disorder is allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, anaphylactic shock, urticaria, eczema, itching, inflammation, ischemia-reperfusion injury, pleuritis, ulcerative colitis, Churg-Strauss syndrome, sinusitis, basophilic leukemia, or basophilic leukocytosis.

* * * * *